US010925479B2

(12) United States Patent
Kurtz et al.

(10) Patent No.: US 10,925,479 B2
(45) Date of Patent: *Feb. 23, 2021

(54) NETWORKED SYSTEM OF MOBILE COMMUNICATION PLATFORMS FOR NONPHARMACOLOGIC CONSTRICTION OF A PUPIL

(71) Applicants: Ronald Michael Kurtz, Irvine, CA (US); Gergely T. Zimanyi, Berkeley, CA (US)

(72) Inventors: Ronald Michael Kurtz, Irvine, CA (US); Gergely T. Zimanyi, Berkeley, CA (US)

( * ) Notice: Subject to any disclaimer, the term of this patent is extended or adjusted under 35 U.S.C. 154(b) by 568 days.

This patent is subject to a terminal disclaimer.

(21) Appl. No.: 15/375,149

(22) Filed: Dec. 11, 2016

(65) Prior Publication Data

US 2018/0103839 A1    Apr. 19, 2018

Related U.S. Application Data

(63) Continuation-in-part of application No. 15/293,269, filed on Oct. 13, 2016, now Pat. No. 10,406,352.

(51) Int. Cl.
*A61B 5/00* (2006.01)
*A61B 3/00* (2006.01)
(Continued)

(52) U.S. Cl.
CPC .......... *A61B 3/0008* (2013.01); *A61B 3/0025* (2013.01); *A61B 3/14* (2013.01);
(Continued)

(58) Field of Classification Search
CPC ........ G02B 27/0172; G02B 2027/0178; G02B 27/017; G02B 2027/0138; G02B 6/0013;
(Continued)

(56) References Cited

U.S. PATENT DOCUMENTS 5,410,376 A * 4/1995 Cornsweet ............. A61B 3/113
351/209
5,490,098 A * 2/1996 Kardon ................. A61B 3/112
351/200
(Continued)

*Primary Examiner* — May A Abouelela

(57) ABSTRACT

A networked system of ophthalmic stimulators for temporarily constricting eye-pupils comprises a set of ophthalmic stimulators, each ophthalmic stimulator including a mobile irradiation control system, to generate an irradiation control signal; an irradiation source, coupled to the irradiation control system, to generate an irradiation; and an irradiation delivery system, coupled to the mobile irradiation control system, to receive the irradiation from the irradiation source, and to deliver a patterned irradiation to an iris of the eye; wherein the mobile irradiation control system controls at least one of the irradiation source and the irradiation delivery system with the irradiation control signal so that the patterned irradiation causes a temporary constriction of the pupil of the eye, without causing a permanent constriction of the pupil; and a central station, including a central image processor, wherein the mobile irradiation control systems and the central station are configured to communicate through a communication network.

17 Claims, 41 Drawing Sheets

(51) Int. Cl.
*A61B 3/14* (2006.01)
*A61N 5/06* (2006.01)
*A61F 9/008* (2006.01)

(52) U.S. Cl.
CPC .......... *A61B 5/0013* (2013.01); *A61B 5/0022* (2013.01); *A61B 5/6898* (2013.01); *A61N 5/0625* (2013.01); *A61B 2560/0431* (2013.01); *A61B 2576/00* (2013.01); *A61F 2009/00876* (2013.01)

(58) Field of Classification Search
CPC ....... G02B 7/34; G06F 3/013; G06F 17/5009; G06F 21/32; A61B 3/0025; A61B 3/14; A61B 3/113; A61B 3/0041; A61B 3/0008; A61B 3/112; A61B 3/12; A61B 3/18; A61B 1/05
USPC ............. 600/300, 558; 351/205, 221; 606/5; 340/575
See application file for complete search history.

(56) References Cited

U.S. PATENT DOCUMENTS

| | | | | |
|---|---|---|---|---|
| 5,883,691 A * | 3/1999 | Ishikawa | | A61B 3/112 351/205 |
| 6,022,109 A * | 2/2000 | Dal Santo | | A61B 3/112 351/221 |
| 6,199,985 B1 * | 3/2001 | Anderson | | A61B 3/112 351/221 |
| 6,346,887 B1 * | 2/2002 | Van Orden | | A61B 5/18 180/272 |
| 6,669,651 B1 * | 12/2003 | Fukushima | | A61B 3/112 600/558 |
| 7,083,280 B2 * | 8/2006 | Hakamata | | A61B 3/11 351/200 |
| 7,204,590 B1 * | 4/2007 | Lenoir | | A61B 3/10 351/205 |
| 7,515,054 B2 * | 4/2009 | Torch | | A61B 3/112 340/573.1 |
| RE41,376 E * | 6/2010 | Torch | | A61B 3/0066 340/573.1 |
| 7,854,511 B2 * | 12/2010 | Molnar | | A61B 3/12 351/218 |
| 7,967,442 B2 * | 6/2011 | Siminou | | A61B 3/0058 351/246 |
| 8,092,020 B2 * | 1/2012 | Kolanko | | A61B 3/00 351/205 |
| 8,393,734 B2 * | 3/2013 | Privitera | | A61B 3/112 351/202 |
| 8,890,946 B2 * | 11/2014 | Publicover | | H04N 7/18 348/78 |
| 9,101,312 B2 * | 8/2015 | Waldorf | | A61B 3/032 |
| 9,600,069 B2 * | 3/2017 | Publicover | | G06F 3/013 |
| 10,039,445 B1 * | 8/2018 | Torch | | A61B 3/112 |
| 2002/0099305 A1 * | 7/2002 | Fukushima | | A61B 3/112 600/558 |
| 2004/0169817 A1 * | 9/2004 | Grotehusmann | | A61B 5/1171 351/204 |
| 2008/0161716 A1 * | 7/2008 | Livne | | A61N 1/36046 600/558 |
| 2010/0016754 A1 * | 1/2010 | Whillock | | A61B 3/113 600/558 |
| 2011/0007269 A1 * | 1/2011 | Trumm | | G02C 13/005 351/204 |
| 2011/0077548 A1 * | 3/2011 | Torch | | A61B 3/112 600/558 |
| 2011/0299033 A1 * | 12/2011 | Wada | | G02C 7/027 351/204 |
| 2012/0150064 A1 * | 6/2012 | DellaVecchia | | A61B 3/12 600/558 |
| 2013/0050642 A1 * | 2/2013 | Lewis | | A61B 3/113 351/204 |
| 2014/0148737 A1 * | 5/2014 | Homer | | A61H 23/00 601/15 |
| 2014/0171756 A1 * | 6/2014 | Waldorf | | A61B 3/032 600/301 |
| 2015/0282704 A1 * | 10/2015 | Maddess | | A61B 5/4005 600/558 |
| 2015/0286076 A1 * | 10/2015 | Nakamura | | G02C 13/005 351/204 |
| 2016/0073874 A1 * | 3/2016 | Tsai | | A61B 5/1103 600/558 |
| 2017/0007119 A1 * | 1/2017 | Cornsweet | | A61B 3/113 |
| 2018/0125406 A1 * | 5/2018 | Yamada | | A61B 5/165 |

* cited by examiner

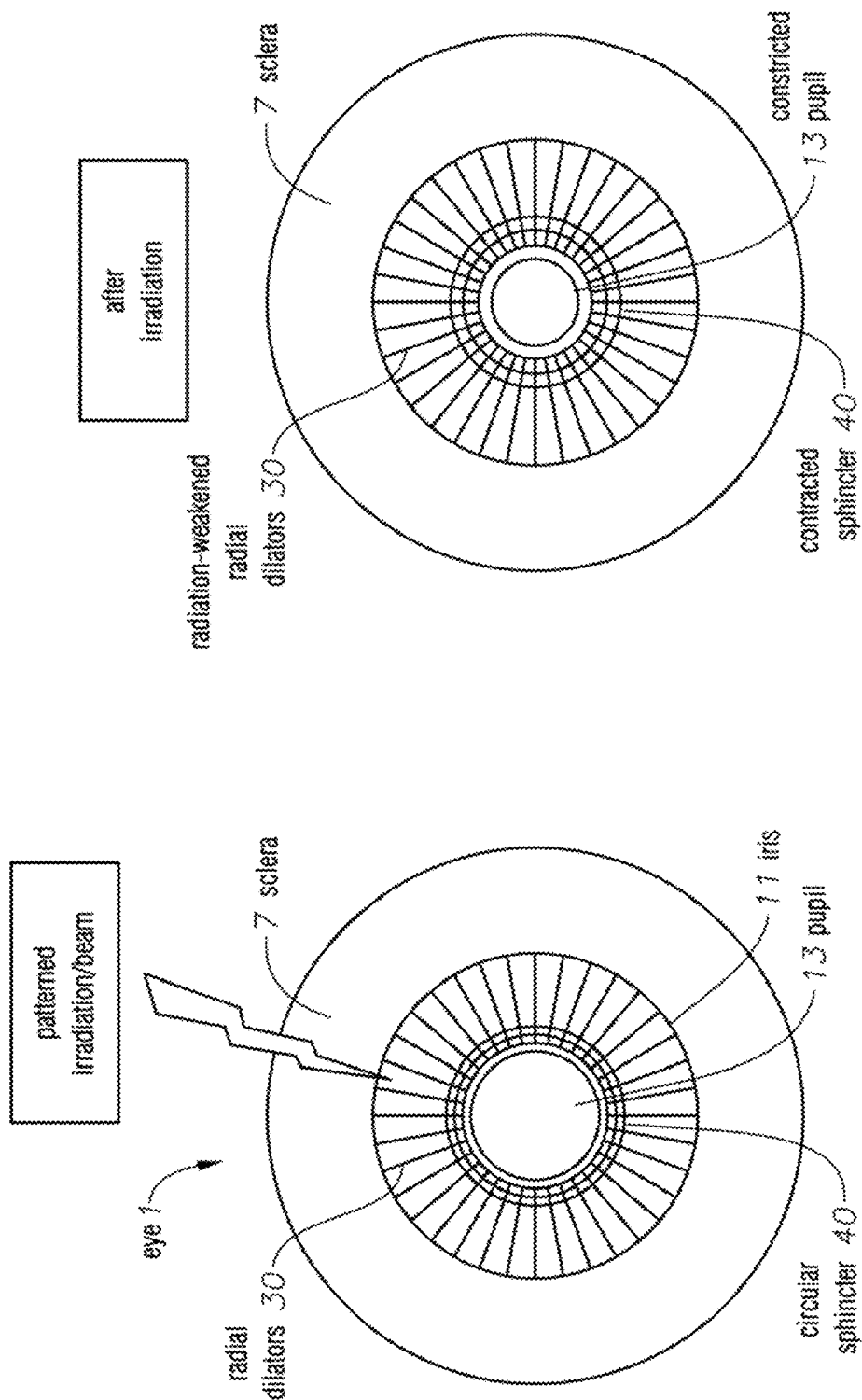

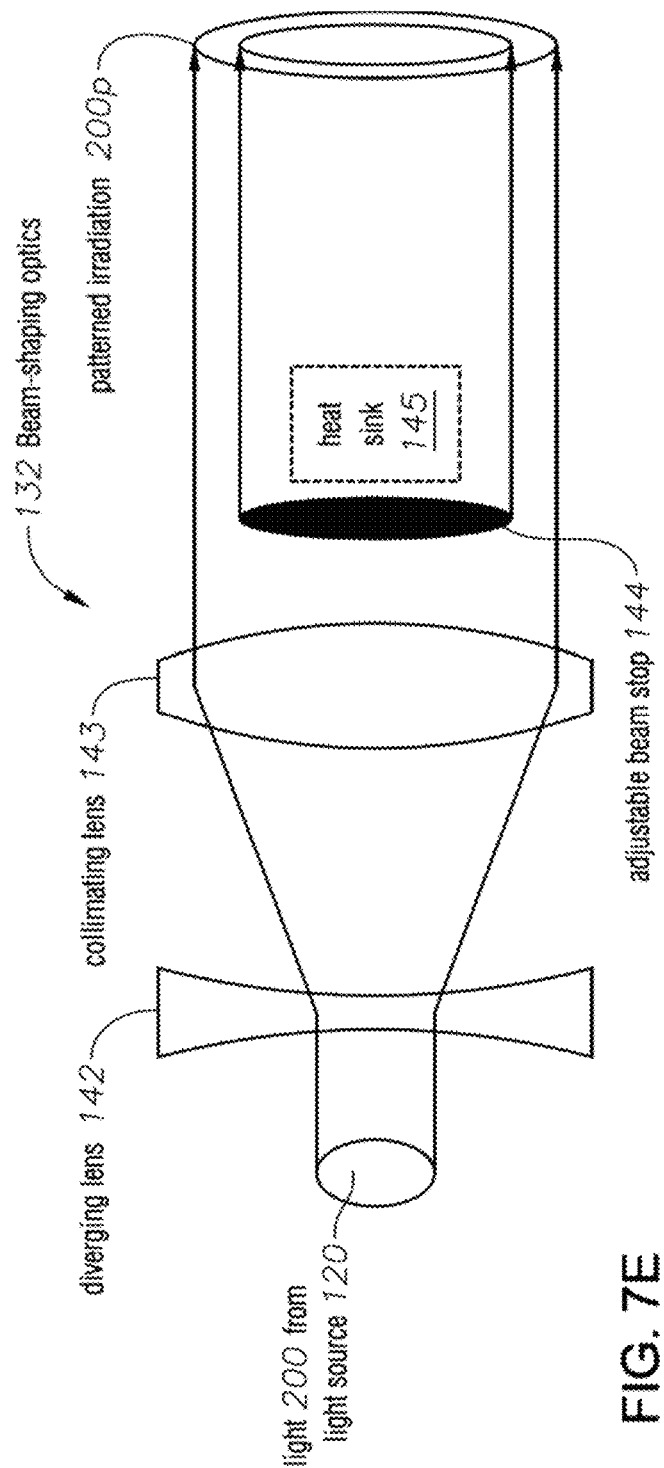
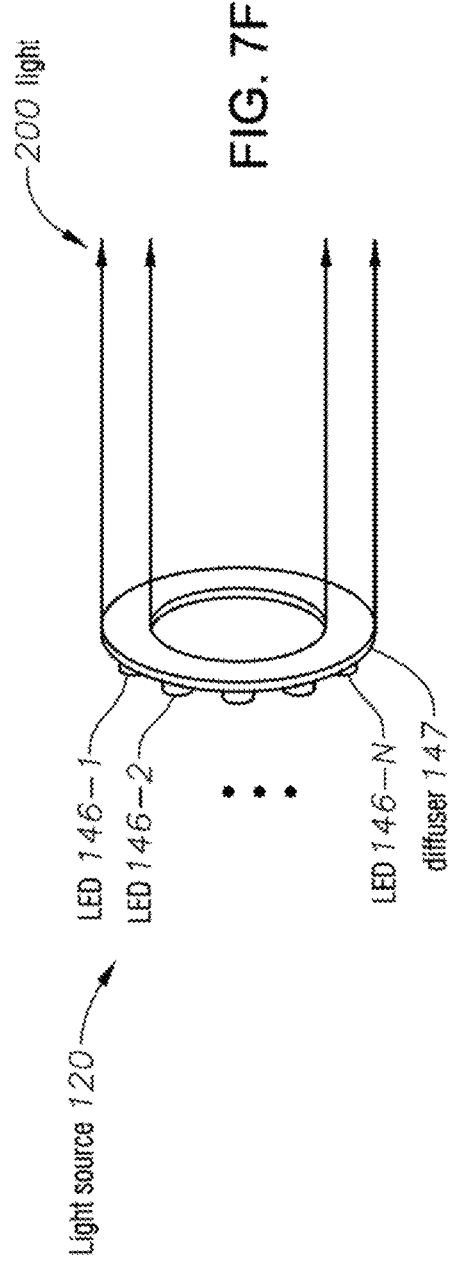
FIG. 7E
FIG. 7F

NETWORKED SYSTEM OF MOBILE COMMUNICATION PLATFORMS FOR NONPHARMACOLOGIC CONSTRICTION OF A PUPIL

CROSS-REFERENCE TO RELATED PATENT DOCUMENTS

This application is a continuation-in-part of U.S. Patent Application: "System for temporary nonpharmacologic constriction of the pupil", by Ronald M. Kurtz and Gergely T. Zimanyi, with application Ser. No. 15/293,269, filed on Oct. 13, 2016; hereby incorporated by reference in its entirety.

FIELD OF INVENTION

This invention relates to a system for pupil constriction, more precisely, to a system of temporary, non-pharmacological construction of a pupil of an eye.

BACKGROUND

A number of devices that make use of the increased depth of field of a small aperture have been proposed for use in ophthalmology, and developed to improve vision. These devices are particularly promising to improve near vision for those who have presbyopia. Examples of such devices include small aperture corneal inlays, reduced-aperture intraocular lenses, as well as other aperture implants that are meant to impact light propagation along the visual axis. While effective, these surgically implanted permanent inlays carry the risk inherent with any implantable device, such as inflammation, infection, or displacement that may require secondary surgical procedures to remove the implant and may necessitate performing other procedures.

Pharmacological methods have also been proposed using medications such as pilocarpine and other agents to temporarily constrict the pupil. While these drugs can temporarily improve vision, they generally require frequent instillation of drops, and can be associated with undesirable side effects, such as headaches.

An alternative approach has been proposed by Hickenbotham in US patent application 2013/0226161, which utilizes a laser to cauterize certain portions of the iris to cause a permanent constriction of the pupil. While this approach offers some advantages over implants and medications, the permanent constriction of the pupil, achieved by a controlled damaging of the iris dilator muscle, does not allow for a trial of the effect, and once performed, leaves the patient with a permanent deficit in iris function. In addition, the exact shape of the constricted pupil may be difficult to control, and may result in odd, irregular, oval, or other undesired pupil shapes. Therefore, the medical need persists to develop a non-pharmacological, non-permanent vision improvement that does not involve inserting a small-aperture object surgically into the eye.

In some embodiments, an ophthalmic stimulator for temporarily constricting a pupil of an eye comprises an irradiation control system, to generate an irradiation control signal; an irradiation source, coupled to the irradiation control system, to generate an irradiation; and an irradiation delivery system, coupled to the irradiation control system, to receive the irradiation from the irradiation source, and to deliver a patterned irradiation to an iris of the eye; wherein the irradiation control system controls at least one of the irradiation source and the irradiation delivery system with the irradiation control signal so that the patterned irradiation causes a temporary constriction of the pupil of the eye, without causing a permanent constriction of the pupil.

In some embodiments, a method for temporarily constricting a pupil of an eye by an ophthalmic stimulator comprises generating an irradiation control signal by an irradiation control system; generating an irradiation by an irradiation source, coupled to the irradiation control system; receiving the irradiation and delivering a patterned irradiation to an iris of the eye with an irradiation delivery system; and controlling at least one of the irradiation source and the irradiation deliver system by the irradiation control signal of the irradiation control system so that the patterned irradiation is causing a temporary constriction of the pupil of the eye, without causing a permanent constriction of the pupil.

In some embodiments, an ophthalmic stimulator for constricting a pupil of an eye comprises an irradiation control system, to generate an irradiation control signal; an irradiation source, coupled to the irradiation control system, to generate an irradiation; and an irradiation delivery system, coupled to the irradiation control system, to receive the irradiation from the irradiation source, and to deliver a patterned irradiation to an iris of the eye; wherein the irradiation control system controls at least one of the irradiation source and the irradiation delivery system with the irradiation control signal so that the patterned irradiation causes a long-term constriction of the pupil of the eye.

In some embodiments, an ophthalmic stimulator for temporarily constricting a pupil of an eye comprises an irradiation control system, to generate an irradiation control signal; a light source, coupled to the irradiation control system, to generate a light beam; and a beam-shaping optics, coupled to the irradiation control system, to receive the light beam from the light source, and to deliver a light ring to an iris of the eye; wherein the irradiation control system controls at least one of the light source and the beam-shaping optics with the irradiation control signal so that the light ring causes a temporary constriction of the pupil of the eye, without causing a permanent constriction of the pupil.

In some embodiments, an ophthalmic stimulator for temporarily constricting a pupil of an eye comprises a digital beam controller, to generate a digital beam-control signal; a light source, coupled to the beam controller, to generate a light beam; and a digitally controlled beam modulator, to receive the digital beam-control signal from the beam controller, to receive the light beam from the light source, and to modulate the received light beam into a patterned light, delivered to an iris of the eye; wherein the beam controller controls at least one of the light source and the digitally controlled beam modulator with the digital beam-control signal so that the patterned light causes a temporary constriction of the pupil of the eye, without causing a permanent constriction of the pupil.

In some embodiments, an ophthalmic stimulator for temporarily constricting a pupil of an eye comprises an irradiation control system, having a feedback system, to generate an irradiation control signal using a feedback of the feedback system; an irradiation source, coupled to the irradiation control system, to generate an irradiation; and an irradiation delivery system, having a targeting system and coupled to the irradiation control system, to receive the irradiation from the irradiation source, and to direct a patterned irradiation in a pattern to a treatment region of an iris of the eye using the targeting system; wherein the irradiation control system controls at least one of the irradiation source and the irradiation delivery system with the irradiation control signal so that the patterned irradiation causes a temporary constriction of the pupil, without causing a permanent constriction of the pupil.

In some embodiments, an ophthalmic stimulator for temporarily constricting a pupil of an eye comprises a mobile irradiation control system, to generate an irradiation control signal; an irradiation source, coupled to the irradiation control system, to generate an irradiation; and an irradiation delivery system, coupled to the mobile irradiation control system, to receive the irradiation from the irradiation source, and to deliver a patterned irradiation to an iris of the eye; wherein the mobile irradiation control system controls at least one of the irradiation source and the irradiation delivery system with the irradiation control signal so that the patterned irradiation causes a temporary constriction of the pupil of the eye, without causing a permanent constriction of the pupil.

In some embodiments, a networked system of ophthalmic stimulators for temporarily constricting eye-pupils comprises a set of ophthalmic stimulators, each ophthalmic stimulator including a mobile irradiation control system, to generate an irradiation control signal; an irradiation source, coupled to the irradiation control system, to generate an irradiation; and an irradiation delivery system, coupled to the mobile irradiation control system, to receive the irradiation from the irradiation source, and to deliver a patterned irradiation to an iris of the eye; wherein the mobile irradiation control system controls at least one of the irradiation source and the irradiation delivery system with the irradiation control signal so that the patterned irradiation causes a temporary constriction of the pupil of the eye, without causing a permanent constriction of the pupil; and a central station, including a central image processor, wherein the mobile irradiation control systems of the of the ophthalmic stimulators and the central station are configured to communicate through a communication network.

BRIEF DESCRIPTION OF THE FIGURES

FIGS. 3A-B illustrate an effect of applying an irradiation to the iris.

FIGS. 7A-F illustrate embodiments of the ophthalmic stimulator 100 with a beam shaping optics 134.

DETAILED DESCRIPTION

Embodiments of the invention address the above described needs in the following manner. Some embodiments provide systems and methods for a temporary constriction of the pupil without the need of medication therapy. The duration of the constriction can be controlled by a selection of treatment parameters. In a suitable range of treatment parameters, the procedure can be fully reversible: after a characteristic time, the pupils return to essentially their original diameter without further treatment. The pupils can be re-constricted by applying the treatment repeatedly. Therefore, the here-described methods and devices provide the advantages of a temporary, but long lasting vision improvement, while avoid the hazards associated with (1) aperture implants and inlays, inserted by a surgical procedure, (2) permanent destruction of tissue, and (3) pharmaceutical approaches and their undesirable side-effects.

Some embodiments achieve these advantages by heating the iris by an irradiation to a suitable temperature range, (1) to cause a temporary inactivation of the iris dilator muscle, and, in some cases, (2) to enhance an action of the iris constrictor sphincter muscle. This irradiative heat treatment can be applied for a time sufficiently long to cause a reduction in contractile activity, but short enough to avoid causing permanent tissue damage. While the detailed mode of action is yet to be clarified, this effect may be mediated by inactivation of the actin-myosin complex in the exposed muscle.

Figure 1:
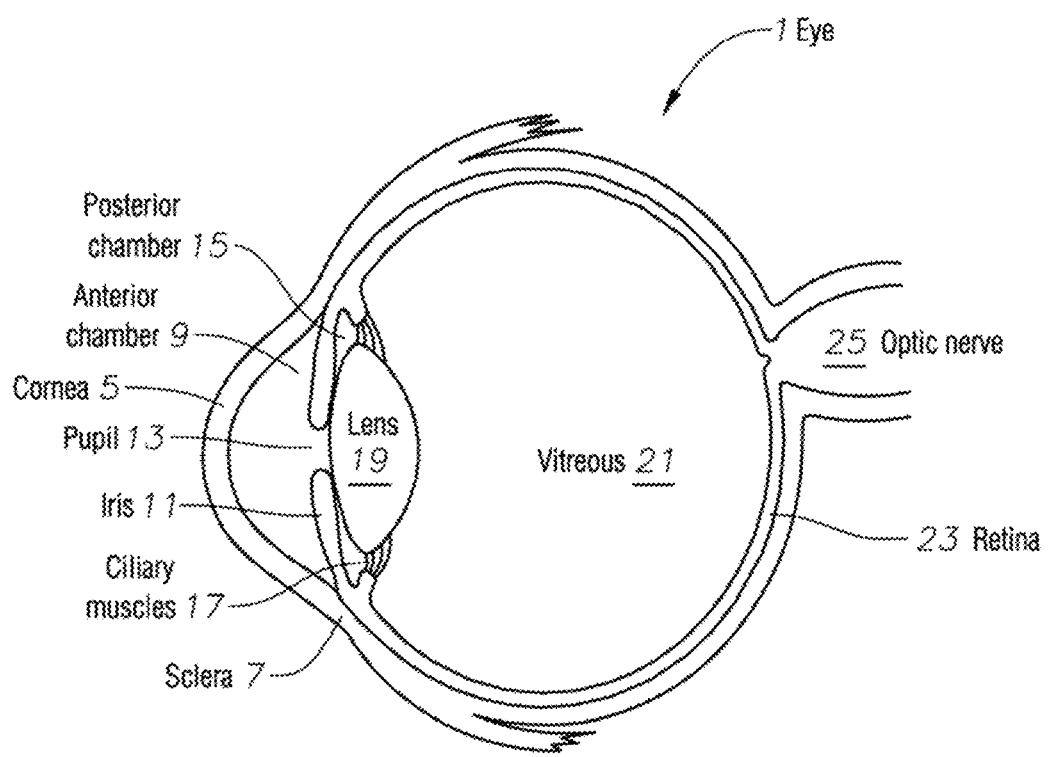
FIG. 1 illustrates an eye 1.

FIG. 1 shows a cross section of an eye 1. The eye 1 includes the well known constituents: a cornea 5, where light enters the eye 1, and a sclera 7, an opaque, fibrous protective outer layer of the eye 1 that contains collagen and elastic fibers. Distal to the cornea 5 is an anterior chamber 9 that contains an aqueous humor. The anterior chamber 9 is separated from a posterior chamber 15 by an iris 11. An opening at a center of the iris 11 is a pupil 13 that allows the light to proceed toward the posterior segment of the eye 1. Behind the pupil 13, ciliary muscles 17 hold a lens 19 in a central position. These ciliary muscles 17 can also delimit the lens 19 as part of accommodating the vision to the distance of the target the eye is looking at. With advancing age, the ciliary muscles 17 slowly loose their ability to deform and adapt the lens 19 to varying vision distances: a condition typically referred to as presbyopia. Behind the lens 19 is a vitreous 21. As the light crosses the vitreous 21, it eventually hits the retina 23. The electric stimuli, generated by the incoming light in the retina 23, are transmitted by the optic nerve 25 towards the brain.

Figure 2A:
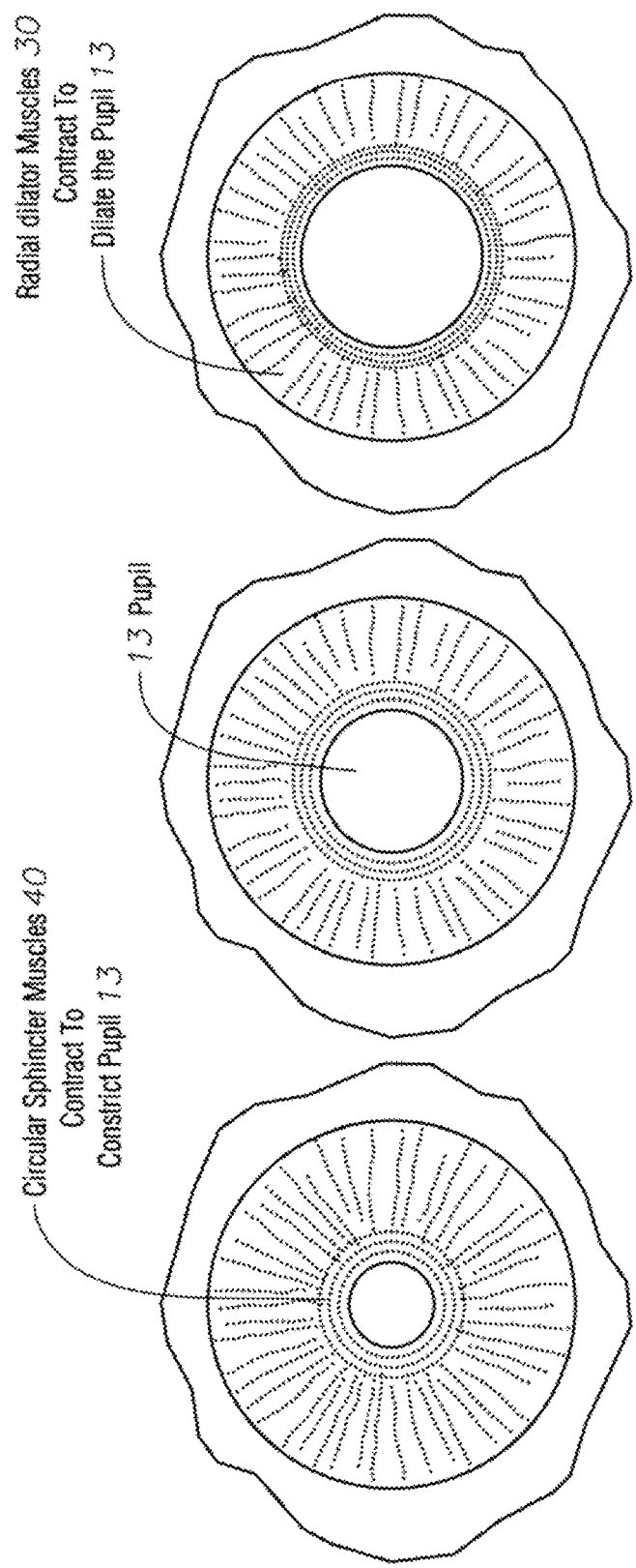
FIGS. 2A-B illustrate the pupil under different illuminations.
Figure 2B:
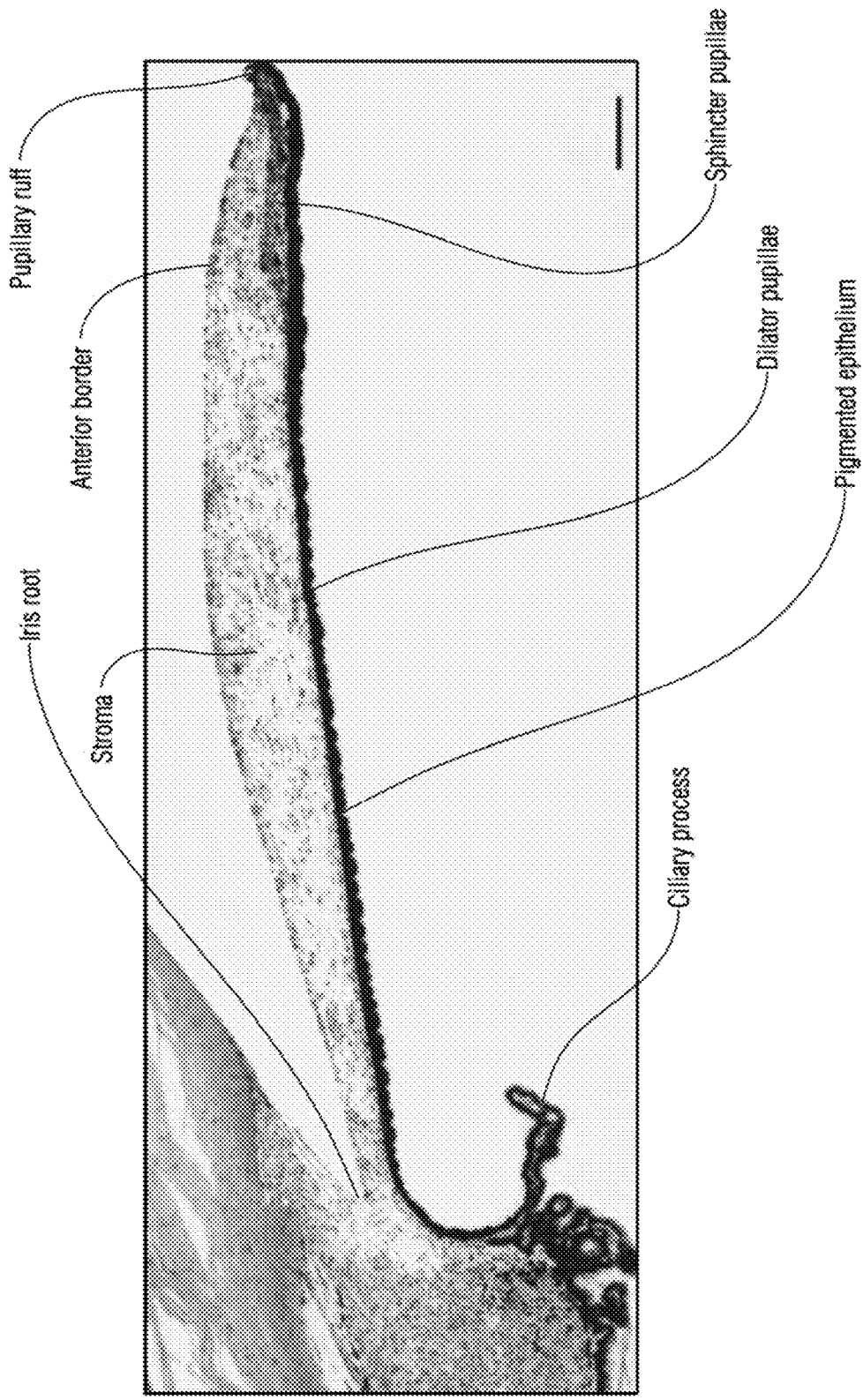

FIG. 2A-B illustrate that the iris 11 includes a circular sphincter muscle 40 around the pupil 13, capable of shrinking the perimeter of the pupil 13, thus constricting it. At the same time, the iris 11 also includes radial dilator muscles 30 that specialize in expanding, or enlarging, the pupil 13. The competition of the sphincter muscles 40 and dilator muscles 30 determines the eventual radius of the pupil 13. FIG. 2A illustrates in its left panel that in strong light the contracting sphincter muscles 40 constrict the pupil 13. FIG. 2A illustrates in its middle panel the pupil 13 in an average light. FIG. 2A illustrates in its right panel that in low light conditions, the radial dilator muscles 30 dominate the sphincter muscles 40 and dilate the pupil to enhance the amount of light directed to the retina 23.

FIG. 2B illustrates a cross section of the iris 11 from the side. It is well visible that the sphincter pupillae 40 is positioned along the edge of the pupil 13, the pupillary ruff while the radial dilator pupillae 30 are located radially outward, farther from the edge of the pupil 13.

The anatomy of the muscles of the iris 11 is also important. The dilator muscle 30 fibers are typically located near the distal portion of the iris 11, adjacent to the iris pigmented epithelium. In contrast, the constrictor sphincter muscles 40 are more superficial and central, located towards the pupil's edge or margin. Details of the anatomy of these muscles can be found in much greater detail in Junqueira L. C., Carneiro J. 2005. Basic Histology, Eleventh Edition. The McGraw-Hill Companies, Inc. United States of America.

FIGS. 3A-B illustrate a principle of embodiments of the invention. FIG. 3A illustrates that a patterned irradiation can be applied to the iris 11 for a limited time period, such as 1-100 seconds, with less time required when higher temperatures are applied. The pattern is typically a ring of light, or light-ring. The irradiation raises the temperature of the iris 11 in a treatment region. The tissue of the iris 11 can be heated to temperatures that are not sufficient to cauterize or destroy the tissue, but are capable of reducing an activity, or responsiveness of the targeted tissues.

FIG. 3B illustrates the outcome of the irradiation. The heat treatment reduces the activity of the iris dilator muscle and this allows the pupillary constrictor, or sphincter, muscle to reduce the pupil's diameter. Reducing the pupil's diameter reduces the aberrations of the imaging of the eye, sometimes referred to as the pinhole effect in optics. Reducing the aberrations extends the depth of focus, and thereby compensates the emergence of presbyopia in an aging eye. Since this method utilizes the natural constrictor muscle to effect the pupil size change, the risk of pupil de-centration is less than in the case of surgical implants, discussed previously.

Figure 4A:
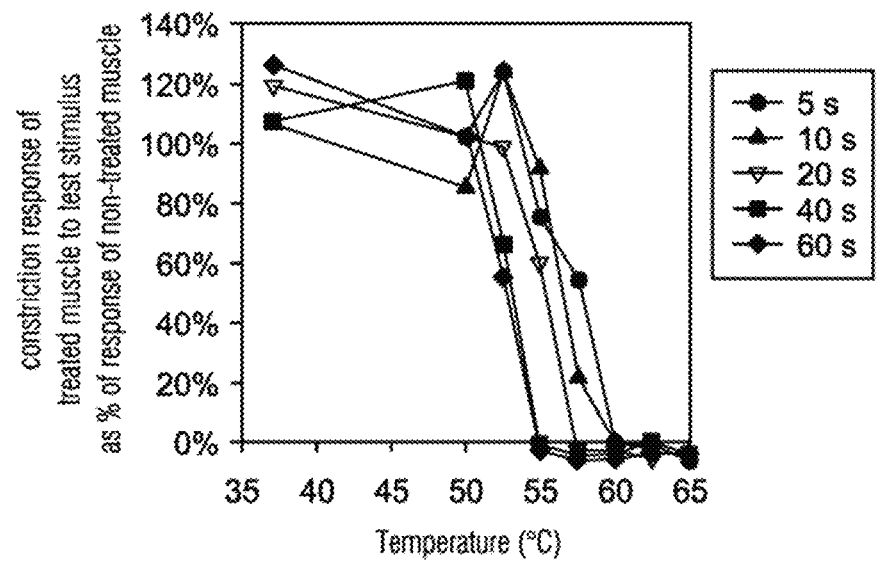
FIGS. 4A-B illustrate the effect of irradiation on the muscle response.
Figure 4B:
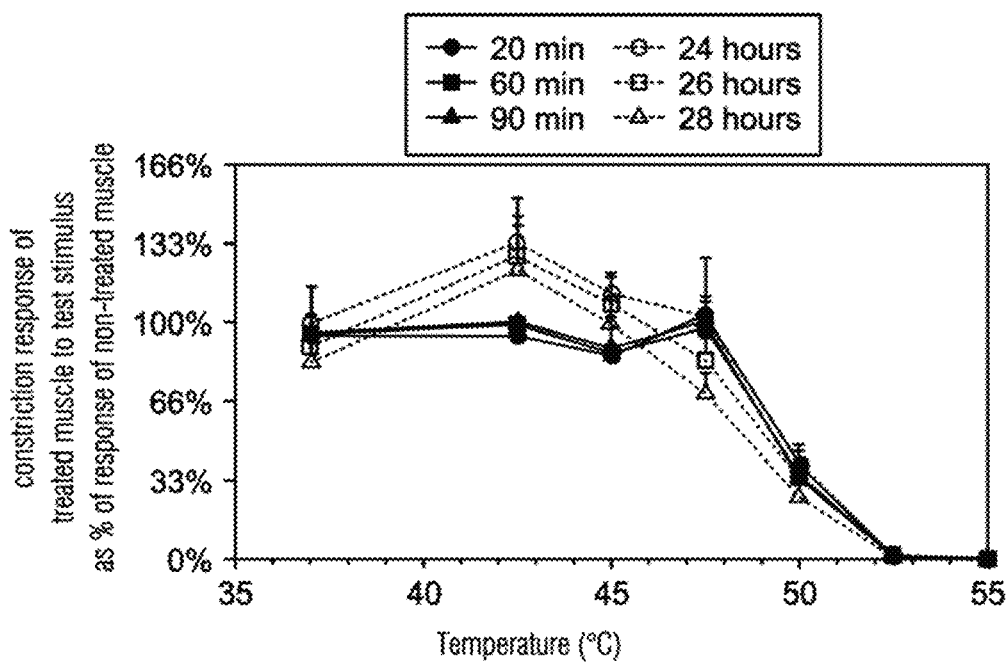

FIGS. 4A-B illustrate that heat treatments have been already studied and demonstrated to reduce muscle activity in human tissues, such as in the lung and the prostate, which have smooth muscle tissues similar to that of the iris. The heat treatment can reduce, or inhibit, muscle activity in these tissues. The duration of inactivity can last for hours to days in these systems (see Am. J. Respir. Cell Mol. Biol. Vol 44. pp 213-221, 2011). FIG. 4A illustrates the effect of heat treatments on lung smooth muscle. The muscle tissue was heated for a treatment time between 5 s and 60 s. After the heat treatment, a test stimulus was administered to the heat-treated and the untreated muscles. The graph reports the ratio of responses to this test as a function of the treatment temperature of the tissue. Visibly, as the treatment temperature exceeded 50 Celsius, or Centigrade, the response of the treated muscle to the test stimulus gradually decreased. For heat treatments above 55-60 Celsius, the response became negligible: the muscle was deactivated by the treatment.

FIG. 4B illustrates the same ratio of responses of treated muscles to non-treated muscles, with the difference that it indicates how long the effect lasted. As the curves show, the de-activation of the smooth muscle with heat treatments raising the muscle temperature above 50-55 Celsius lasted at least for 28 hours, and possibly longer. This remarkably long-lasting deactivation of smooth muscle in response to such a mild and short temperature increase is utilized by embodiments described in this document.

Figure 5A:
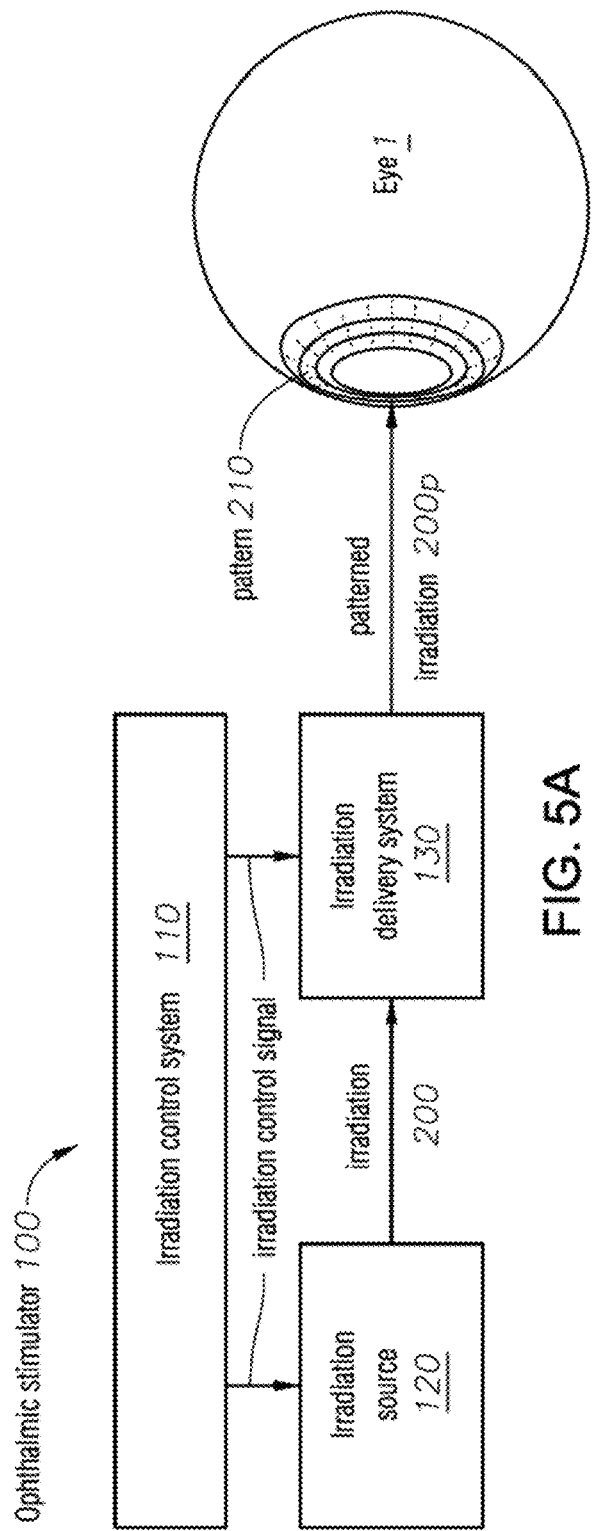
FIGS. 5A-B illustrate embodiments of the ophthalmic stimulator 100, and the permanent ophthalmic stimulator 100'.

FIG. 5A illustrates an ophthalmic stimulator 100 for temporarily constricting a pupil 13 of an eye 1, building on the just-described observations, comprising an irradiation control system 110, to generate an irradiation control signal; art irradiation source 120, coupled to the irradiation control system 110, to generate an irradiation 200; and an irradiation delivery system 130, coupled to the irradiation control system 110, to receive the irradiation 200 from the irradiation source 120, and to deliver a patterned irradiation 200p to an iris 11 of the eye 1 in a pattern 210. In embodiments, the irradiation control system 110 controls at least one of the irradiation source 120 and the irradiation delivery system 130 with the irradiation control signal so that the patterned irradiation 200p causes a temporary constriction of the pupil 13 of the eye 1, without causing a permanent constriction of the pupil 13.

The irradiation control system 110 can include a memory, to store executable programs and applications; a processor, to execute at least one of a stored program and an installed application; and a user interface, to receive input from a user in relation to an operation of the memory and the processor.

In some embodiments of the ophthalmic stimulator 100, the irradiation source 120 can include an incoherent light source, such as a light source, a LED, a lamp, an infrared source, a broad-band source, a narrow-band source, a radio-frequency source, an electromagnetic radiation source, or a sound source, to generate a light beam, an electromagnetic irradiation, an infrared beam, a LED light, or a sound. A separate class of irradiation sources can include a coherent light source, such as a laser, a pulsed laser, or a continuous wave (CW) laser.

The just discussed classes of incoherent and coherent irradiation sources have different advantages and drawbacks. Lasers offer good control and unparalleled precision. At the same time, laser beams have a very small diameter, often less than 100 microns. Therefore, to affect larger treatment regions, they require a complex and expensive, digitally controlled optical system, such as a scanning system. These laser-plus-scanning systems offer great control and precision. At the same time, they can be expensive, and can introduce multiple sources of unreliability and performance degradation, a potential problem in medical applications, where high reliability is essential. Using lasers and scanners may therefore necessitate regular maintenance. Also, laser beams can be very intense, thus if a laser gets pointed to an unintended part of an ophthalmic tissue, it can cause substantial damage. Therefore, much stronger safety systems and precautions are needed in laser systems.

In contrast, non-coherent light sources, such as LEDs, infrared sources, lamps, infrared sources, and others may offer less precision and control. However, this control may be sufficient for the purposes of the here-described treatment. Also, incoherent light sources can make the ophthalmic stimulator 100 much simpler, lighter, and smaller at the same time. Since they typically do not require a digitally controlled scanning system, these incoherent light sources can also be cheaper to maintain and can be more robust and reliable. Finally, since these light sources are less intense, systems with incoherent light sources may require less stringent safety systems and measures. All in all, a comparative analysis of the competing advantages and disadvantages is performed when a system designer decides whether to use a coherent, or an incoherent light source as the irradiation source 120 of the ophthalmic stimulator 100.

Embodiments of the ophthalmic stimulator 100 can be characterized by numerous treatment parameters. These treatment parameters can include the followings. A power density of the patterned irradiation 200p of the irradiation delivery system 130 can be in the range of 0.1-1000 mW/cm$^2$, in some designs in the range of 1-100 mW/cm$^2$. A total power delivered by the patterned irradiation 200$p$ to the iris can be in the range of: 0.1-1,000 mW, in some designs in the range of 1-100 mW. A total energy, deposited by the patterned irradiation 200$p$ during the treatment can be in the range of 10 microJ-10 J, in some designs in the range of 100 microJ-100 mJ.

A wavelength of the irradiation source 120 can be in the range of 400-4,000 nm, in some designs, in the range of 600-1,500 nm. The wavelength of some stimulators 100 can be selected by noting in FIG. 2B, that the muscle fibers of the radial dilators 30 are located in the proximity of the pigmented epithelium of the iris 11. This fact can be used to selectively target and heat the dilator muscles 30 indirectly. The pigmented epithelium layers may not have essential functions that would be negatively affected by heating, such as undergoing an irrecoverable reactivity change. To build on this, irradiation sources 120 can emit the irradiation 200 with a wavelength close to the wavelength where the absorption of the pigmented epithelium shows a maximum, or is at least greatly enhanced. Such irradiation sources 120 can heat the pigments particularly efficiently, possibly to temperatures 55 C, 60 C, possibly even to 60-65 Celsius. The heated pigmented epithelia can then provide a secondary, or indirect heating to the dilator muscles 30, located in their immediate proximity, to the medically preferred 50-55 Celsius temperatures.

FIG. 2B also illustrates that the dilator muscles 30 are in the distal region of the iris 11. Therefore, irradiation with wavelengths that penetrate the iris tissue more efficiently and to greater depths can be favored to make sure that the dilator muscles 30 are well heated. In several ophthalmologic studies, irradiation with longer wavelengths showed greater penetration into ophthalmic tissues. Therefore, some irradiation sources 120 may emit irradiation 200 with longer wavelengths to penetrate more deeply into the iris, with eventual absorption by the pigmented epithelium, to achieve secondary heating of the dilator muscle fibers 30. Accordingly, a depth of a treated tissue within the iris can be in some designs in the range of 10 microns-3,000 microns, in some designs, in the range of 500-2,000 microns.

Some irradiation sources may emit a continuous, or continuous wave (CW) irradiation 200. Others, such as lasers, or LEDs, may emit pulsed irradiation. A frequency of the pulsed irradiation 200 can be in a range of 1 Hz to 1 MHz, in some designs, in the range of 100 Hz to 100 kHz. The length of the emitted pulses can vary from 10 femtoseconds to 1 second, in some designs from 1 microsecond to 1 millisecond. The total treatment time can be in the range of 1 sec to 300 sec, in some embodiments in the range of 10 sec to 100 sec. A beam profile of the patterned irradiation 200$p$ can be a rectangular, a flat top, a smoothed, a Gaussian, or a Lorentzian profile.

An inner radius Rp(inner) of the pattern 210 can be in the range of 2-10 mm, in some designs in the range of 3-6 mm. An outer radius Rp(outer) of the pattern 210 can be in the range of 3-15 mm, in some designs, in the range of 5-10 mm The pattern 210 can be such that a treated fraction of the iris has an area that is 10-80% of the total area of the iris 11, in some design, this fraction can in the range of 20-50%.

In some embodiments, the irradiation delivery system 130 can include a pattern generator, an optical beam shaper, a patterning optics, a beam profiler, or a digitally controlled irradiation optics. Some of these elements can be built mostly from passive optical elements, such as lenses and mirrors, with some system characteristics controlled electronically, such as a telescopic distance between two lenses.

In other embodiments, the irradiation delivery system 130 can include optical elements that are actively operated and controlled by electronic or digital circuitry, as described below.

Some embodiments of the ophthalmic stimulator 100 can be configured to increase a temperature of a treatment region of the iris to a range of 45-60 degrees Celsius. Other embodiments can increase the temperature of the treatment region of the iris to a range of 50-55 degrees Celsius. As discussed in relation to FIGS. 4A-B, treatments with temperatures in these ranges have been demonstrated to impact the responsiveness of smooth muscle tissue temporarily, in a reversible and repeatable manner.

The actual effect of the heat treatment depends on several factors, since different temperatures and treatment durations can have a multitude of effects on smooth muscle cells and function. On the cellular level, first, a heat treatment can induce biochemical changes and secretions that can affect the functioning of the treated tissue, such as heat shock proteins. Second, it can cause loss of cells through various mechanisms, such as apoptosis, or programmed cell death. Finally, on a much shorter time scale, heat treatment can lead to specific loss of contractility due to denaturation of myosin molecules or inhibition of ion channels.

On a higher, physiological level, the effect of the heat treatment on the pupil may depend on factors such as dilator muscle fiber orientation, and on opposing, constrictor, muscle action. Finally, the heat treatment can change the physical properties of the muscles in different aspects as well, including shrinking or expanding the length of the muscle strands, making the strands more or less aligned, and changing of the elastic moduli of the muscles, among others.

For all these reasons, the iris of the individual patients can be analyzed by the ophthalmologist before the treatment with the ophthalmic stimulator 100. Based on the analysis, the desired medical outcomes can be cross-referenced with the patient data of the individual patients. Subsequently, the treatment region, treatment parameters and specifically the treatment temperatures can be set. As discussed further below, for some medical outcomes heating the radial dilator muscles 30 can be preferable, for others, heating the circular sphincter muscles 40 can be preferable. The treatment regions can be set according to these medical considerations.

FIGS. 6A-D illustrate that in some embodiments of the ophthalmic stimulator 100, the irradiation control system 110 can include an irradiation controller 112, an imaging system 114 and a user interface 118. The imaging system 114 can be electronically coupled to the irradiation controller 112, to relay images, image-related data, and control information. The imaging system 114 can include an image processor 114$ip$, whose functions will be described later.

Figure 6A:
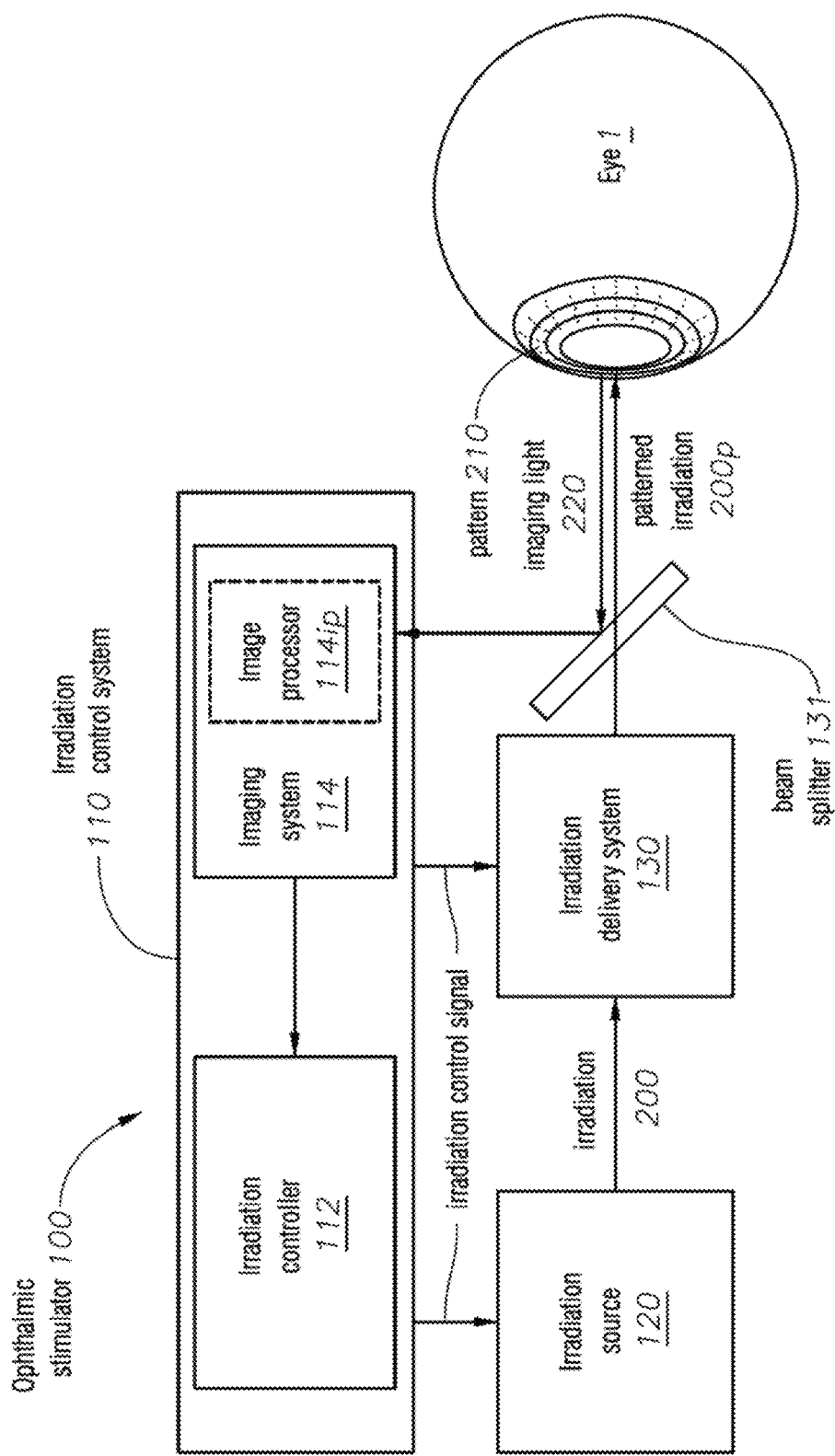
FIGS. 6A-D illustrate embodiments of the ophthalmic stimulator 100.
Figure 6B:
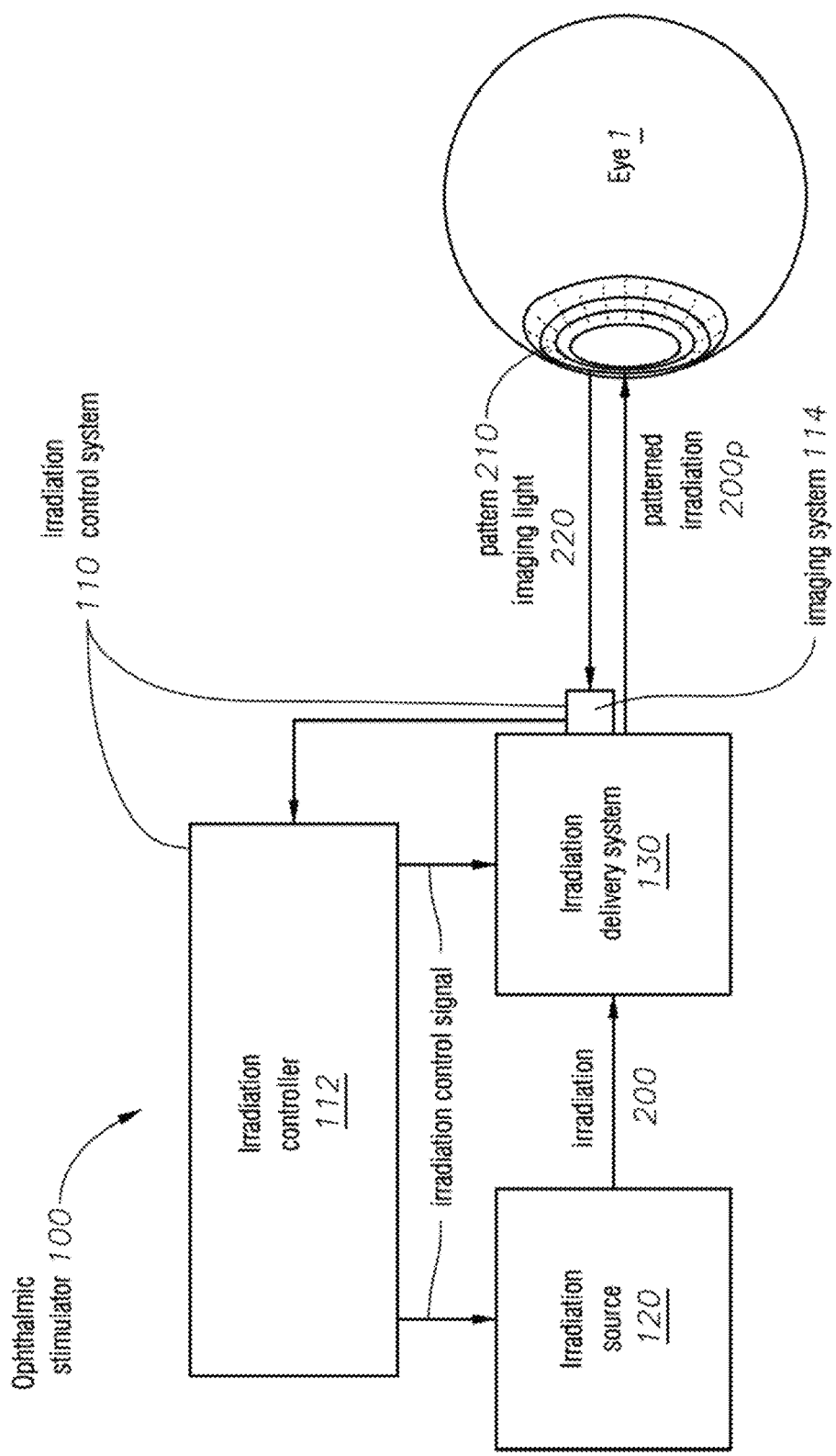

FIGS. 6A-B illustrate two implementations of the imaging system 114. In FIG. 6A, an imaging light 220 is reflected out from the optical pathway of the patterned irradiation 200$p$ by a beam splitter 131 towards the imaging system 114 that is positioned outside the irradiation optical pathway. In FIG. 6B, a small imaging system, such as a small CCD camera 114 can be placed on the distal end of the irradiation delivery system 130, directly receiving the imaging light 220. The imaging light 220 can be a reflection of an imaging light, projected on the iris 11 by an imaging light source. In other designs, the imaging light 220 can be simply the ambient light reflected from the iris 11.

The imaging system 114 can be any one of the well known ophthalmic imaging systems, including a CCD camera, feeding into a video monitor, any other electronic or digital imaging system, a video microscope, or a surgical microscope.

The irradiation control system 110 can generate the irradiation control signal by generating an image of the iris 11 of the eye with the imaging system 114 for a user, followed by receiving an image-based input from the user through the user interface 118, and generating the irradiation control signal to control the irradiation delivery system 130 to deliver the patterned irradiation 200p in accordance with the received image-based input.

In a typical example, the patterned irradiation 200p can impact the iris 11 in a ring pattern 210 with an inner radius Rp(inner) and an outer radius Rp(outer). In this embodiment, the user of the system, such as ophthalmologist, or an ophthalmic surgeon, can be prompted via the user interface 118 to enter the image-based input, which in this case can be a selection of the inner radius Rp(inner) and the outer radius Rp(outer) of the ring pattern 210, based on the surgeon analyzing the image, relayed by the imaging system 114.

Figure 12A:
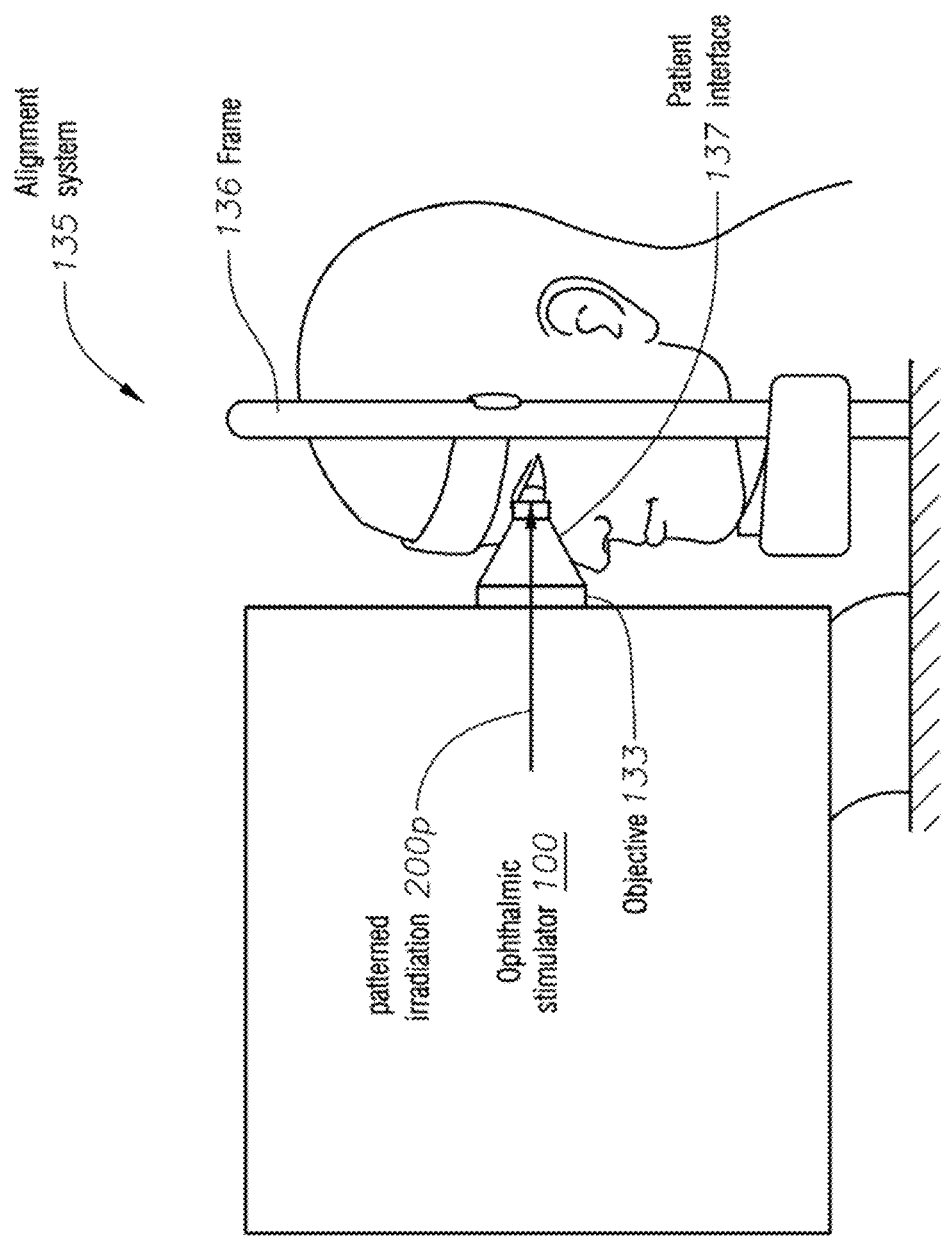
FIGS. 12A-E illustrate embodiments of the alignment system 135.
Figure 12B:
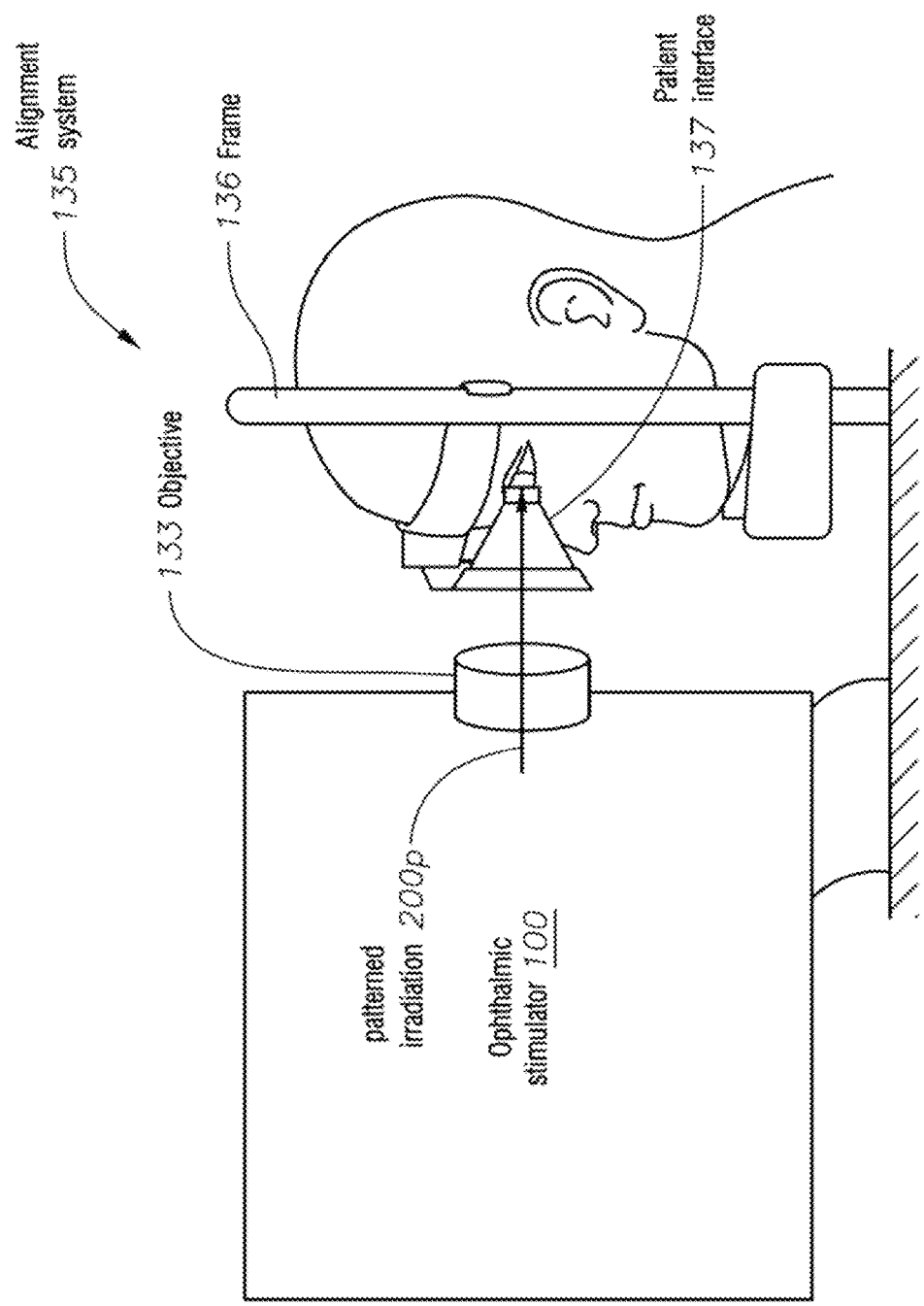
Figure 12C:
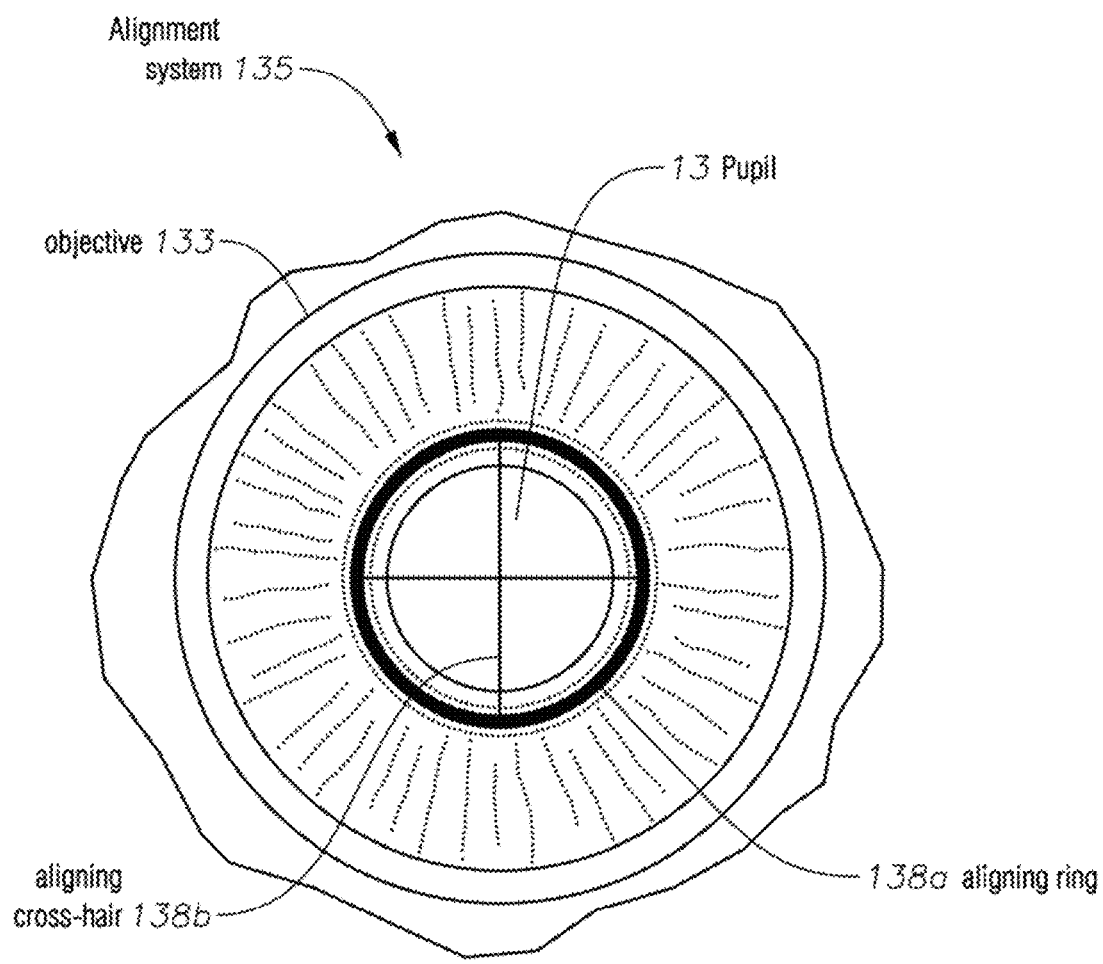
Figure 12D:
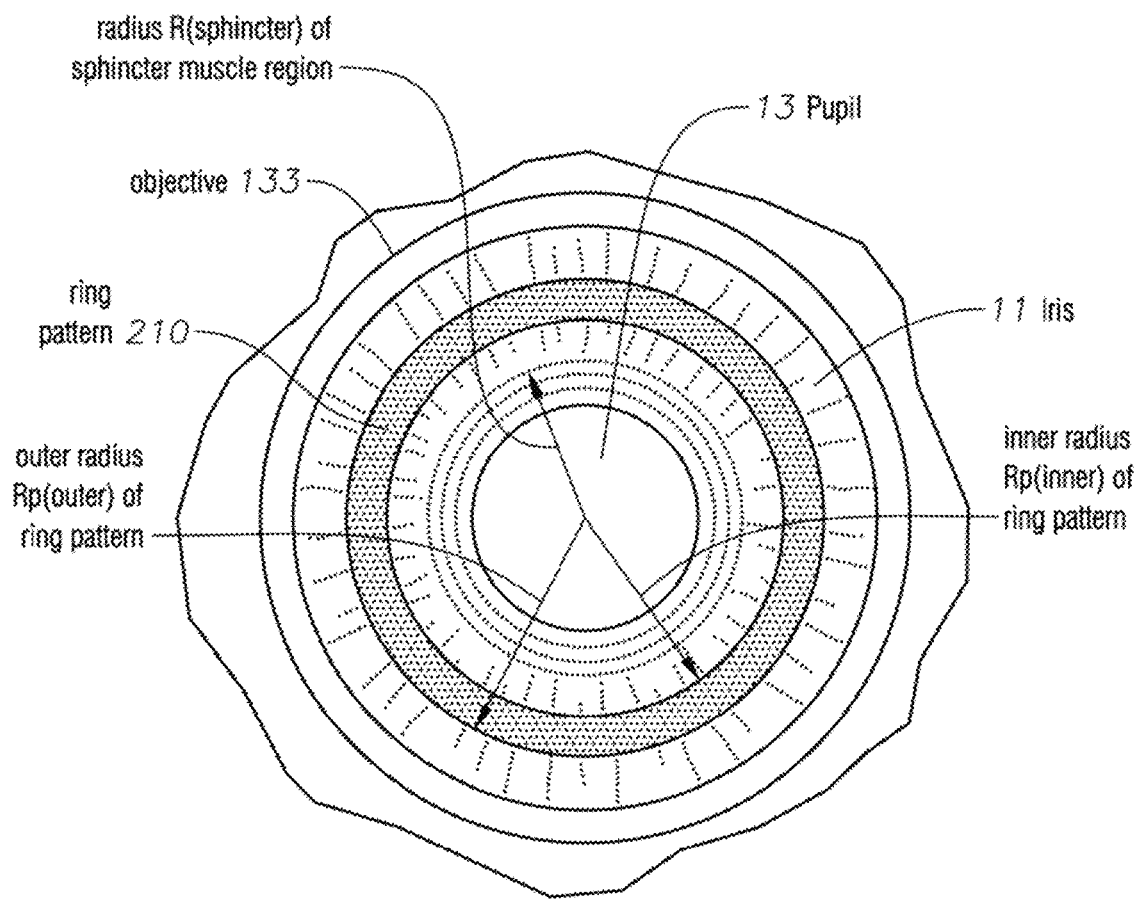
Figure 12E:
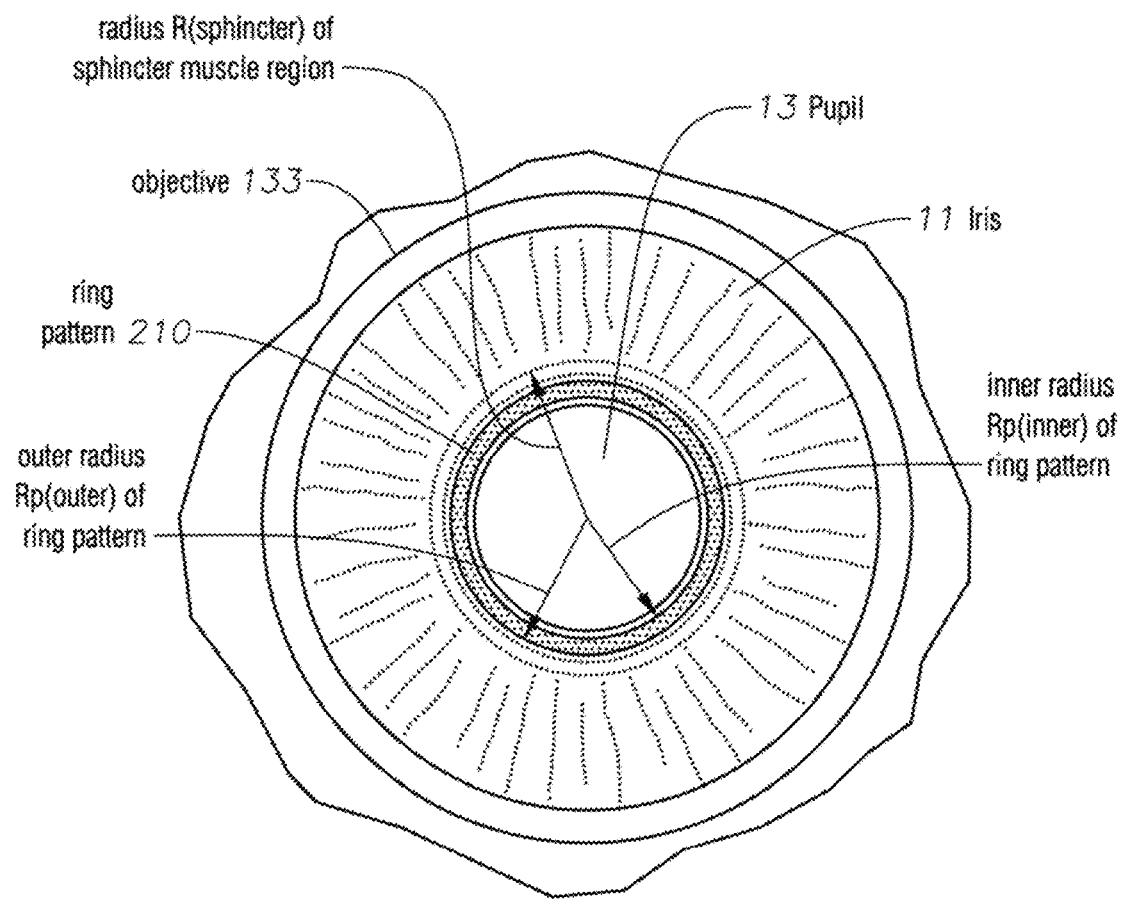

FIGS. 12D-E illustrate that setting these radii Rp(inner) and Rp(outer) determines whether the ring pattern 210, and thus the treatment region, is the region of the radial dilator muscles 30, or the circular sphincter muscles 40. Denoting the outer radius of the sphincter muscles with R(sphincter), if the surgeon selects the inner radius Rp(inner) of the ring pattern 210 to be greater than R(sphincter): Rp(inner)>R(sphincter), then the ring pattern 210 will fall on the radial dilator muscles 30, and those muscles will receive the heat treatment. Whereas, if the surgeon selects the outer radius Rp(outer) of the ring pattern 210 to be smaller than R(sphincter): Rp(outer)<R(sphincter), then the ring pattern 210 will fill on the circular sphincter muscles 40, and the circular sphincter muscles 40 will be treated by the patterned irradiation 200p. As discussed, an ophthalmologist can select either treatment region based on a prior analysis of the patient's specific data, and the desired medical outcomes.

In some embodiments, the irradiation control system 110 can include an image processor 114ip in the imaging system 114. The image processor 114ip can be integrated with the imaging system 114, can be partially integrated, or can be a separate electronic or computational system. In these embodiments, the irradiation control system 110 can generate the irradiation control signal by generating an image of the iris 11 with the imaging system 114 for the image processor 114ip, receiving an image-based input from the image processor 114ip, and generating the irradiation control signal to control the irradiation delivery system 130 to deliver the patterned irradiation 200p in accordance with the received image-based input.

In a representative embodiment, the patterned irradiation 200p can impact the iris 11 in a ring pattern 210 with inner and outer radii Rp(inner) and Rp(outer). The imaging system 114 can image the iris 11, and relay this image to the image processor 114ip, in response, the image processor 114ip can run an image recognition program, possibly including an edge-recognition software, and identify the inner and outer radii of the iris 11, and the radius R(sphincter) that demarcates the radial dilator muscles 30 from the circular sphincter muscles 40. Then, the image processor 114ip can generate the image-based input that sets, or suggests to set, the Rp(inner) and Rp(outer) radii of the ring pattern 210. The effect of these choices on the treatment region and the corresponding medical effects have been explained earlier.

FIG. 12A-C illustrate that in some embodiments of the ophthalmic stimulator 100, the irradiation control system 110 can include an alignment system 135.

FIG. 12A illustrates that in some embodiments the ophthalmic stimulator 100 can include an objective 133, the last optical element that guides the patterned irradiation 200p toward the eye 1. In these embodiments, the alignment system 135 can include a frame, or chin-rest 136, on which the patient can rest her/his chin to minimize the motion of the eye 1 relative to the stimulator 100. The alignment system 135 can also include a patient interface 137 that contacts the eye 1 of the patient. Many types of patient interfaces 137 are known in the art and can be used here. FIG. 12A illustrates a patient interface 137, whose proximal end is attached to the objective 133 of the ophthalmic stimulator 100, and whose distal end the patient presses her eyes against. The patient interface 137 can ensure a firm coupling, or docking, to the eye by involving a vacuum suction system, or a forceps. The patient interface 137 can be a one-piece or a two-piece patient interface. The distal end of the patient interface 137 can include a contact lens, to ensure a smoother, softer connection to the eye. Such a contact lens also minimizes the optical distortions of the patterned irradiation 200p as it exits the patient interface 137 and enters the cornea 5 of the eye 1.

FIG. 12B illustrates another embodiment of the alignment system 135, where the patient interface 137 is coupled to the frame 136 instead of the stimulator 100. Since the frame 136 is rigidly coupled to the ophthalmic stimulator 100, the optical pathway of the patterned light 200p is similarly secure from the objective to the eye 1 in this embodiment as well. One of the differences is that there is a distance between the stimulator 100 and the patient interface, 137, so the patient does not have to lean forward to receive the treatment, and the doctor sees where the patterned light 200p hits the patient interface 137. As before, this patient interface 137 can also be a one-piece and a two-piece patient interface 137.

The patient interfaces 137 of either FIG. 12A or 12B is preferably aligned and centered with the eye 1 before coupling, or docking them to the eye 1. FIG. 12C illustrates a corresponding aligning, or centering, pattern 138 of the alignment system 135. This centering pattern, or aligning pattern, can include an aligning ring 138a, or an aligning cross-hair 138b, or both. This aligning pattern 138 can be formed in, projected into, or digitally overlaid, the image formed by the imaging system 114, in a position that is concentric with the optical axis of the objective 133. The ophthalmic surgeon, or any other user or operator, can dock the patient interface 137 of the stimulator 100 to the eye with increased precision, with aligning, or centering, the aligning element 138 with the pupil 13 during the docking procedure.

In a video-monitor-based embodiment, the surgeon can make the centering of the aligning ring 138a on the video image with the edge of the pupil 13 part of the docking. During the docking, the surgeon can instruct the patient to move her/his head and eye around, until the circular edge of the pupil 13 is concentric with the aligning ring 138a. Then the surgeon can complete the docking of the patient interface 137 to the eye 1. Further embodiments of the alignment system 135 will be described later.

In some designs, the stimulator 100 can include a fixation light 202, and the surgeon can instruct the patient to stare at the fixation light 202 during docking. The patient staring, or fixating at the fixation light 202 can further help centering the patient interface 137 with the pupil 13 during the docking.

In these embodiments, the irradiation control system 110 can generate the irradiation control signal by processing alignment data with the alignment system 135, and generating the irradiation control signal to control the irradiation delivery system 130 to deliver the patterned irradiation 200p to the iris in a pattern 210 aligned with the pupil 13 of the eye.

In some embodiments of the ophthalmic stimulator 100, the processing alignment data can include generating an image of the iris 11 with the imaging system 114, and overlaying an alignment pattern 138 on the generated image. The generating the irradiation control signal can include generating a misalignment-warning signal, or generating an alignment-guidance signal, if a misalignment is detected during the processing of the alignment data that is part of the docking. The misalignment-warning signal can alert the operating surgeon to instruct the patient to move his/her head, eye, or both to improve the alignment to help making the docking precise. Also, for stimulator designs where the stimulator 100 or the patient interface 137 itself can be moved or adjusted, the misalignment-warning signal can alert the surgeon for the need to adjust the stimulator 100 or the patient interface 137.

An example for an adjustable patient interface 137 is a two-piece patient interface 137, where one piece of the patient interface 137 can be attached to the stimulator 100 at its objective 133, the other piece of the patient interface 137 can be coupled to the eye with vacuum-suction, or pressing, and the docking includes the surgeon maneuvering the two pieces of the patient interface 137 to dock to each other.

Figure 6C:
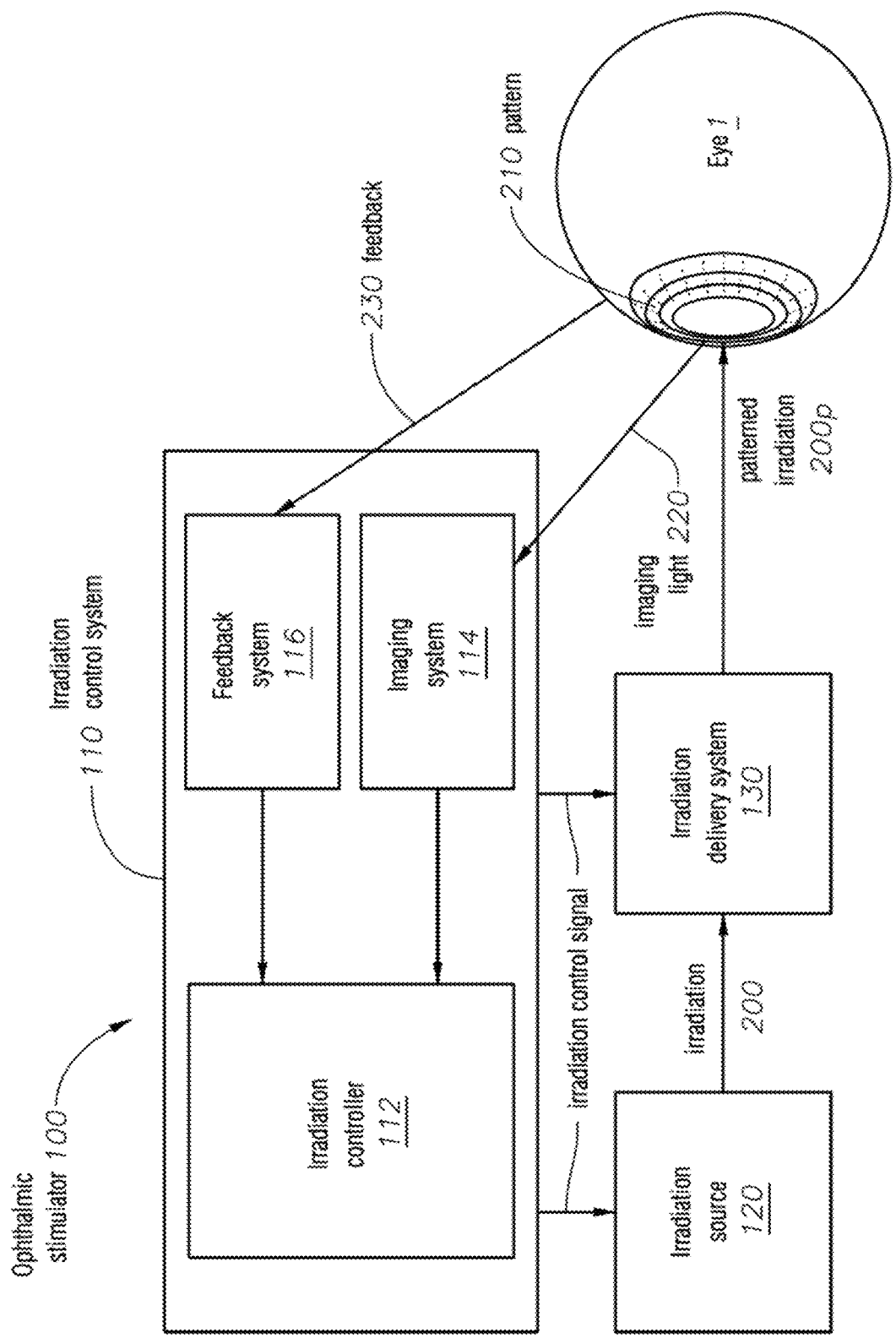
Figure 6D:
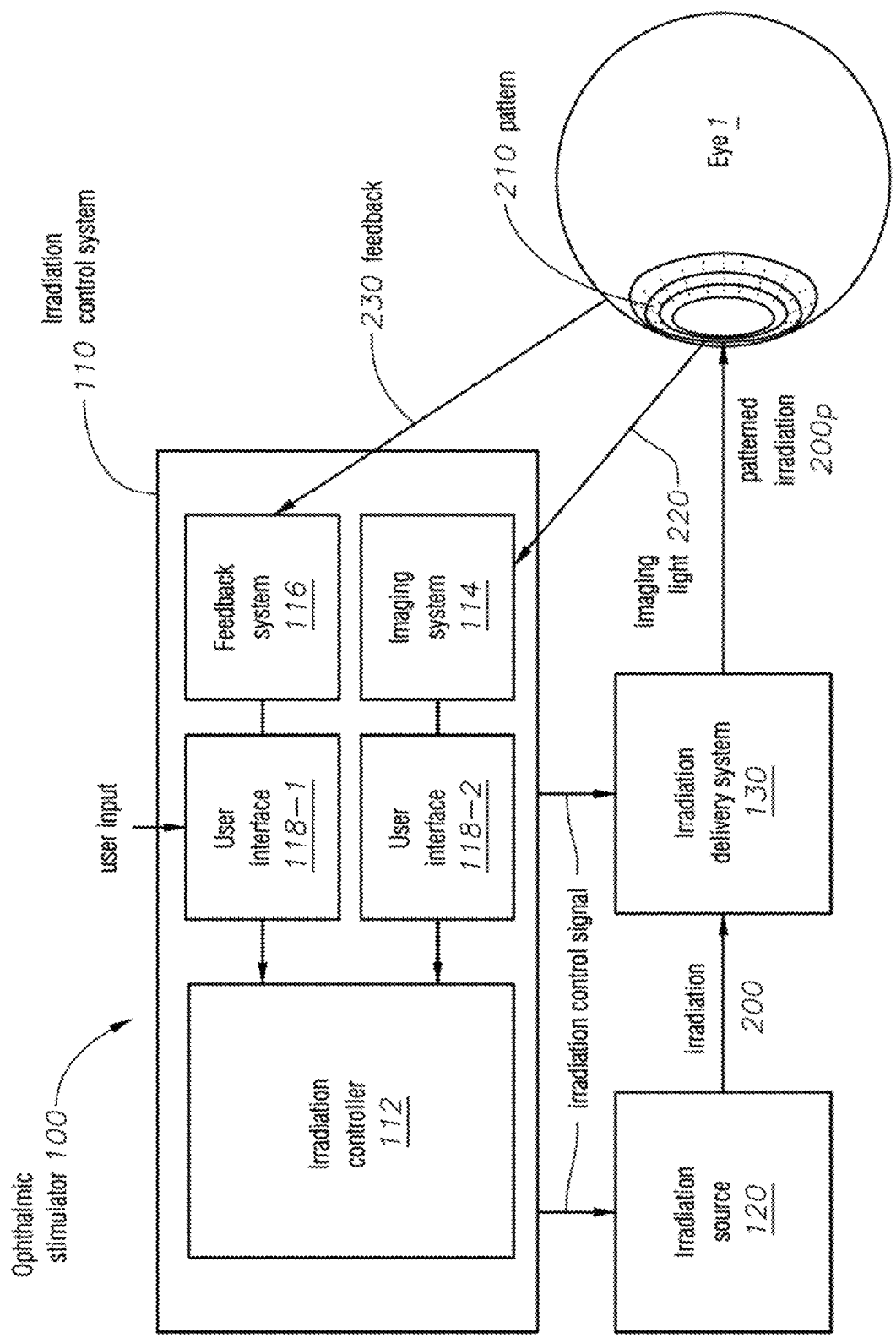

FIGS. 6C-D also show a feedback system 116. This system will be described in detail below.

Figure 10:
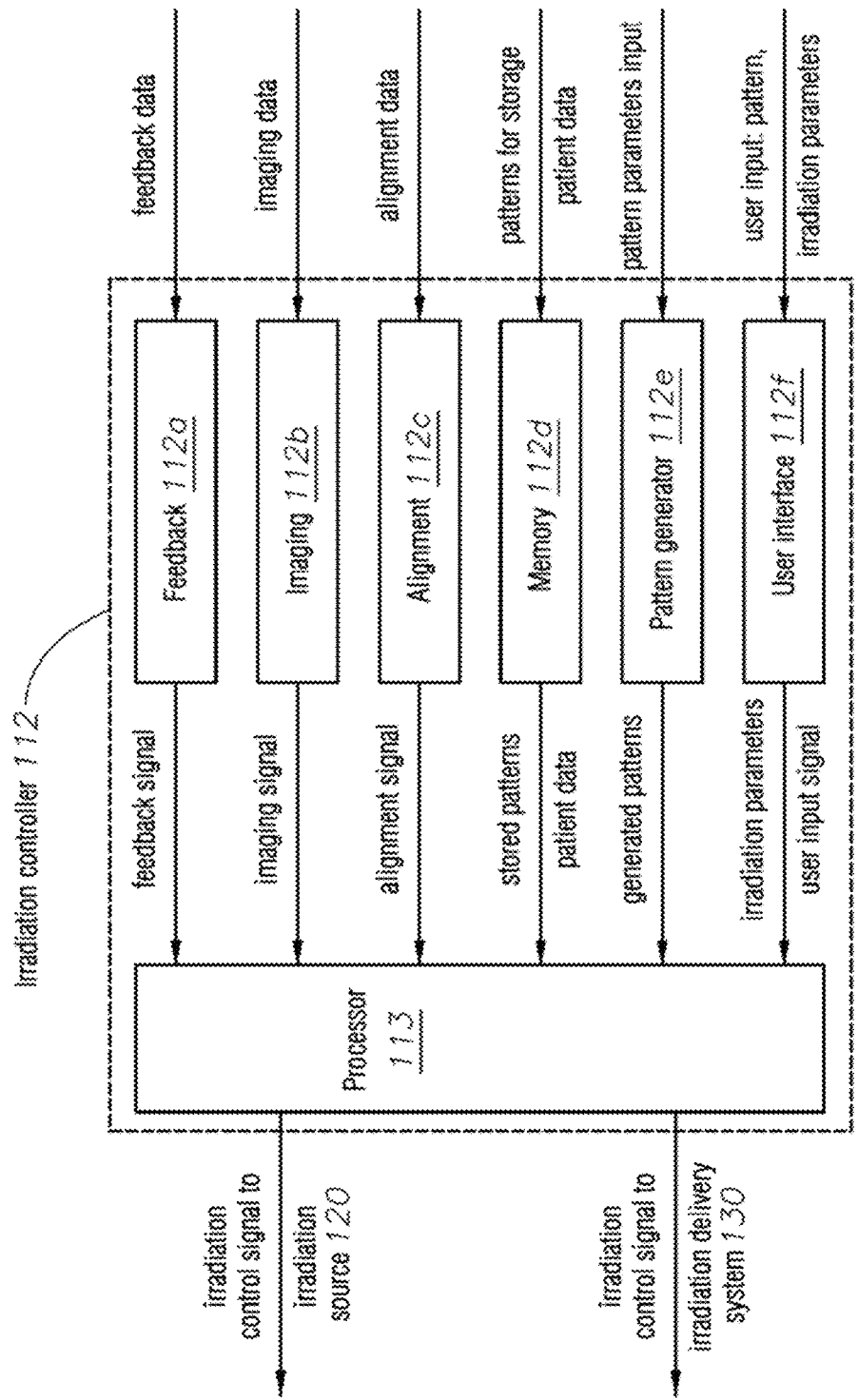
FIG. 10 illustrates an irradiation controller 112.

FIG. 10 illustrates that the irradiation controller 112 can include a number of blocks. These blocks can be implemented as a dedicated processor or circuitry, or can be implemented as a software, code, program, or application, implemented on a computer of the irradiation controller 112, or a combination of hardware and software blocks. In various embodiments, the irradiation controller 112 can include:
- a feedback block 112a, to receive feedback data and to send a feedback signal to a processor 113;
- an imaging block 112b, to receive imaging data and to send an imaging signal to the processor 113;
- an alignment block 112c, to receive alignment data and to send an alignment signal to the processor 113;
- a memory block 112d, to receive patterns for storage and patient data, to store algorithms and codes, and to send stored patterns, patient data, or executable algorithms to the processor 113;
- a pattern generator block 112e, to receive pattern parameters and to send generated patterns to the processor 113;
- a user interface block 112f, to receive a user input, for example through a user interface 118, that can be patterns, commands, and irradiation parameters, and to send the received patterns, commands and irradiation data as a user input signal to the processor 113.

Each of these blocks can receive, their input from corresponding hardware blocks, such as sensors, controllers, hardware blocks and user interfaces. For example, the feedback block 112a can be a dedicated circuitry that receives the feedback data from the feedback system 116, as described below. The imaging block 112b can be a software algorithm, implemented on a processor that receives the imaging data from the imaging system 114 that can include a CCD camera, a video monitor, or a surgical microscope.

In response to signals, received from any of the blocks 112a-f, the processor 113 can send an irradiation control signal to the irradiation source 120, or to the irradiation delivery system 130, or to both.

In some detail, in embodiments of the ophthalmic stimulator 100 the irradiation control system 110 can include the memory 112d, and the generating the irradiation control signal can include recalling stored data from the memory 112d, representing at least one of an irradiation pattern and patient data, and generating the irradiation control signal to control the irradiation delivery system 130 to deliver the patterned irradiation 200p to the iris 11 in accordance with the recalled stored data.

In embodiments, the irradiation control system 110 can include a pattern generator; and the generating the irradiation control signal can include generating an electronic representation of the irradiation pattern 210; and generating the irradiation control signal to control the irradiation delivery system 130 to deliver the patterned irradiation 200p with the generated irradiation pattern 210.

Returning to the medial effects and treatments, embodiments of the ophthalmic stimulator 100 can cause a temporary constriction of the pupil 13 of the eye that includes an at least 5% reduction of a radius of the pupil 13 that lasts less than one hour. In some cases, the reduction of the radius of the pupil can last for a time interval more than one hour and less than one day. In other embodiments, the temporary constriction of the pupil of the eye includes an at least 5% reduction of the radius of the pupil that lasts for a time interval between one day and one week; or between one week and one month; or between one month and three months; or between three months and one year.

Each of these time intervals has their own medical and patient advantages. The longer the pupil constriction lasts, the less often the treatment may need to be applied, which can be preferred by patients. Also, the overall paradigm of use of the ophthalmic stimulator 100 depends on the duration of the constriction. Stimulators that constrict a pupil for a month or longer can be deployed in the offices of ophthalmologists, and patients can schedule regular visits for re-constriction treatments on a monthly basis. Stimulators that constrict the pupil for a day or longer could be tabletop systems that the individual patients buy, or lease, and they self-administer the treatment, for example, as part of a daily routine. Finally, stimulators that constrict the pupil for an hour, or for a few hours, can be mobile systems which the patient can carry with themselves and apply the treatment on demand. Obviously, stimulators operated by untrained patients have to have much more robust safety, monitoring and control systems to prevent undesirable medical outcomes. In sum, embodiments that constrict the pupil for different time intervals can offer very different medical outcomes, may be operated by very different personnel, and may need very different safety, monitoring and control systems.

Figure 11A:
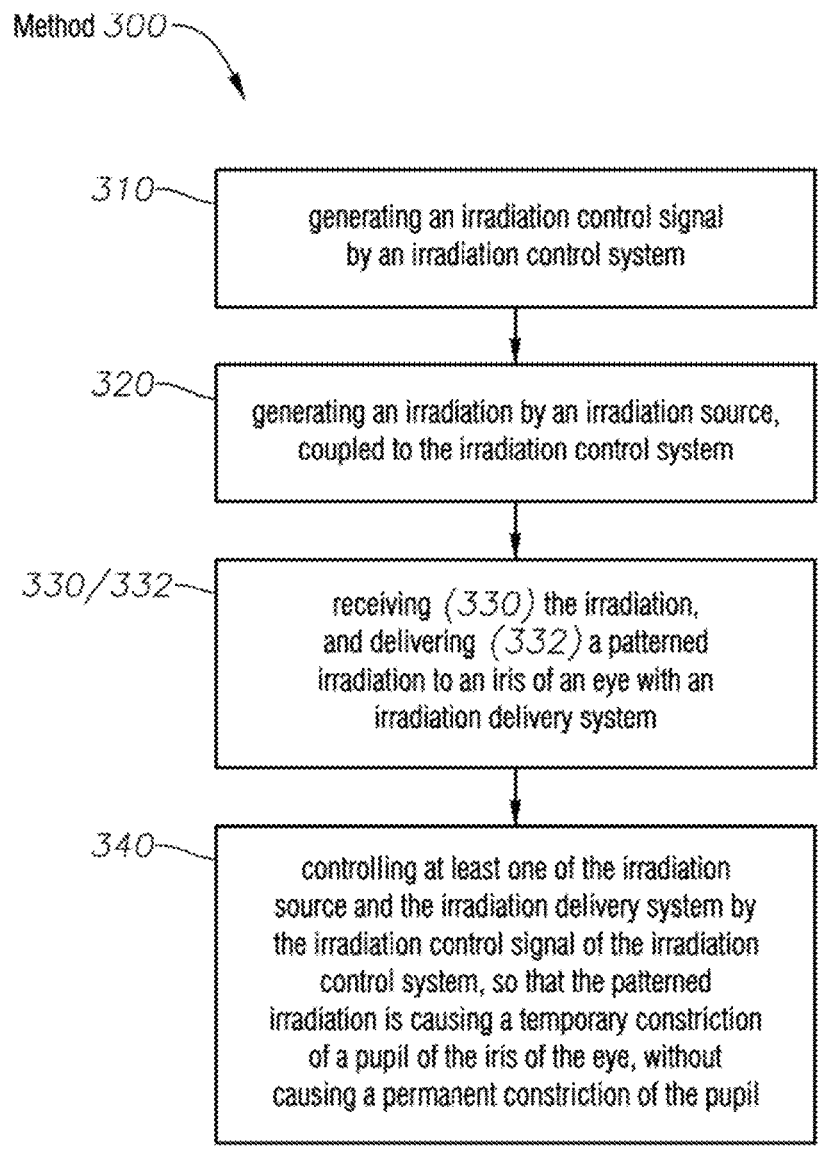
FIGS. 11A-D illustrate steps of the methods 300, 300', 302, and 304.

FIG. 11A illustrates embodiments of a method 300, related for the preceding description, for temporarily constricting a pupil 13 of an eye by an ophthalmic stimulator 100. The method 300 includes the following steps:
- generating 310 an irradiation control signal by an irradiation control system 110;
- generating 320 an irradiation 200 by an irradiation source 120, coupled to the irradiation control system 110;
- receiving 330 the irradiation 200, and delivering 332 a patterned irradiation 200p to an iris 11 of the eye with an irradiation delivery system 130; and
- controlling 340 at least one of the irradiation source 120 and the irradiation delivery system 130 by the irradiation control signal of the irradiation control system 110 so that the patterned irradiation is causing a temporary constriction of the pupil of the eye, without causing a permanent constriction of the pupil.

In embodiments, the generating 320 the irradiation 200 can include generating a light beam, an electromagnetic irradiation, a LED light, a narrow-band light, a broad-band light, an infrared beam, an incoherent light, a radio-frequency beam, or a sound by the irradiation source 120. Another class of irradiation sources 120 can include a coherent light source, a laser beam, a continuous wave laser beam, or a pulsed laser beam. Marked differences between the preceding incoherent irradiation sources and the just-listed coherent and laser sources will be discussed below.

The delivering 332 of the patterned irradiation 200$p$ can include patterning the irradiation 200 by at least one of a pattern generator 112$e$, an optical beam shaper 132, a patterning optics, a beam profiler, a beam scanner 134, and a digitally controlled irradiation optics.

In embodiments, the causing the temporary constriction of the pupil can include increasing a temperature of a treatment region of the iris to a range of 45-60 degrees Celsius. In some embodiments, the temperature of the treatment region of the iris can be raised into a range of 50-55 degrees Celsius.

FIG. 10 illustrates, that in some embodiments of the method 300, the irradiation control system 110 can include an imaging system 114, in some cases with a corresponding imaging block 112$b$ in the irradiation controller 112, and a user interface 118, in some cases with a corresponding user interface block 112$f$ in the irradiation controller 112. In these embodiments, the generating 310 of the irradiation control signal can include generating an image of the iris 11 of the eye with the imaging system 114 for a user, receiving an image-based input from the user through the user interface 118, and generating the irradiation control signal to control the irradiation delivery system 130 to deliver the patterned irradiation 200$p$ in accordance with the received input. In embodiments, the patterned irradiation 200$p$ can impact the iris in a ring pattern 210; and the image-based input can be an inner radius Rp(inner) and an outer radius Rp(outer) of the ring pattern 210, selected by the user.

In some embodiments of the method 300, the irradiation control system 110 can include an imaging system 114, and an image processor 114$ip$, in some cases implemented in the imaging block 112$b$ of the irradiation controller 112. The generating 310 of the irradiation control signal can include generating an image of the iris of the eye with the imaging system 114 for the image processor 114$ip$; processing the image of the iris and generating an image-based input by the image processor 114$ip$; receiving the image-based input from the image processor 114$ip$; and generating 310 the irradiation control signal to control the irradiation delivery system 130 to deliver the patterned irradiation 200$p$ in accordance with the received image-based input. In some designs, the patterned irradiation 200$p$ can impact the iris 11 in a ring pattern 210; and the image-based input can be an inner radius Rp(inner) and an outer radius Rp(outer) of the ring pattern.

In some embodiments of the method 300, the irradiation control system 110 can include an alignment system 135, in some cases with its alignment block 112$c$ in the irradiation controller 112; and the generating 310 of the irradiation control signal can include processing alignment data with the alignment system 135, and generating the irradiation control signal to control the irradiation delivery system 130 to deliver the patterned irradiation 200$p$ to the iris in a pattern 210 aligned with the pupil 13 of the iris 11.

In some embodiments of the method 300, the processing alignment data can include generating an image of the iris with an imaging system 114, and overlaying an alignment pattern 138 on the image, in some cases with the alignment block 112$c$, or with the image processor 114$ip$; and the generating 310 the irradiation control signal can include generating a misalignment warning signal, or generating an alignment-guidance signal.

In some embodiments, the irradiation control system 110 can include a memory block 112$d$; and the generating the irradiation control signal 310 can include recalling stored data from the memory block 112$d$, representing at least one of an irradiation pattern 210 and patient data; and generating 310 the irradiation control signal to control the irradiation delivery system 130 to deliver the patterned irradiation 200$p$ to the iris 11 in accordance with the recalled stored data. In some designs, the irradiation control system can include the pattern generator 112$e$; and the generating 310 of the irradiation control signal can include generating the irradiation pattern 210; and generating the irradiation control signal to control the irradiation delivery system 130 to deliver the patterned irradiation 200$p$ with the generated irradiation pattern 210.

Some embodiments of the method 300 can include acquiring and analyzing patient data; selecting a treatment region based on the analyzing of the patient data; and delivering the patterned irradiation 200$p$ to the selected treatment region. A notable embodiment of this step is the ophthalmologist analyzing patient data and deciding whether the treatment radiation shall be applied to the radial dilator muscles 30, or to the circular sphincter muscles 40. This analysis and decision can involve selecting the appropriate treatment parameters among the large number of treatment parameters described previously.

In some cases, the selecting the treatment region can include selecting a ring pattern 210$r$ with an inner radius Rp(inner) larger than R(sphincter), a radius of a region of the circular sphincter muscles 40.

In some cases, the selecting the treatment region can include selecting a ring pattern 210$r$ with an outer radius Rp(outer) smaller than R(sphincter), the radius of a region of the circular sphincter muscles 40.

Some embodiments of the method 300 can include controlling the irradiation source 120, or the irradiation delivery system 130, or both, so that the patterned irradiation 200$p$ is causing a temporary constriction of the pupil of the eye that includes an at least 5% reduction of a radius of the pupil that lasts less than one hour.

In some cases, the temporary constriction of the pupil can last between one hour and one day. In some cases, the temporary constriction of the pupil can last between one day and one week; in some cases between one week and one month; in some cases between one month and three months; and in some cases between three months and one year. The medical, patient, implementation, and safety differences between embodiments involving temporary constrictions of different duration have been discussed earlier.

The ophthalmic stimulators 100 described up to now shared a common trait: they caused a temporary constriction of the pupil.

Figure 5B:
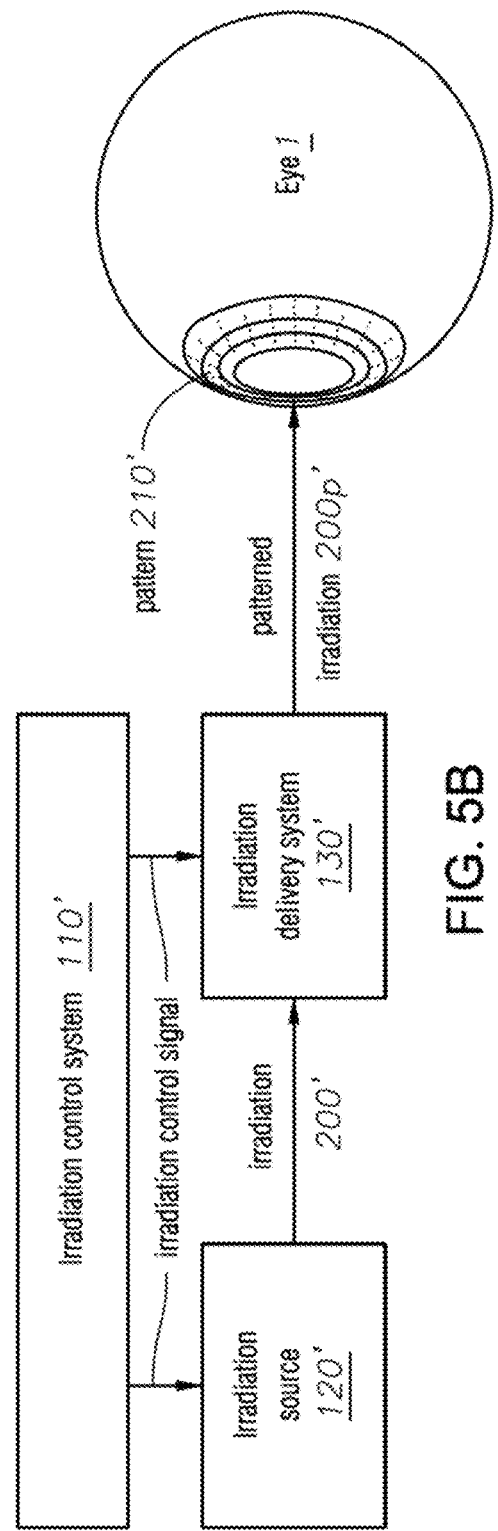

FIG. 5B illustrates a distinct class of permanent ophthalmic stimulators 100' that can cause a long-term, or even a permanent constriction of the pupil. These ophthalmic stimulators 100' share some of the major engineering elements with the temporary constriction stimulators 100, but have different medical modes of action, different irradiation sources, and stronger safety systems, among others.

In some embodiments, an ophthalmic stimulator 100' for constricting a pupil of an eye can include an irradiation control system 110', to generate an irradiation control signal; an irradiation source 120', coupled to the irradiation control system 110', to generate an irradiation 200'; and an irradiation delivery system 130', coupled to the irradiation control system 110', to receive the irradiation 200' from the irradiation source 120', and to deliver a patterned irradiation 200p' to the iris 11 of the eye 1; wherein the irradiation control system 110' controls the irradiation source 120', or the irradiation delivery system 130', or both, with the irradiation control signal so that the patterned irradiation 200p' causes a long-term constriction of the pupil of the eye.

In a class of the ophthalmic stimulator 100', the irradiation source 120' can include an incoherent light source, such as a lamp, a LED, an infrared light source, a radiofrequency source, an electromagnetic source and a sound source. In another class, the irradiation source 120' can include a coherent light source, such as laser, a pulsed laser and a continuous wave laser. There are substantial differences between irradiation sources that employ incoherent light sources and those that employ coherent light sources, as discussed above.

In some embodiments, the irradiation delivery system 130' can include an optical beam shaper and a patterning optics.

In some embodiments, the ophthalmic stimulator 100' can be configured to increase a temperature of a treatment region of the iris to a range of 50-80 degrees Celsius. In some embodiments, the ophthalmic stimulator 100' can be configured to increase a temperature of the treatment region of the iris to a range of 55-70 degrees Celsius.

Some embodiments of the ophthalmic stimulator 100' can cause a long-term constriction of the pupil that lasts longer than a year. In some cases, the ophthalmic stimulator 100' can be designed to cause an irreversible change in the iris of the eye. This long-term, or permanent, change can be a change of the length, or spatial extent, of the treated muscle tissue. In other cases, it can be a reduced, or enhanced, elasticity, or flexibility. In some cases, it can be an altered stiffness. In some cases, it can be an altered reactivity to stimuli.

The ophthalmic stimulator 100' achieves the long-term reduction of constriction of the pupil by applying the irradiation 200' with treatment parameters critically different from the ones used by the temporary stimulator 100. The critical difference can be one of many factors that cause permanent, or long-term constriction of the pupil, including the followings. Beams with wavelength short enough to cause permanent change. Beams with intensity per area high enough to cause long-term change. Beams with total deposited energy high enough to cause permanent change. Beams with treatment times long enough to cause permanent change. Beams with beam pulses long enough, and frequencies high enough to cause permanent change. Which specific parameters are sufficient to make the change permanent is patient specific and is selected by the surgeon.

In some embodiments, the irradiation control system 110' can include an imaging system 114' and a user interface 118'. In these embodiments, the irradiation control system 110' can, generate the irradiation control signal by generating an image of the iris of the eye with the imaging system 114' for a user, receiving an image-based input from the user through the user interface 118', and generating the irradiation control signal to control the irradiation delivery system 130' to deliver the patterned irradiation 200p' in accordance with the received input.

Some of the engineering details of the permanent ophthalmic stimulator 100' are analogous to that of the temporary ophthalmic stimulator 100'. To contain the length of this document, some of these details of the stimulator 100' will not be provided with their own figures, but the corresponding figures in the description of the stimulator 100 will be referenced, with the understanding that those need to be modified to cause a long term, not temporary constriction of the pupil.

In some embodiments of the ophthalmic stimulator 100', the irradiation control system 110' can include an alignment system 135'; and the irradiation control system 110' can generate the irradiation control signal by processing alignment data with the alignment system 135', and generating the irradiation control signal to control the irradiation delivery system 130' to deliver the patterned irradiation 200p' to the iris in a pattern 210, aligned with a pupil 13 of the iris 11.

Figure 11B:
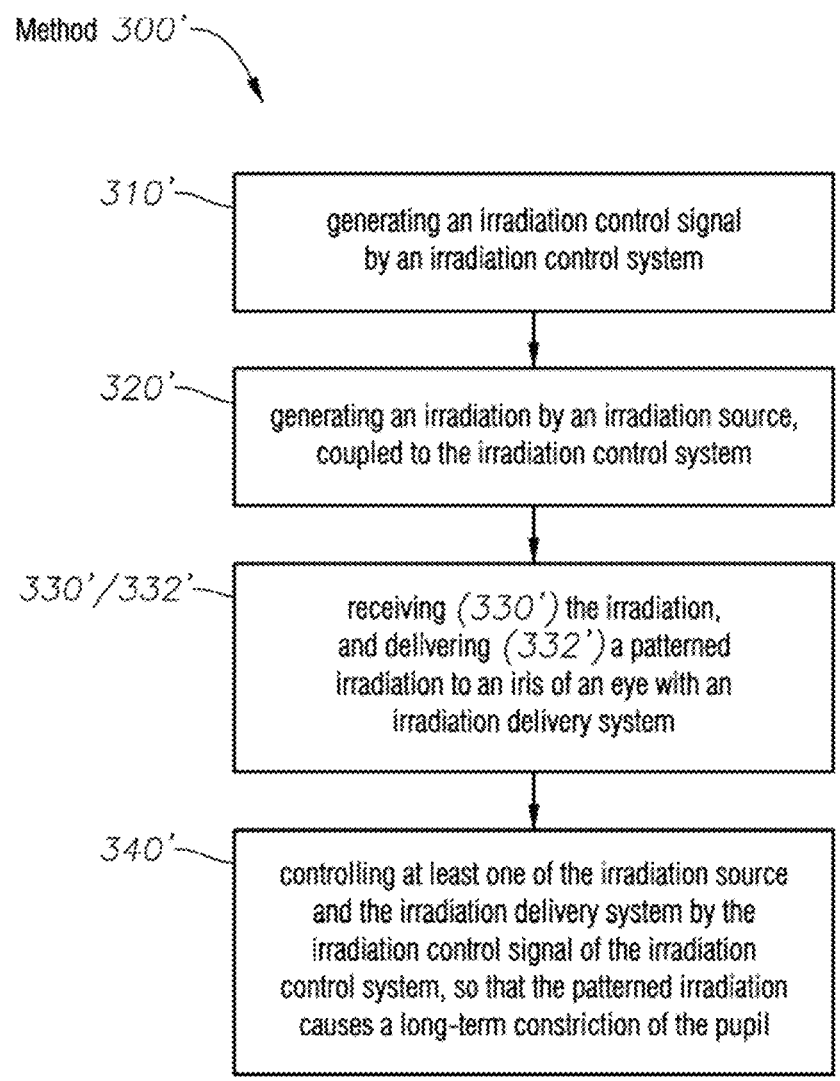

FIG. 11B illustrates a related method 300' for causing a long-term constriction of a pupil of an eye by the ophthalmic stimulator 100'. The method 300' can include the following steps:

generating 310' an irradiation control signal by an irradiation control system 110';

generating 320' an irradiation by an irradiation source 120', coupled to the irradiation control system 110';

receiving 330' the irradiation and delivering 332' a patterned irradiation to an iris of the eye with an irradiation delivery system 130'; and controlling 340' at least one of the irradiation source 120' and the irradiation delivery system 130' by the irradiation control signal of the irradiation control system 110' so that the patterned irradiation causes a long-term constriction of the pupil of the eye.

In the method 300', the causing the long-term constriction of the pupil can include increasing a temperature of a treatment region of the iris to a range of 50-80 degrees Celsius. In some cases, the method 300' can include increasing a temperature of the treatment region of the iris to a range of 55-70 degrees Celsius. While these ranges have some overlap with temperature ranges described in relation to the temporary stimulator 100, for a particular patient the temperature range where the constriction is temporary can be quite well separated from the temperature range, where the constriction is permanent. For example, for a particular patient, temperatures in the range of 50-55 C may constrict the pupil for a day or less; temperatures in the 55-60 C range may cause the pupil to constrict for a time between a week and a month, temperatures in the 60-65 C range can cause the pupil to constrict for a time between a month and a year, and temperatures in the 65-70 C range may cause the pupil to constrict for a time longer than a year. These long-term changes can very well be associated with an irreversible change in the iris of the eye.

As before, in some embodiments of the method 300' the irradiation control system 110' can include an imaging system 114 and a user interlace 118; and the generating the irradiation control signal can include generating an image of the iris of the eye with the imaging system 114 for a user, receiving an image-based input from the user through the user interface 118, and generating the irradiation control signal to control the irradiation delivery system 130' to deliver the patterned irradiation 200p' in accordance with the received input.

In some embodiments of the method 300', the irradiation control system 110' can include an alignment system 135; and the generating the irradiation control signal can include processing alignment data with the alignment system 135, and generating the irradiation control signal to control the irradiation delivery system 130' to deliver the patterned irradiation 200p' to the iris in a pattern 210 aligned with a pupil of the iris.

As discussed, the ophthalmologist operating the stimulator 100' can analyze several factors when practicing the method 300'. The analysis can include the determination what treatment parameters to use to achieve a long-term or permanent constriction change, to go beyond the previously described temporal changes. The analysis can also be focused at which treatment regions to irradiate. As discussed before, some vision-improvement goals can be better achieved by heat-treating the radial dilator muscles 30, others by heat-treating the circular sphincter muscles 40.

Both of these analyses can involve acquiring and analyzing patient data. In a typical example, a patient may have used the temporary ophthalmic stimulator 100 by practicing the method 300 repeatedly and for an extended period, and may have grown comfortable with its effect to the degree that she/he decided to make the constriction of the pupil permanent. During these preceding temporary treatments, the irradiation controller 110 of the stimulator 100, or its operator may have acquired and collected a substantial amount of data about the particular patient. An ophthalmologist, who is planning administering a higher energy irradiation by practicing the method 300' with a permanent ophthalmic stimulator 100' to permanently change the constriction of the pupil, may evaluate and analyze the data that was collected during the previous, repeated temporary constrictions of the pupil of this particular patient. This analysis can be followed by selecting a treatment region based on the analyzing of the patient data; and delivering the patterned irradiation 200p' to the selected treatment region to cause the long-term constriction of the pupil.

Figure 7A:
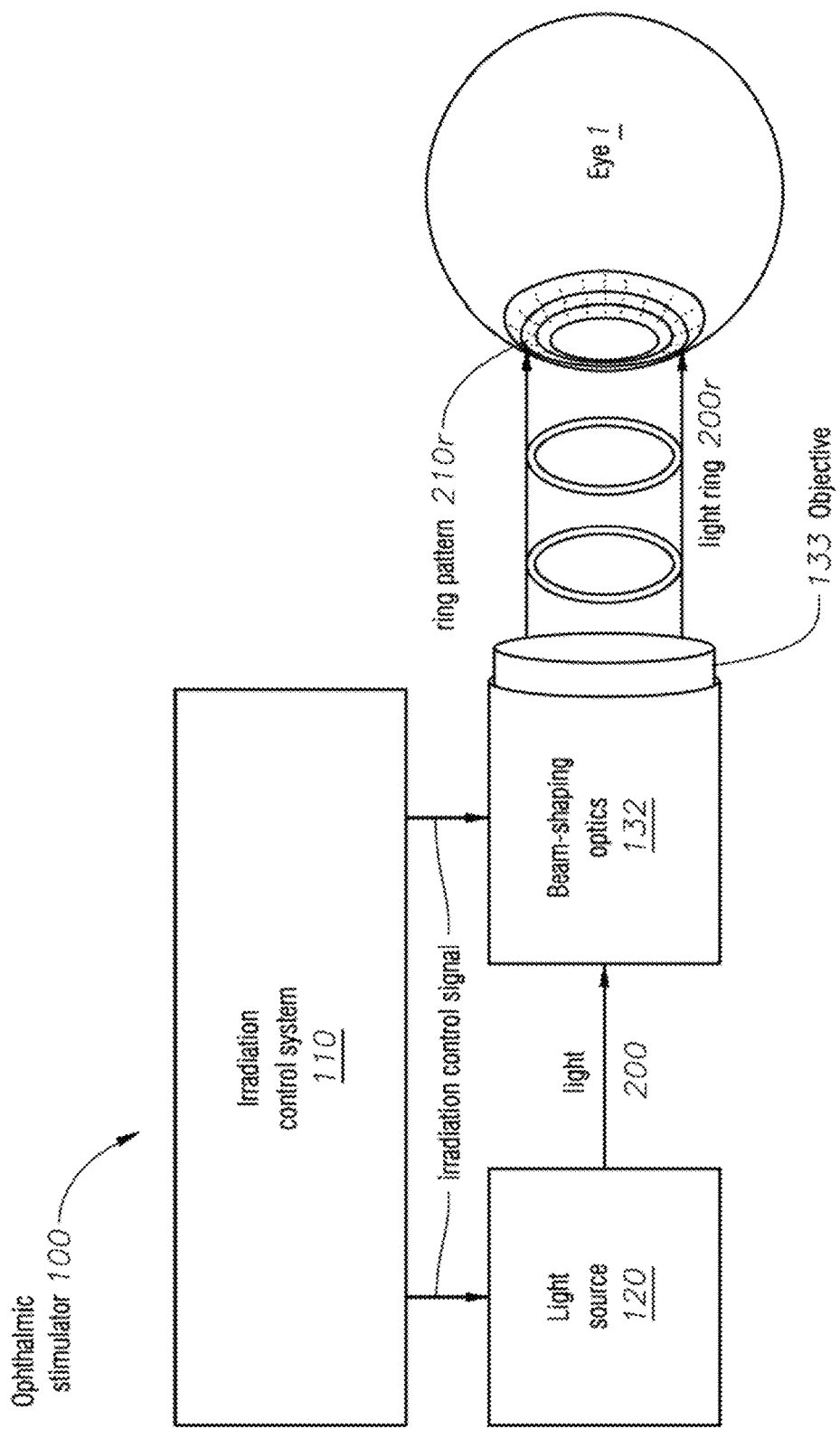

FIG. 7A illustrates that some embodiments of the ophthalmic stimulator 100 may include an irradiation control system 110, to generate an irradiation control signal; a light source 120, coupled to the irradiation control system 110, to generate a light beam 200; and a beam-shaping optics 132, coupled to the irradiation control system 110, to receive the light beam 200 from the light source 120, and to deliver a light ring 200r to an iris 11 of the eye in a ring pattern 210r. In embodiments, the irradiation control system 110 can control the light source 120, or the beam-shaping optics 132, or both, with the irradiation control signal so that the light ring 200r causes a temporary constriction of the pupil of the eye, without causing a permanent constriction of the pupil. The beam-shaping optics can also include an objective 133, to direct the light ring 200p towards the iris of the eye, to provide additional control.

Embodiments of the here-described ophthalmic stimulator 100 can be analogous, or equivalent to the embodiments described in relation to the stimulator 100 in relation to FIGS. 5A-B and 6A-D. In particular, the embodiments of the irradiation source 120 can also serve as the light source 120 here. For example, the light source can be an infrared light source. Also, the beam-shaping optics 132 can be an embodiment of the irradiation delivery system 130.

Figure 7B:
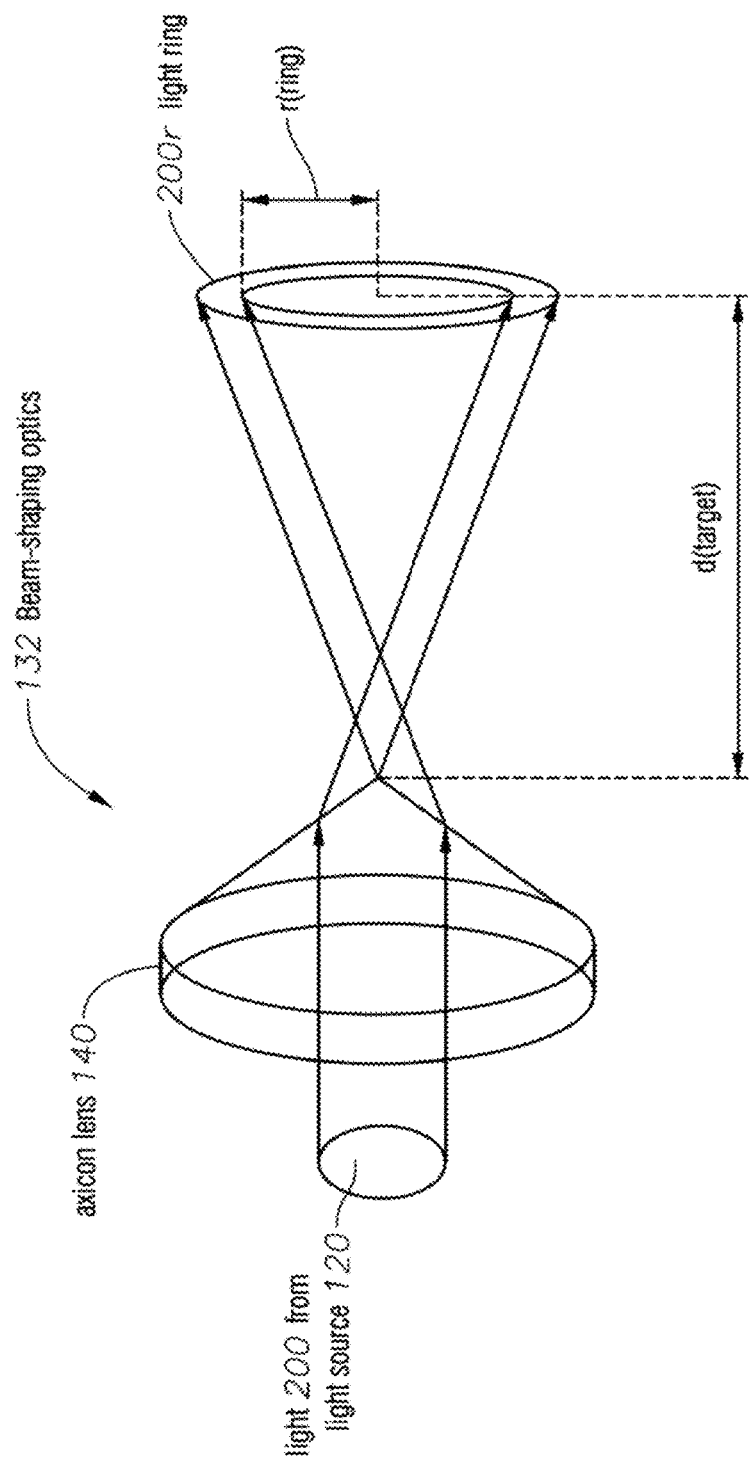

FIG. 7B illustrates that the beam-shaping optics 132 can include a proximal axicon lens 140, positioned with its base-plane oriented toward the light source 120, to transform the received light beam 200 into the light ring 200r.

Here it is recalled that an axicon lens is a glass cone with a circle as its base. An axicon lens can be also visualized as an isosceles triangle, rotated around its axis of symmetry. Direct ray tracing establishes that axicon lenses transform a regular, full light beam into a light ring 200r. Generating the light ring 200r "passively", without any scanners, or other digitally controlled active optics with moving parts, makes an axicon lens a very useful, simple, and reliable implementation of the beam-shaping optics 132 for the purposes of the stimulator 100.

However, it is also noted that the radius r(ring) of the light ring 200r increases with the distance d(target) from the axicon lens 140. Therefore, if the patient moves her/his head along the optical axis, doing so changes the radius r(ring) of the light ring 200r and can have undesirable medical effect.

Figure 7C:
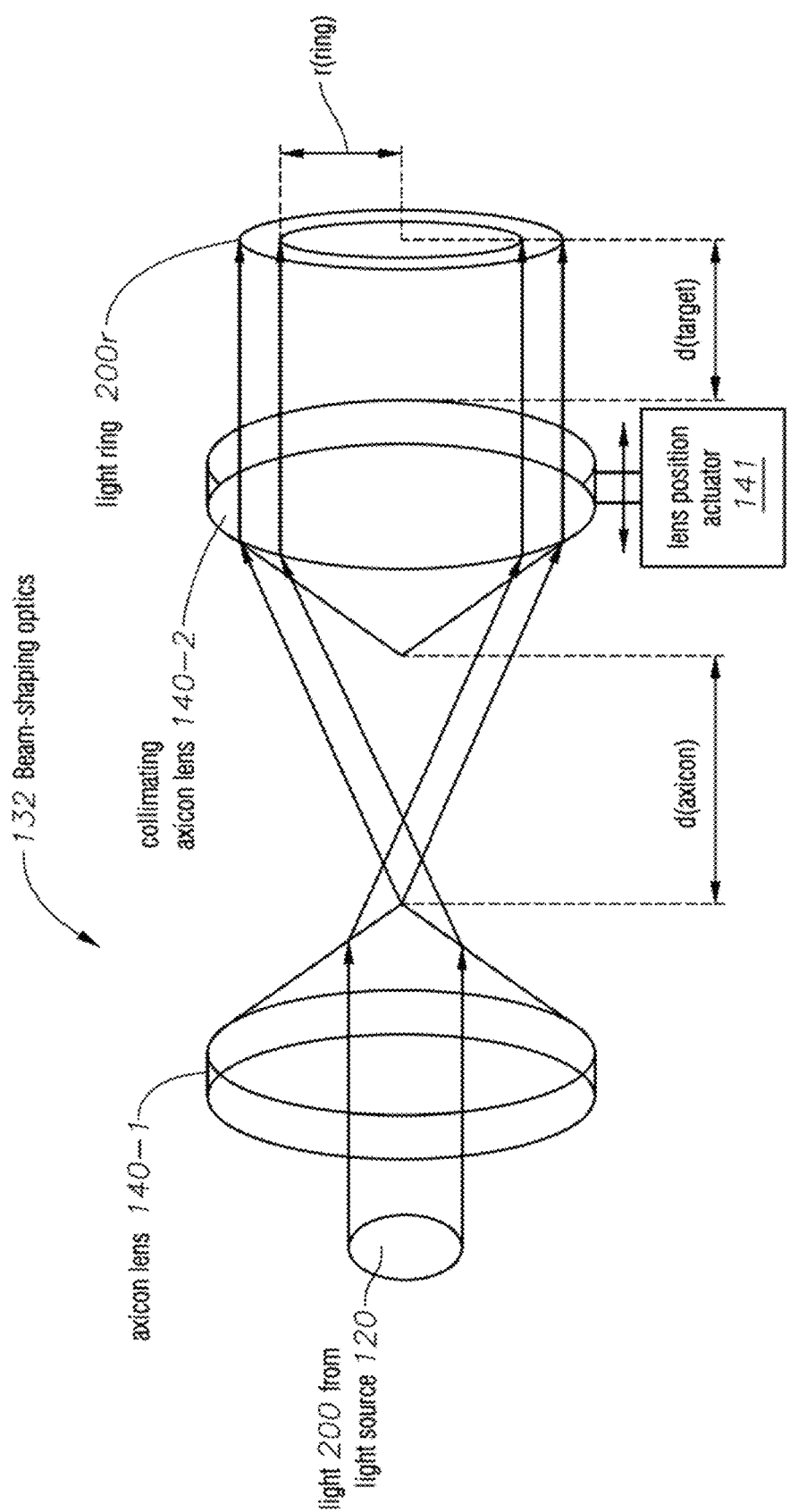

FIG. 7C illustrates an embodiment of the beam-shaping optics 132 that resolves this problem. This embodiment includes the proximal axicon lens 140-1, with its base-plane oriented towards the light source 120. It further includes a second, distal, "complementary" collimating axicon lens 140-2, that is co-axial with the proximal axicon lens 140-1, positioned with its cone-tip oriented toward a cone-tip of the proximal axiom lens 140-1, to collimate the light ring with the increasing radius into a light ring with a constant radius, independent of the distance d(target).

Embodiments with such a complementary axicon lens pair 140-1 and 140-2 can further include a lens position actuator 141, to adjust an axicon distance d(axicon) between the proximal axicon lens 140-1 and the distal axicon lens 140-2. Changing the axiom distance d(axicon) can be used to adjust the radius r(ring) of the light ring 210 as part of the setting of the overall ring pattern 210 by the ophthalmic surgeon in FIGS. 12D-E.

Additional optical solutions may be needed to tune Rp(inner) independently from Rp(outer), to tune the radius of the ring independently from its width. Examples of such solutions include (a) a beam blocker to block out part of the light ring; (b) a deformable axicon lens 140, capable of changing the angle of the cone of the axicon lens; and (c) a deformable mirror, in some cases a deformable conical mirror.

An important aspect of ophthalmic irradiation systems is to ensure that the patient's eye is aligned with the optical axis of the irradiation system. Previously, various alignment systems 135 have been already described. A particularly useful element of such alignment systems 135 can be a fixation light 202, as mentioned. The surgeon may instruct the patient to stare, or fixate, on a centrally positioned fixation light. Such fixation lights 202 can be provided by a small bright LED, positioned centrally, projected into, or superimposed into the optical pathway.

Figure 7D:
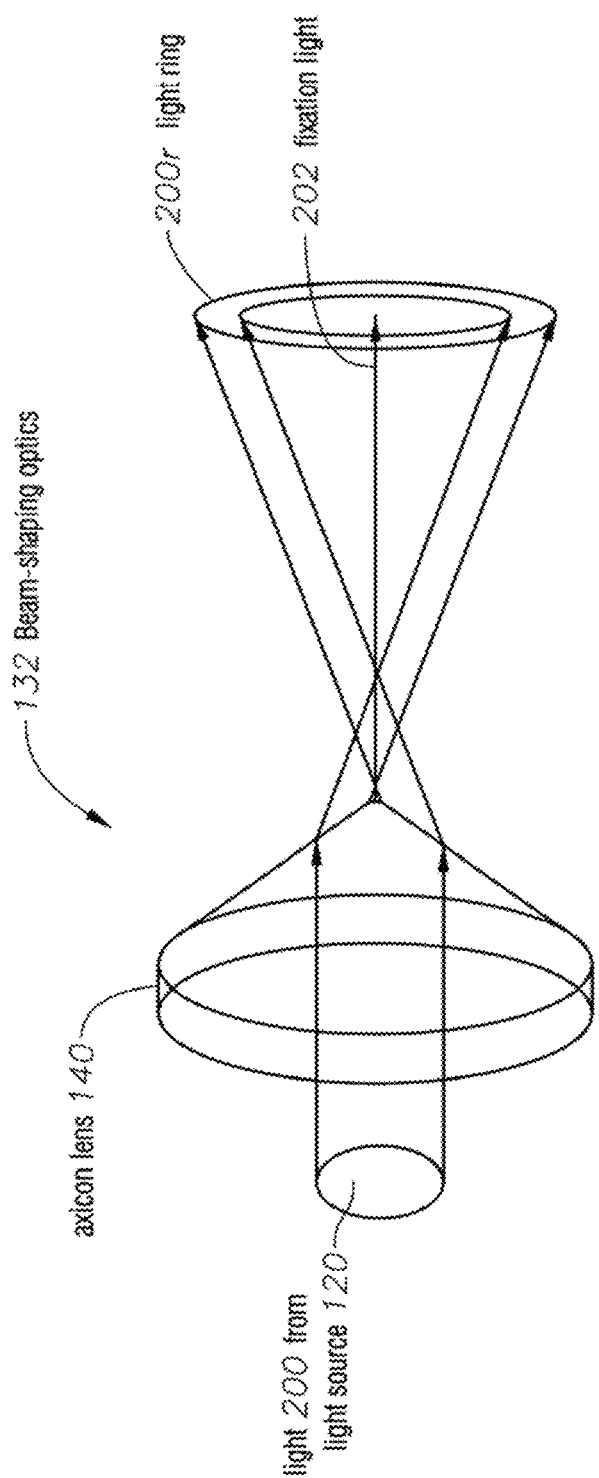

FIG. 7D shows that the beam-shaping optics 132 that uses an axicon lens 140 offers a particularly simple implementation of the fixation light 202. In some embodiments, the tip of the cone of the axicon lens 140 may be flattened. Such flattened tip axicon lenses 140 do not redirect or refract the small central portion of the incoming light 200, so that they propagate centrally and thus can act as the fixation light 202. Such embodiments are attractive because the fixation light 202 is naturally centered with the beam-shaping optics 132, without the need to introduce any additional structures to hold the fixation light in place that can at the same time block part of the light 200, and without the need of centering the fixation light 202 by a finely adjustable system.

In the case when the treatment light 200 is an infrared light, the flattened tip can be covered by a luminescent material, a phosphor, an upconverting material, a higher harmonic generating material, a multi-photon induced fluorescence material, or any optical material or structure that converts the infrared light 200 into a visible light, needed as a fixation light 202.

FIG. 7E illustrates an embodiment of the beam-shaping optics 132. The incoming light 200 can be guided through a pair of beam-expanding lenses: a diverging, lens 142, followed by a collimating lens 143. This 142-143 lens combination can expand the radius of the incoming beam 200 to the Rp(outer) outer radius, set or desired by the ophthalmic surgeon. The beam radius can be adjusted by adjusting the distance of the diverging lens 142 from the collimating lens 143 by an actuator. Next, the expanded beam can be directed at an adjustable beam stop 144 that can block out a central portion of the expanded beam so that the transmitted beam has an inner radius equaling Rp(inner) as set by the surgeon. The radius of the adjustable beam stop 144 can be adjusted by a number of known mechanical designs. Further, since the stopped beam carries an energy with it that can undesirably heat the beam-shaping optics 132, a heat sink 145 can be employed, configured to absorb, or guide away the energy of the stopped beam. Many heat sinks are known, such as metallic ribs, and air-cooled systems. It is also possible to reflect the stopped beam out of the beam-shaping optics 132 and absorb it or release it peripherally. These solutions reduce the need for heat management greatly.

FIG. 7F illustrates another embodiment of the beam-shaping optic 132. This embodiment 132 can be configured to generate a light beam directly with a ring shape, without the need of an optics that would transform the generated light. In a typical embodiment, the light source 200 can include a ring of LEDs 146-1, 146-2, . . . 146-N, collectively referenced as 146-i, to generate light beamlets; and a ring-shaped diffuser 147, to transform the light beamlets into a light beam with a well-distributed intensity profile to form the light ring 200r. In some embodiments, there can be more than one ring of LEDs 146-i. Activating a different number of LED rings can be one way to adjust the radius of the light ring 200r. (Throughout this document, elements "x-1, x-2, . . . , x-N" will be sometimes collectively referenced as "x-i", for brevity.)

Finally, the embodiments of FIGS. 7B-F can be combined. One such combination was already mentioned. The embodiment based on the axicon-lens 140, or 140-1/140-2, may need additional optical elements to adjust the inner and outer radii Rp(inner) and Rp(outer) independently. In some cases, the beam stop 144 can be used to adjust the inner radius Rp(inner) of the light ring 200r that was generated by the axicon lens 140.

Figure 11C:
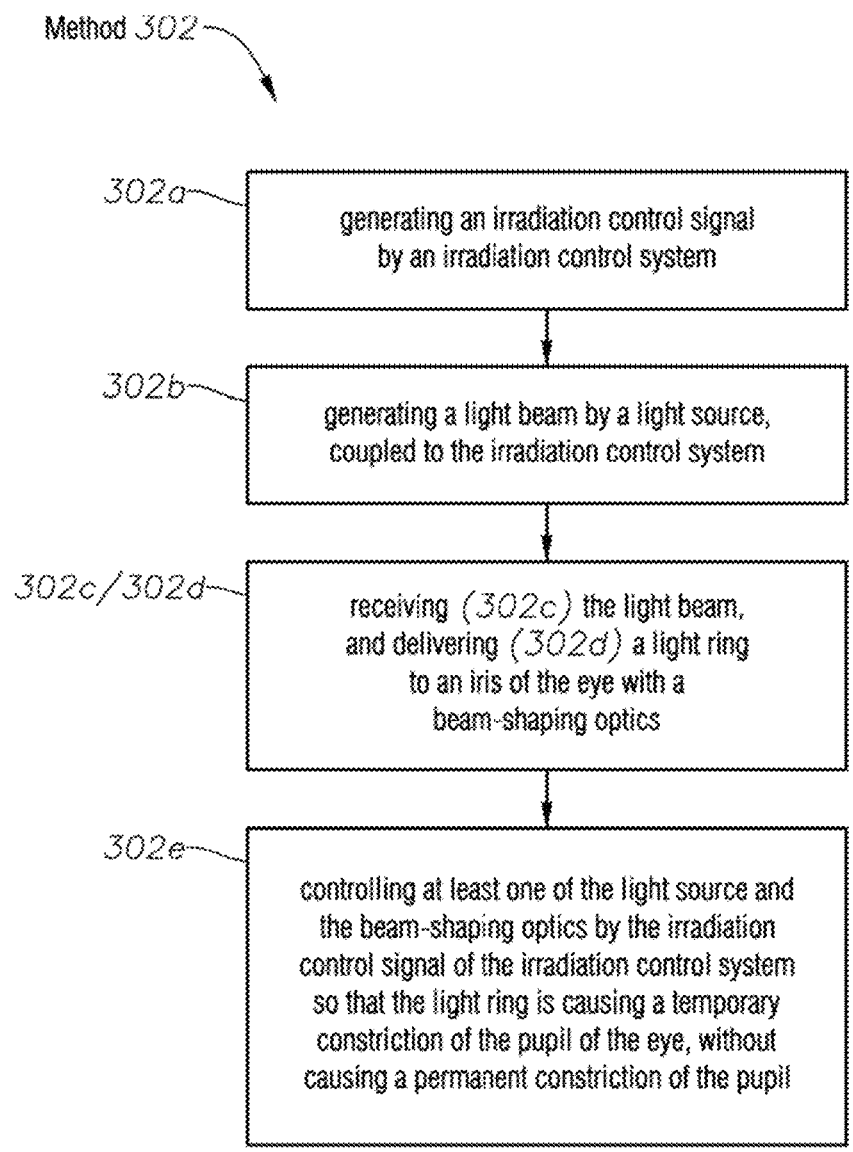

FIG. 11C illustrates a method 302 for temporarily constricting a pupil of an eye by an ophthalmic stimulator 100. The method 302 can include the following steps:

generating 302a an irradiation control signal by an irradiation control system 110;
generating 302b a light beam 200 by a light source 120, coupled to the irradiation control system 110;
receiving 302c the light beam 200, and delivering 302d a light ring 200r to an iris of the eye with a beam-Shaping optics 132; and
controlling 302e at least one of the light source 120 and the beam-shaping optics 132 by the irradiation control signal of the irradiation control system 110 so that the light ring 200r is causing a temporary constriction of the pupil of the eye, without causing a permanent constriction of the pupil.

In some embodiments of the method 302, the delivering 302d the light ring 200r can include transforming the received light beam 200 into the light ring 200r by a proximal axicon lens 140, positioned with its base-plane oriented toward the light source 120, wherein the light ring 200r has an increasing radius r(ring) with increasing distance d(target) from the axicon lens 140.

In some cases, the delivering 302d the light ring 200r can include collimating the light ring with the increasing radius into a light ring 200r with a constant radius by a distal collimating axicon lens 140-2, co-axial with the proximal axicon lens 140-1, positioned with its cone-tip oriented toward a cone-tip of the proximal axicon lens 140-1. In these embodiments, the delivering the light ring can include adjusting an axicon distance d(axicon) between the proximal axicon lens 140-1 and the distal axicon lens 140-2 by a lens position actuator 141, thereby adjusting the radius of the light ring, r(ring).

The method 302 can also include generating a fixation light 202 by selectively transmitting a small fraction of the received light beam 200 by a flattened cone-tip of the proximal axicon lens 140-1. In embodiments where the light is an infrared light, the small, flattened tip of the axicon lens 140-1 can be covered by an optical material that can transform the infrared light into a visible light.

In some embodiments of the method 302, the delivering 302d the light ring can include utilizing a beam stop 144 to generate the light ring 200r by blocking a central portion of the received light beam 200.

Finally, in some embodiments of the method 302, the generating 302b a light beam can include generating the light beam with a ring shape by the light source including a ring of LEDs 146-i.

Figure 8A:
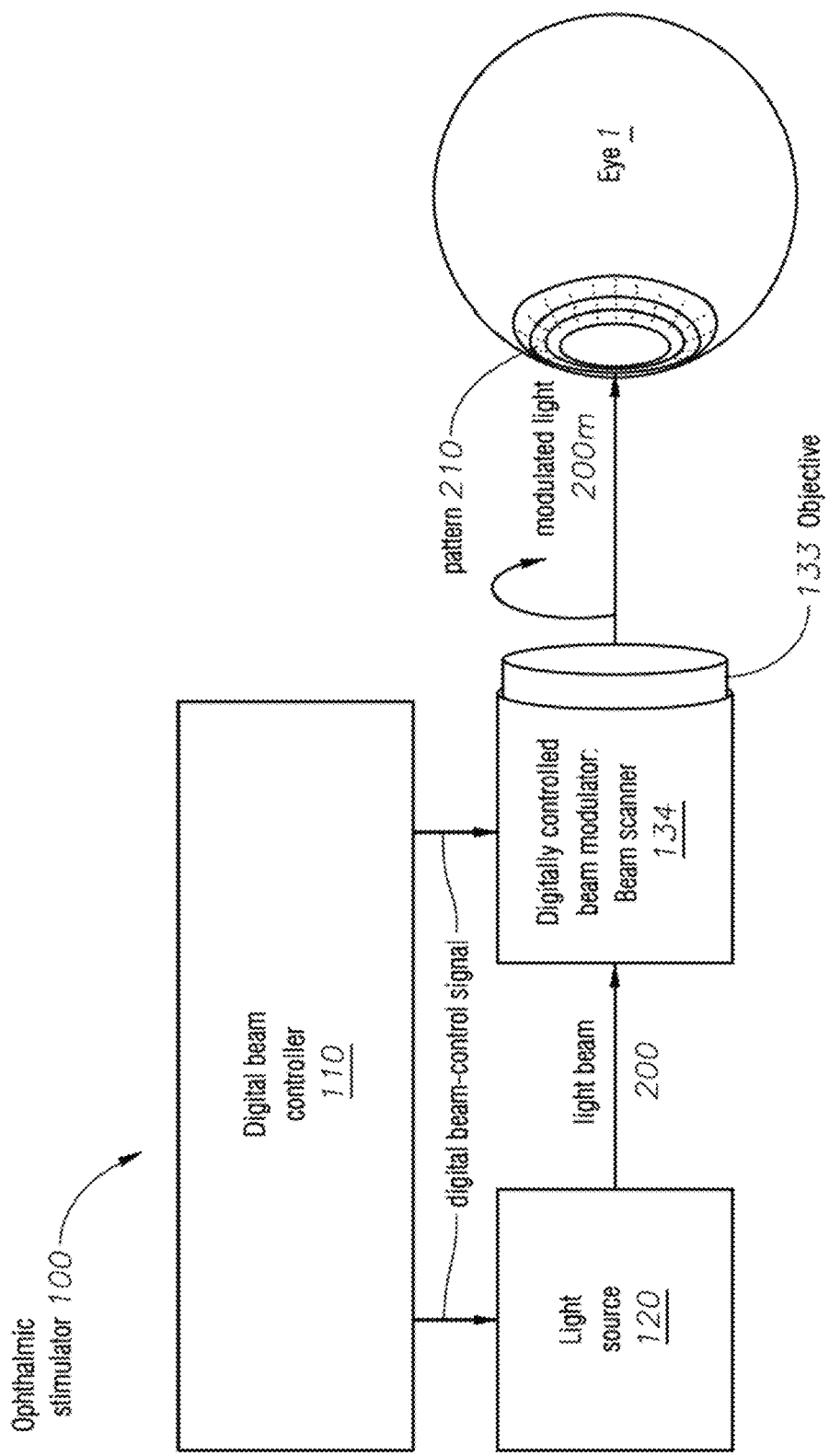
FIGS. 8A-B illustrate embodiments of the ophthalmic stimulator 100 with a digital beam controller 110.

FIG. 8A illustrates that embodiments of the ophthalmic stimulator 100 for temporarily constricting a pupil of an eye can include a digital beam controller 110, to generate a digital beam-control signal; a light source 120, coupled to the digital beam controller 110, to generate a light beam 200; and a digitally controlled beam modulator 134, for example a beam scanner 134, to receive the digital beam-control signal from the digital beam controller 110, to receive the light beam from the light source 120, and to modulate the received light beam into a modulated light, or modulated light 200m, delivered to an iris of the eye. In embodiments, the digital beam controller 110 can control the light source 120, the digitally controlled beam modulator 134, or both, with the digital beam-control signal so that the modulated light 200m causes a temporary constriction of the pupil of the eye, without causing a permanent constriction of the pupil.

As before, embodiments of the here-described ophthalmic stimulator 100 can be analogous, or equivalent to the embodiments described in relation to the ophthalmic stimulator 100 in relation to FIGS. 5A-B, 6A-D, and 7A-F. In particular, the embodiments of the irradiation control system 110 can be analogous, or equivalent, to the embodiments of the digital beam controller 110, the irradiation source 120 can also serve as the light source 120 here, and the digitally controlled beam controller 134 can be an embodiment of the irradiation delivery system 130.

In what follows, numerous examples of the digitally controlled beam modulator 134 will be described. To emphasize that all these are embodiments of the same block, they are all labeled with 134 or as a variant of label 134.

For example, FIG. 8A illustrates a beam scanner 134 as an embodiment of the digitally controlled beam modulator 134, to scan the received light beam 200 according to a pattern 210 on the iris. Embodiments described in relation to FIGS. 8A-B, and FIGS. 9A-E can be different from the embodiments described in relation to FIGS. 7A-F in that the latter embodiments utilize dominantly "passive" optical elements, such as lenses and mirrors, and do not need elaborate digital control signals and moving parts, with the possible exception of the lens position actuator 141. Also, the systems of FIGS. 7A-F typically irradiate the pattern 210 simultaneously.

In contrast, the digitally controlled embodiments of FIGS. 8A-B, and FIGS. 9A-E can involve active elements, where extensive digital control signals move or adjust a number of active optical elements. These embodiments typically irradiate the iris on a point-by-point basis, with the help of various types of scanners and optical arrays. As such, these digitally controlled embodiments can offer higher precision and control, at the same time, they can be more complex, raising issues of reliability, maintenance and costs, and the irradiation treatment can take longer. Also, the points of the pattern 210 are often irradiated sequentially, instead of simultaneously.

Figure 8B:
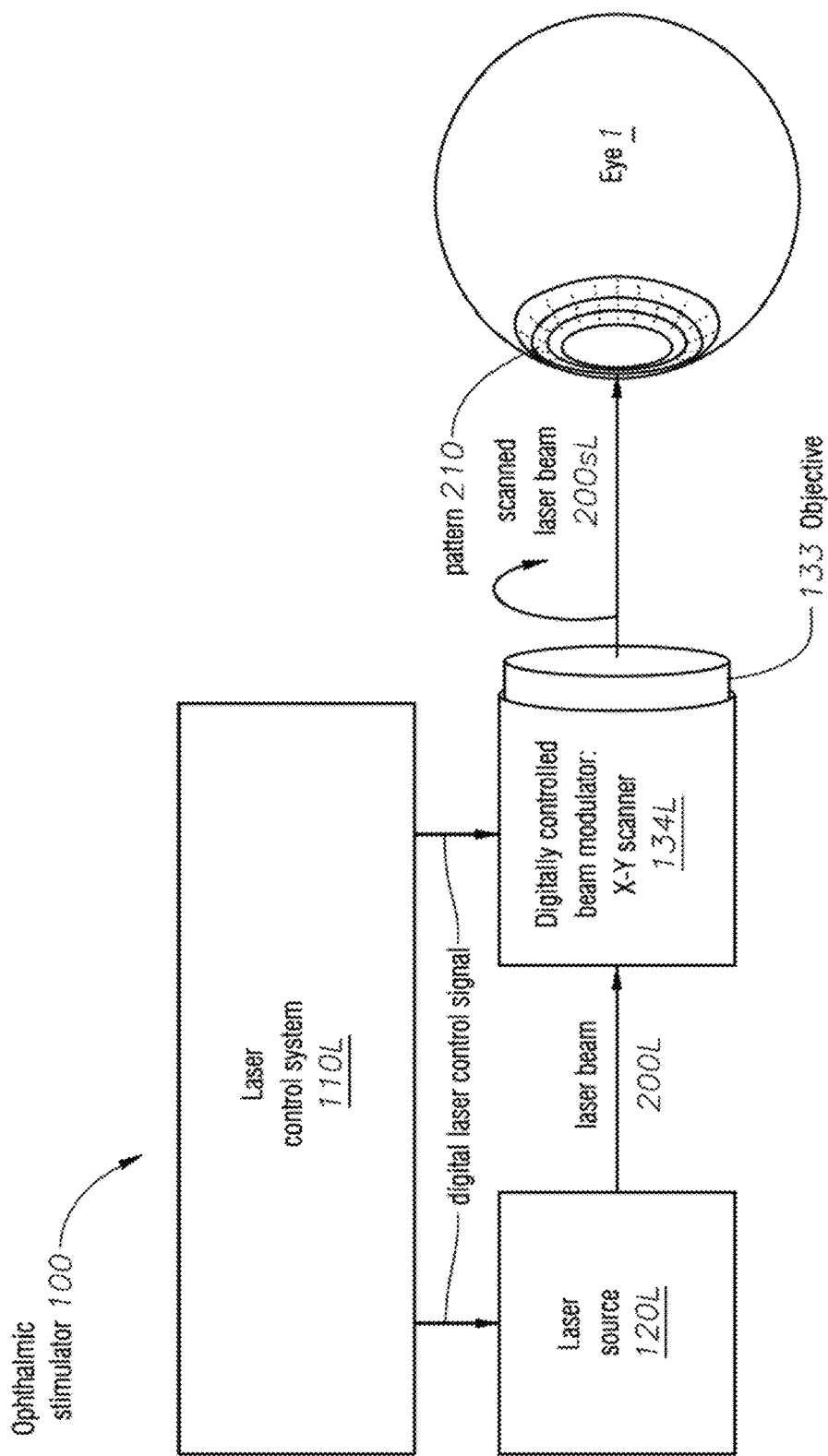

FIG. 8B illustrates one embodiment of the digitally controlled beam modulator 134 in a laser-based ophthalmic stimulator 100. The light source 120 can be a laser source 120L, emitting a laser beam 200L. The digitally controlled beam modulator 134 can be an X-Y scanner 134L, to scan the received laser beam 200L as a scanned laser beam 200sL according to a pattern on the iris. A large number of laser scanners are known that can scan the scanned laser beam 200sL with a wide variety of complex patterns 210.

Figure 9A:
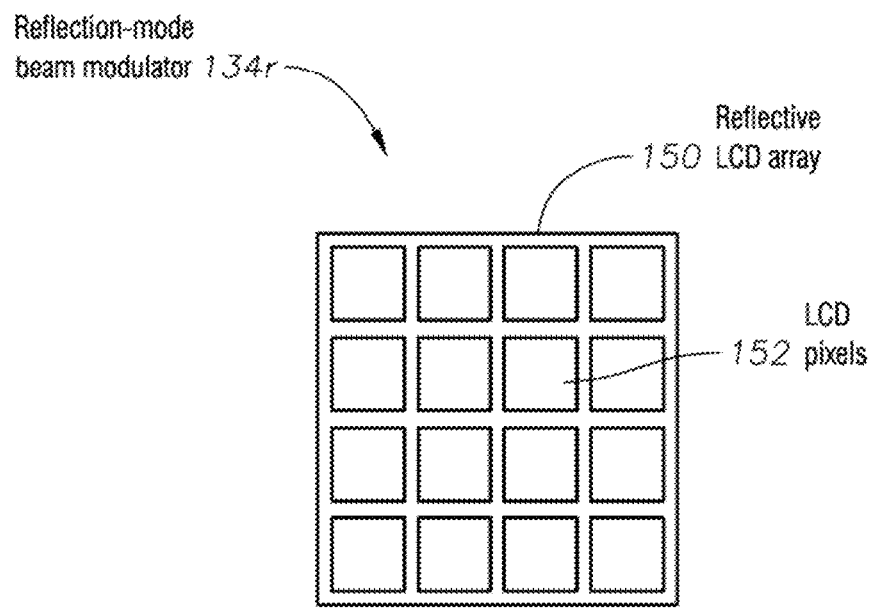
FIGS. 9A-E illustrate embodiments of the beam modulator 134.

FIG. 9A illustrates the first of a set of reflection mode beam modulators 134r. While the scanner embodiments in FIGS. 8A-B irradiate the iris in a pattern 210 sequentially, the embodiments of FIGS. 9A-E can irradiate the pattern 210 either sequentially, or simultaneously. The embodiment of FIG. 9A includes a reflective LCD array 150 with an addressable array of LCD pixels 152. Switching the LCD pixels 152 on-off can control how much of an incoming light the LCD array reflects from through the LCD pixels.

Figure 9B:
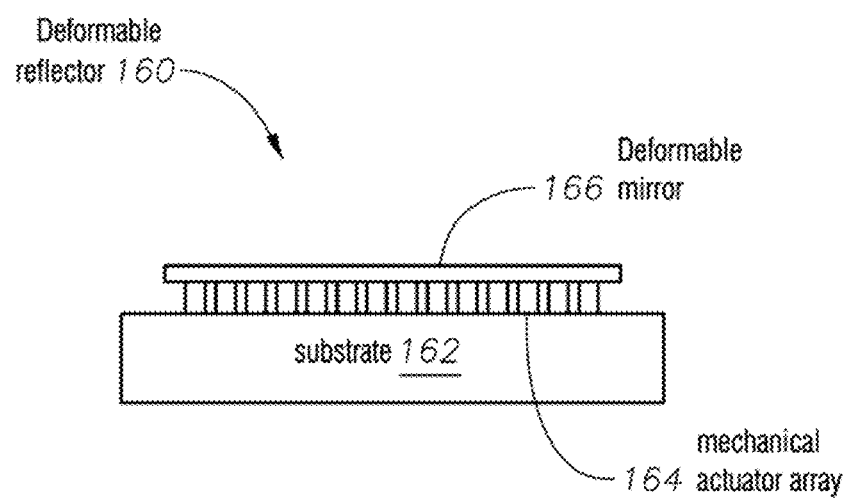

FIG. 9B illustrates another embodiment of the reflection-mode beam modulator 134r that includes a deformable reflector 160, with a substrate 162; a mechanical actuator array 164, positioned on the substrate 162; and a deformable mirror 166, positioned to be deformable by the mechanical actuator array 164 according to the digital beam-control signal.

Figure 9C:
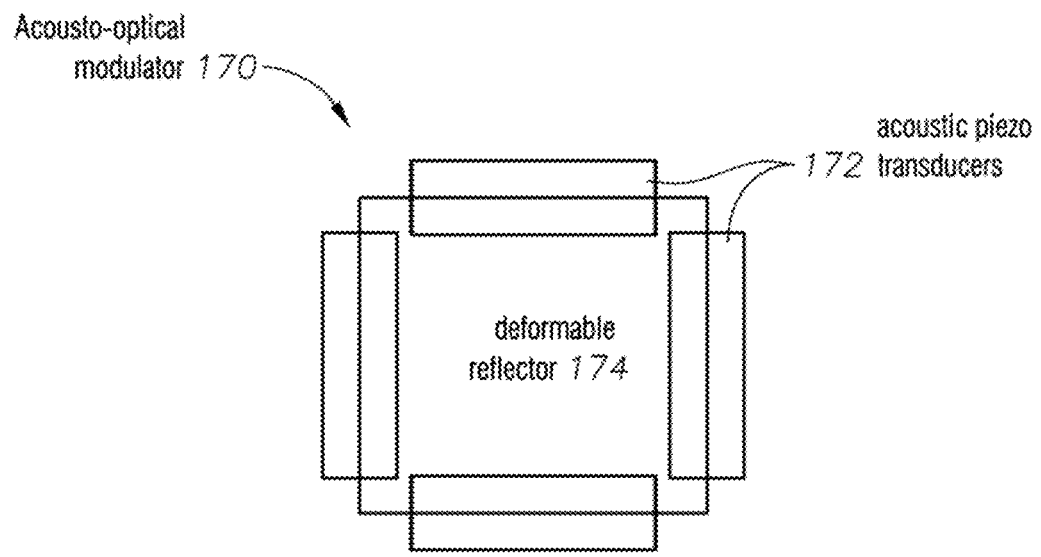

FIG. 9C illustrates yet another embodiment of a reflection-mode beam modulator 134r. This is an acousto-optical modulator 170 that includes a set of acoustic piezo transducers 172, to deform a deformable reflector 174, according to the beam-control signal. This embodiment has similarities to the previous one in FIG. 9B. One of the differences is that the deformation is performed not by an array that can be controlled point-by-point, but in a global manner, where the transducers are operated to form patterns across the entire deformable reflector 174 simultaneously.

Figure 9D:
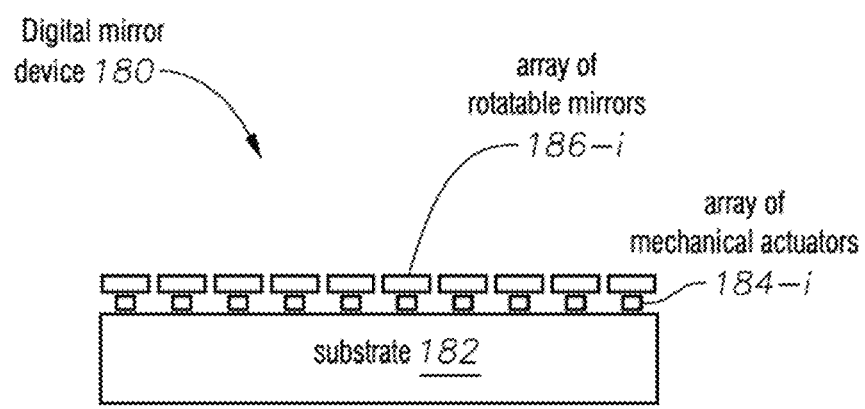

FIG. 9D illustrates yet another embodiment of a reflection-mode beam modulator 134r. This is a digital mirror device 180 that includes a substrate 182; an array of mechanical actuators 184-i, positioned on the substrate 182; and an array of rotatable mirrors 186-i, where the rotatable mirrors 186-i are rotatable individually by the actuators 184-i according to the beam-control signal. Such digital mirror arrays are well known in digital projectors, for example.

Figure 9E:
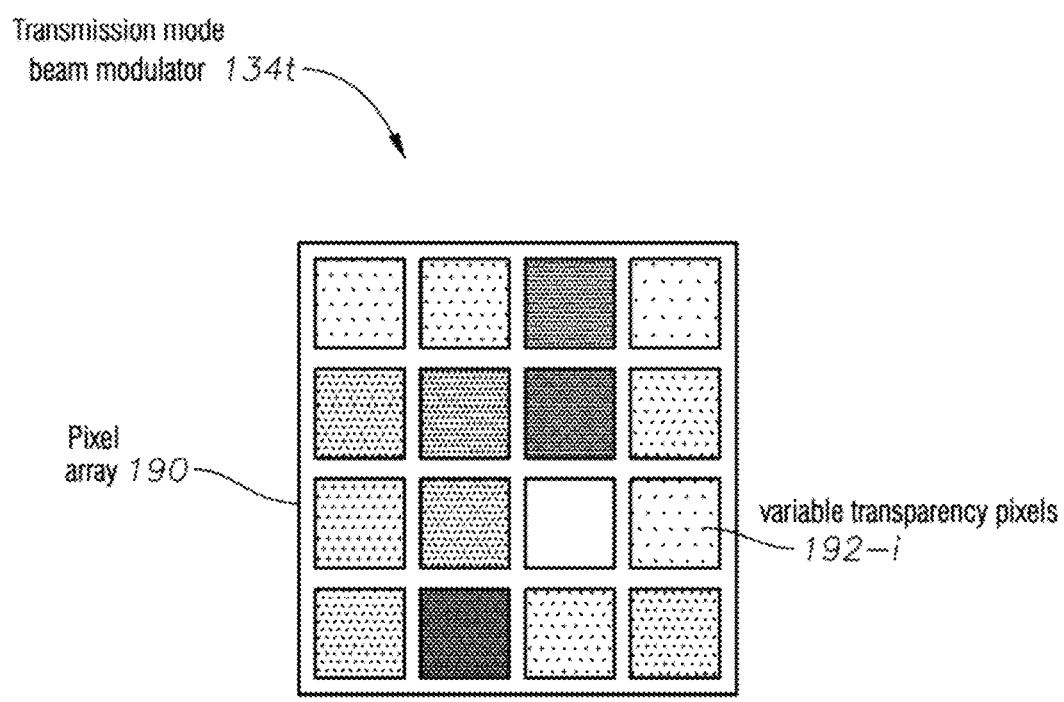

FIG. 9E illustrates a different, transmission-mode beam modulator 134t. This embodiment can include an addressable pixel array 190 of variable transparency pixels 192-i. This embodiment 190 has design aspects analogous to the embodiment 150 in FIG. 9A, as it also builds on the principle of individual pixels changing their optical (reflective or transmissive) properties under electric, control, thereby modulating the beam on a pixel-by-pixel basis. As indicated earlier, the irradiation can be either sequential or in parallel, the latter type embodiments requiring much less moving parts and allowing shorter irradiation times.

Figure 17B:
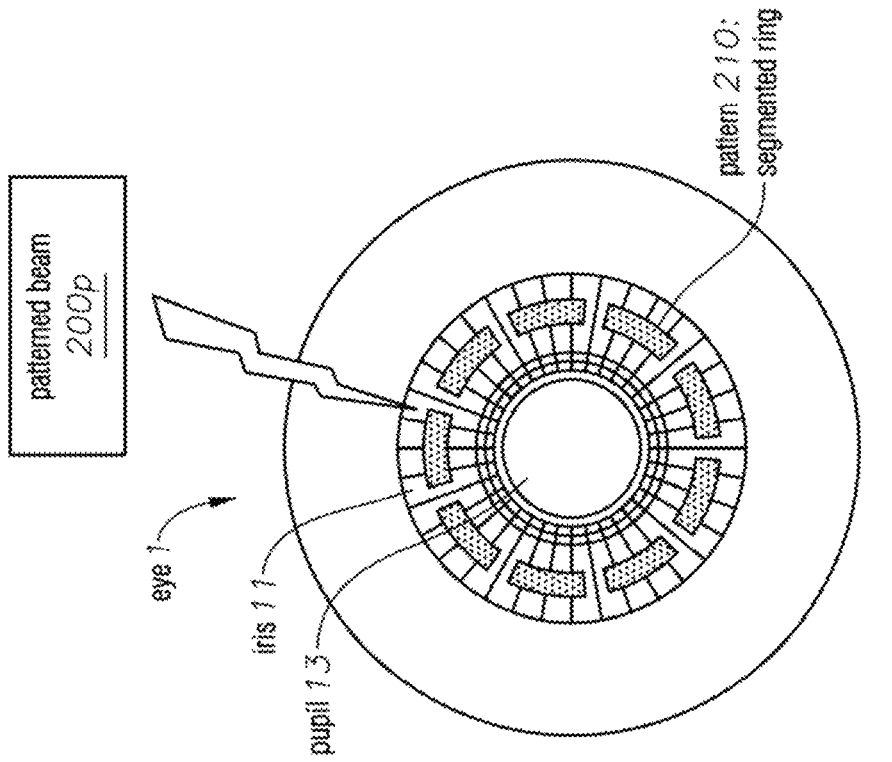
FIGS. 17A-D illustrate various irradiation patterns 210.
Figure 17A:
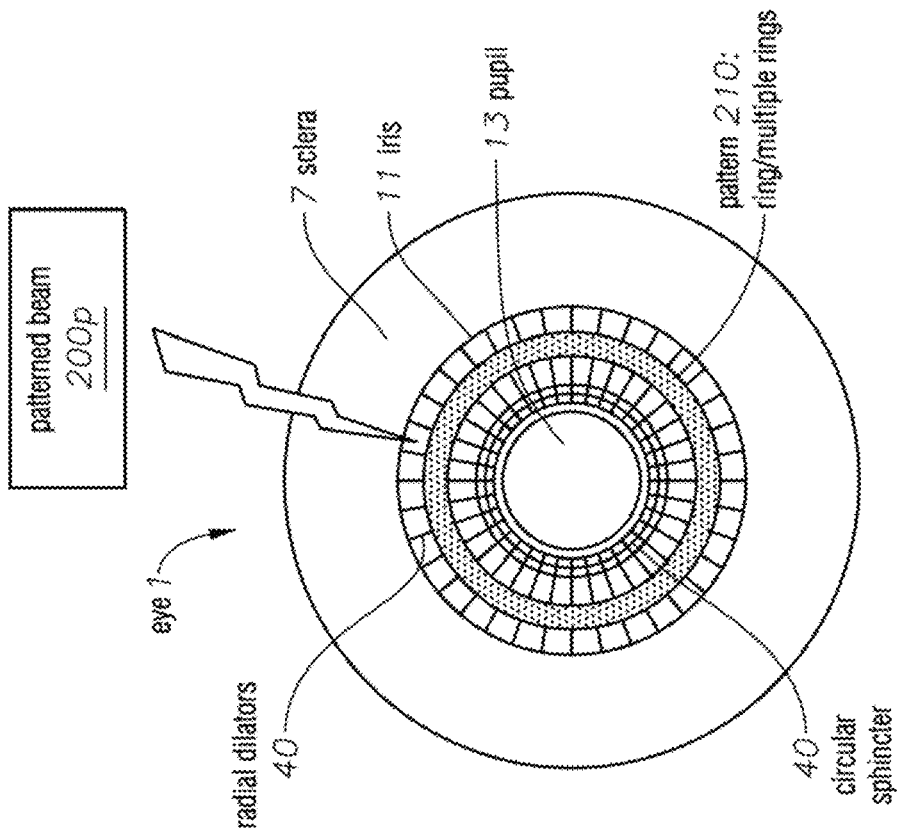
Figure 17D:
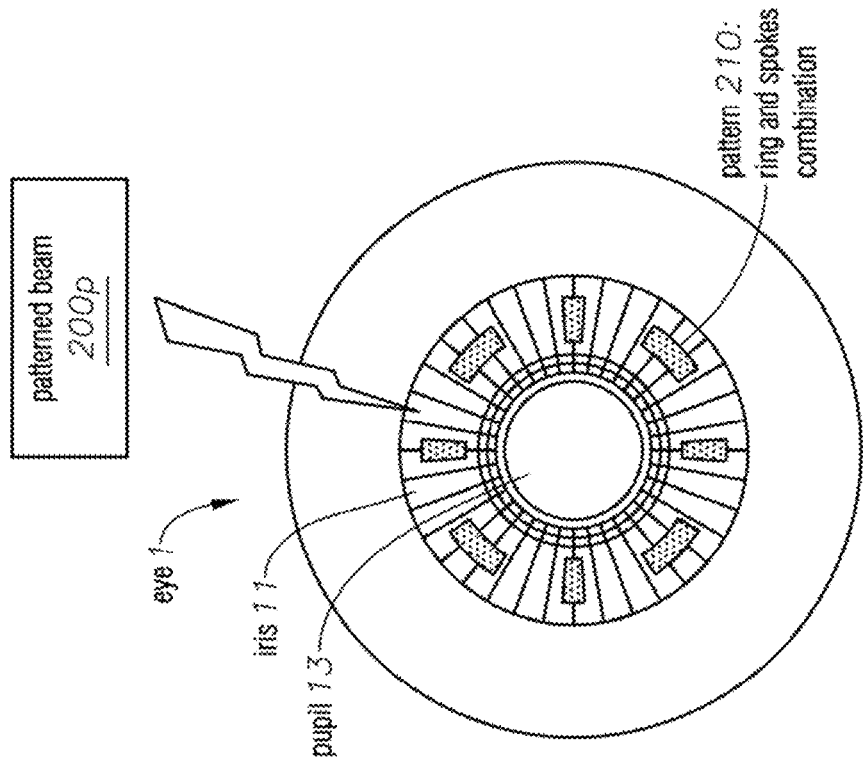
Figure 17C:
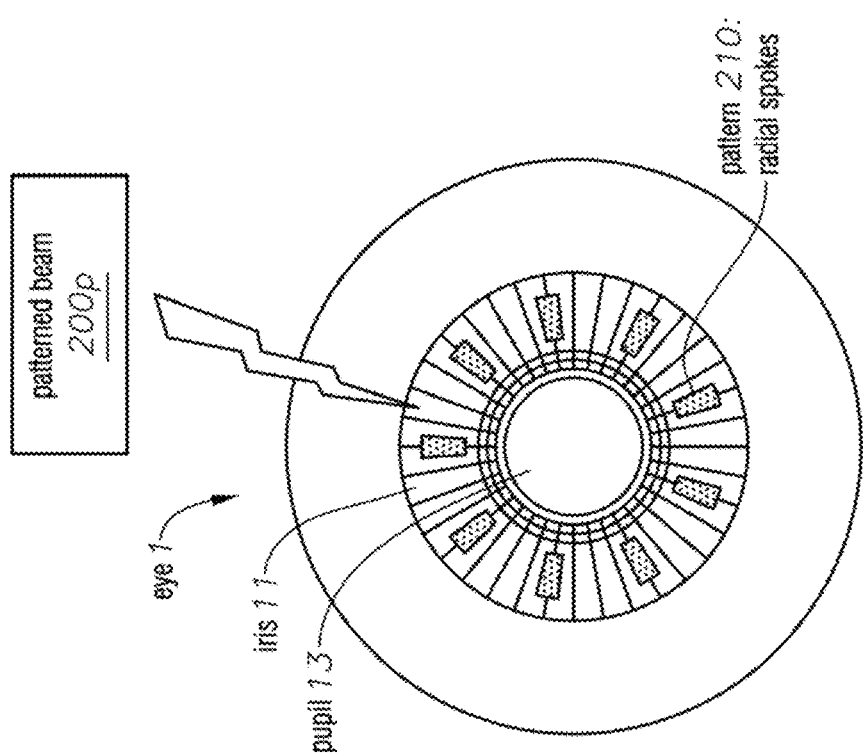

FIGS. 17A-D illustrate various patterns 210 the digitally controlled ophthalmic stimulators 100 can irradiate on the iris with the modulated beam 200m. In embodiments, illustrated in FIG. 17A, the digitally controlled beam modulator 134 can be controlled by the beam controller 110 to modulate the received light beam 200 into a modulated light 200m, so that it irradiates a pattern 210 that is a ring, or multiple rings. FIG. 17B illustrates a pattern 210 that is a segmented ring. FIG. 17C illustrates a pattern 210 that includes radial spokes. Finally, FIG. 17D illustrates a pattern that is a combination of ring segments and spokes.

Figure 11D:
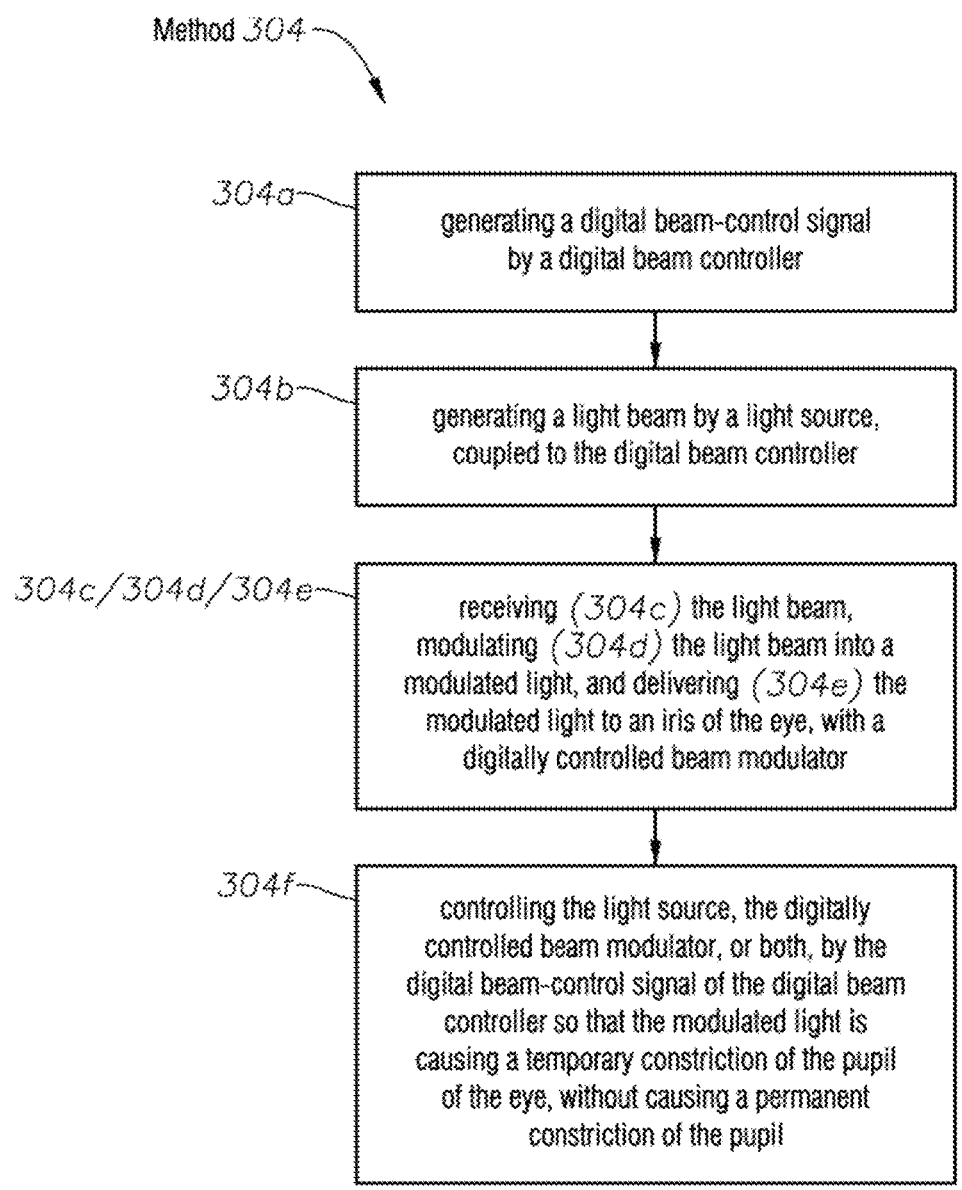

FIG. 11D illustrates a method 304 that is related to operating the digitally controlled ophthalmic stimulators 100. The method 304 can include the following steps:

generating 304a a digital beam-control signal by a digital beam controller 110;

generating 304b a light beam 200 by a light source 120, coupled to the digital beam controller 110;

receiving 304c the light beam 200, modulating 304d the light beam 200 into a modulated light 200m, and delivering 304e the modulated light 200m to an iris of the eye, with a digitally controlled beam modulator 134; and controlling 304f the light source 110, the digitally controlled beam modulator 134, or both, by the digital beam-control signal of the digital beam controller 110 so that the modulated light 200m is causing a temporary constriction of the pupil of the eye, without causing a permanent constriction of the pupil.

In embodiments, the modulating 304d can include scanning the received light beam on the iris according to a pattern by a beam scanner 134. In other embodiments, the modulating 304d can include modulating the light by a reflection-mode beam modulator 134r. The reflection-mode beam modulator 134r can be a reflective LCD array 150, with an addressable array of LCD pixels, a deformable reflector 160, an acousto-optical modulator 170, and a digital mirror device 180. In some embodiments of the method, the modulating 304d can include modulating the light by a transmission-mode beam modulator 134t.

Finally, the modulating 304d can include modulating the received light beam into the modulated light 200m with the pattern being one of a ring, multiple rings, a segmented ring, a pattern of radial spokes, and a combination of ring segments and spokes.

Figure 15:
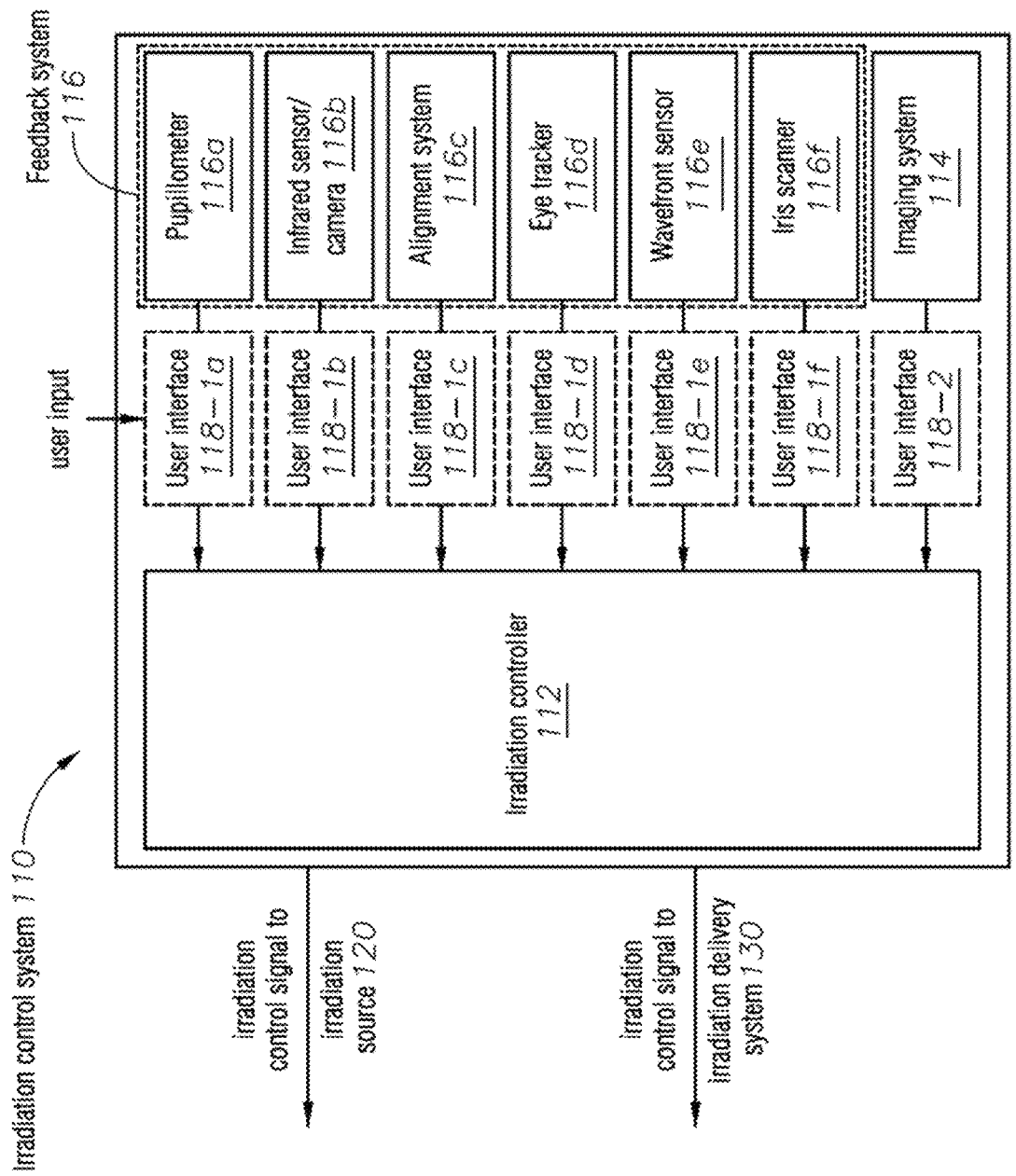
FIG. 15 illustrates an embodiment of the feedback system, 116.

FIG. 15 illustrates other embodiments of an ophthalmic stimulator 100 for temporarily constricting a pupil of an eye that includes an irradiation control system 110, having a feedback system, to generate an irradiation control signal using a feedback of the feedback system; an irradiation source 120, coupled to the irradiation control system 110, to generate an irradiation; and an irradiation delivery system 130, coupled to the irradiation control system 110, to receive the irradiation 200 from the irradiation source 120, and to direct a patterned irradiation 200p in a pattern to a treatment region of an iris of the eye, guided by the feedback-based irradiation control signal; wherein the irradiation control system 110 controls at least one of the irradiation source 120 and the irradiation delivery system 130 with the feedback-based irradiation control signal so that the patterned irradiation 200p causes a temporary constriction of the pupil, without causing a permanent constriction of the pupil. As before, the here-described embodiments can be analogous to the ones described in relation to FIGS. 5A-B, FIGS. 6A-D, FIGS. 7A-F, and FIGS. 8A-B, and analogously labeled elements can serve analogous functions.

In what follows, various embodiments and blocks of the feedback system 116 will be described. These embodiments and blocks typically include a hardware block, such as an imaging system, or a temperature sensor. They are coupled to the irradiation controller 112, which processes their feedback and generates irradiation control signals, to be transmitted to the irradiation source 120 and to the irradiation delivery system 130. As discussed in relation to FIG. 10, the irradiation controller 112 can include corresponding blocks that are dedicated to receive the feedback. For example, the irradiation controller 112 can include the dedicated feedback block 112a to receive the feedback from an embodiment of the feedback system 116. These receiving blocks can be implemented in hardware, such as an application specific integrated circuit ASIC; or they can be implemented in a software form, such as a piece of code or application, implemented in the processor 113 of the irradiation controller 112; or in a shared processor, or input/output controller. In yet other embodiments, the feedback can be coupled straight into the central processor 113, whose code can process the feedback directly. A particularly simple implementation can be a simple "stop" feedback signal, triggered by a security concern, which can be directly executed by the processor by shutting down the irradiation source 120 with a control signal, without the need of any intermediate processing.

In some embodiments, the feedback system 116 can include at least one of a pupillometer 116a and an imaging system 114, to sense a diameter of the pupil, and to generate a feedback according to the sensed pupil diameter. As discussed just now, this feedback can be received and processed either by a dedicated feedback block 112a that is implemented inside the irradiation controller 112, or can be received by the processor 113 of the irradiation controller 112 itself. In some embodiments, the pupillometer 116a can be coupled to the irradiation controller 112 directly, in others, through a user interface 118-1a. Similarly, the imaging system 114 can be coupled to the irradiation controller 112 directly, or through a user interface 118-2.

FIGS. 16A-E illustrate methods, or processes, 510-550 that operate in relation to the embodiments 116a-f of the feedback system 116. In general, the methods, or processes, 510-550 can include the following steps:
generating a feedback-based irradiation control signal by an irradiation control system 110, using a feedback of a feedback system of the irradiation control system;
generating an irradiation 200 by an irradiation source 120, coupled to the irradiation control system;
receiving the irradiation 200 and directing a patterned irradiation 200p to a treatment region of an iris of the eye with an irradiation delivery system 130, guided by the feedback-based irradiation-control signal; and
controlling at least one of the irradiation source 120 and the irradiation delivery system 130 with the feedback-based irradiation control signal of the irradiation control system 110 so that the patterned irradiation 200p causes a temporary constriction of the pupil, without causing a permanent constriction of the pupil.

Figure 16A:
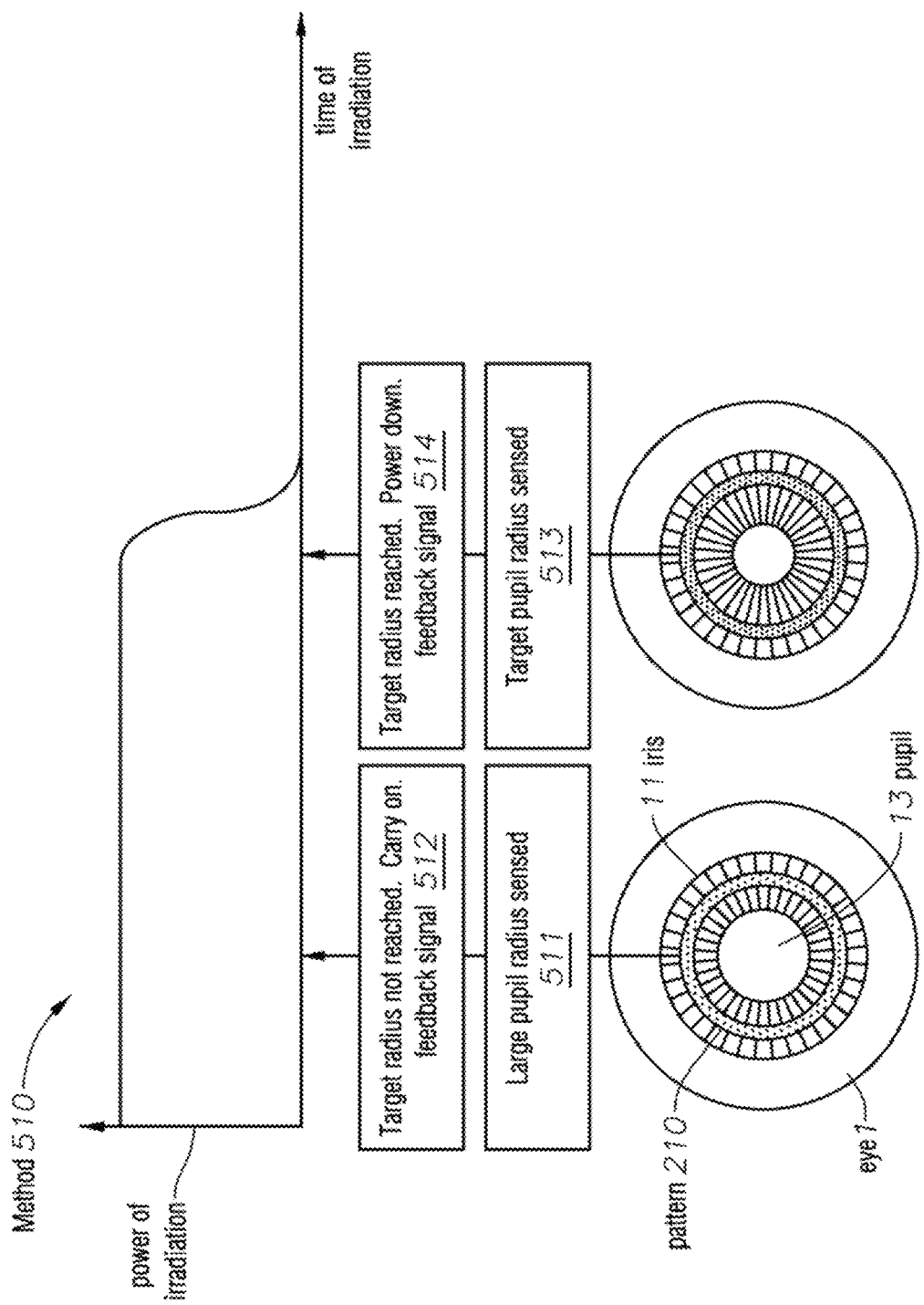
FIGS. 16A-E illustrate methods 510-550.

The description continues with details of the processes, or methods, 510-550. FIG. 16A illustrates that in a representative case, the feedback can be generated through the following sequence, method, or process 510. A short time after starting to apply the patterned irradiation 200p to the iris 11 according to the pattern 210, in step 511, the pupillometer 116a, or the imaging system 114, can sense that "Pupil radius is large relative to a reference or target", or "Target radius not reached". This can be followed by a step 512, generating the feedback, or feedback signal: "Carry on irradiation", as indicated by the eye and steps on the left side of FIG. 16A. Here and in what follows, each "step x of generating feedback signal" may also be referred to with the shorter form of "feedback signal x", for brevity. Also, the feedback signal can include not only the command to continue or to stop the irradiation, but it can also include the sensed information as well. In the present example, the step 512 of generating a feedback signal can include sending the feedback signal "Target radius not reached. Carry on."

With the passing of time, the irradiation increases the temperature of a portion of the iris 11, as indicated by the denser dot-filling of the pattern 210 on the right. The increased temperature induces the constriction of the pupil 13, as indicated by the eye 1 having a smaller pupil 13 on the right of FIG. 16A. In step 513, the pupillometer 116a, or the imaging system 114, can sense that "Pupil radius is sufficiently close to the reference", or "Target pupil radius sensed", This can be followed by the generation of the feedback in step 514: "Power down irradiation", or "Target radius reached. Power down". This feedback, or feedback signal 514 can be transmitted by the feedback system 116 to the irradiation controller 112. In response, the irradiation control system 110 can send a corresponding feedback-based irradiation control signal to the irradiation source 120 to power down. The top graph of FIG. 16A illustrates that the feedback-induced irradiation control signal 514 causes the powering down of the irradiation after the receiving of the feedback signal 514.

It is mentioned here that pupillometers reached a high level of sophistication and can provide a variety of useful, actionable information. For a review of the field, see Olson D, Stutzman S, Saju C, Wilson M, Zhao, W., Aiyagari V. Interrater of Papillary Assessments, Neurocrit Care, Published online: 17 Sep. 2015. These pupillometers can assess pupil size, and shape with very high accuracy and reproducibility. In addition, such devices can measure parameters such as onset and peak constriction, constriction and dilation velocity, and latency using various light stimuli, both before and after treatment to assess effects that may not be apparent simply based on pupil diameter.

FIG. 15 illustrates that in some embodiments, the feedback system 116 can include a pupillometer 116a, and at least one of an infrared sensor or camera 116b to sense a temperature of the treatment region, and to generate a feedback according to the sensed temperature. As before, the infrared camera 116b can be coupled to the irradiation controller 112 directly, or via a user interface 118-1b.

Figure 16B:
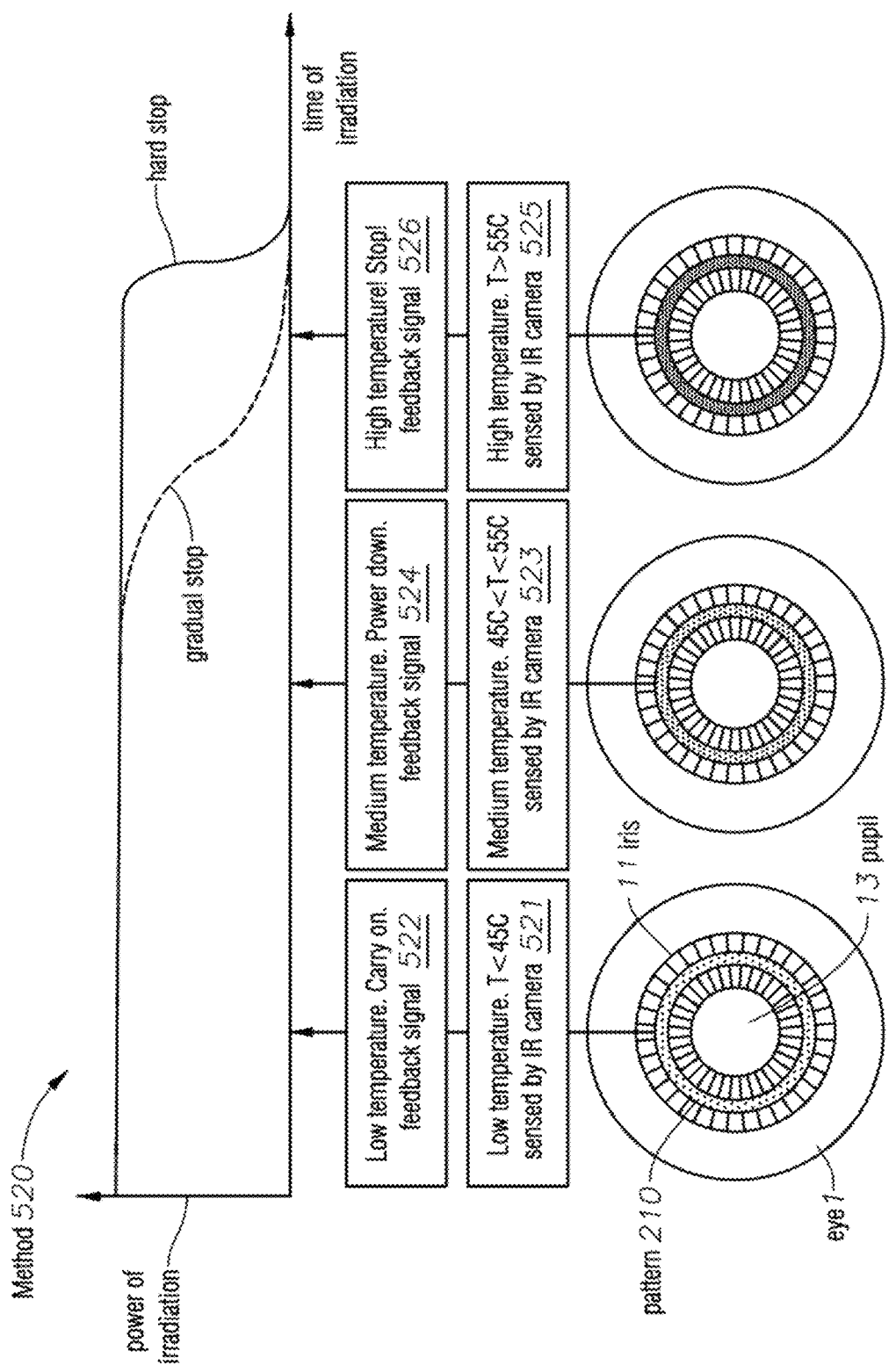

FIG. 16B illustrates the corresponding process 520, or method 520, or sequence of operation of this infrared sensor/camera 116b. At an early time during the irradiation, in a step 521, the infrared sensor/camera 116b can sense "Temperature low relative to a reference", or simply "Low temperature". In a typical case, a temperature T sensed to be less than 45 C can be classified as "low temperature". This can prompt generating the feedback in step 522: "Carry on irradiation". Visibly this feedback leads to the maintaining the power of the irradiation, as indicated by the graph on top of FIG. 16B.

With the progression of the irradiation time, the target region, irradiated according to the pattern 210, starts warming up. This is indicated by the dotting of the pattern 210 getting denser. After some time, in step 523, the infrared (thermal) sensor/camera 116b can sense "a medium temperature relative to the reference", or simply "medium temperature". In a typical example, this can be a temperature in the 45 C-55 C range. In response, a feedback signal can be generated in step 524, sent from the feedback system 116 to the irradiation controller 112: "Start power down the irradiation", or "Medium temperature. Power down". As indicated, the irradiation control system 110 can generate a feedback-based irradiation control signal to the irradiation source 120, which is response can start powering down the power of the irradiation gradually, as indicated by the dashed line in the top graph.

In some embodiments, the settings and thresholds can be chosen differently. In such cases, the IR camera 116b can wait until it senses a "high temperature relative to the reference" in step 525, such as the IR sensor/camera 116b senses the temperature T that exceeds 55 C. Such a sensing by the IR sensor/camera 16b can prompt the generation of the feedback "Stop the irradiation" in step 526, to be sent to the irradiation controller 112. Analogously to earlier steps of the process, the irradiation control system 110 can generate a feedback-based irradiation control signal for the irradiation source 120 to discontinue the irradiation with a hard stop, as indicated by the solid line in the top graph of FIG. 16B.

One such scenario can be associated with an irregular, or unexpected progress of the irradiation, when, for whatever reason, the iris heats faster than expected. This can be a consequence of an unexpected patient response, or an incorrect calibration of the irradiation's treatment parameters. Once the IR camera 116b senses that the temperature rose to a value high relative to a reference, such as to above 55 C, for safety reasons the feedback-based irradiation control signal can bring the irradiation power to zero via a hard stop.

FIG. 15 illustrates that the feedback system 116 can further include at least one of an alignment system 116c, an eye tracker 116d, a wavefront sensor 116e, an iris scanner 116f, and an imaging system 114. The alignment system 116c can be related to, combined with, or analogous to any embodiment of the alignment system 135, described earlier, for example in relation to FIGS. 12A-C. Any of these feedback implementations can sense an alignment of one of the iris and the pupil relative to the irradiation delivery system 130, as discussed earlier.

Figure 16C:
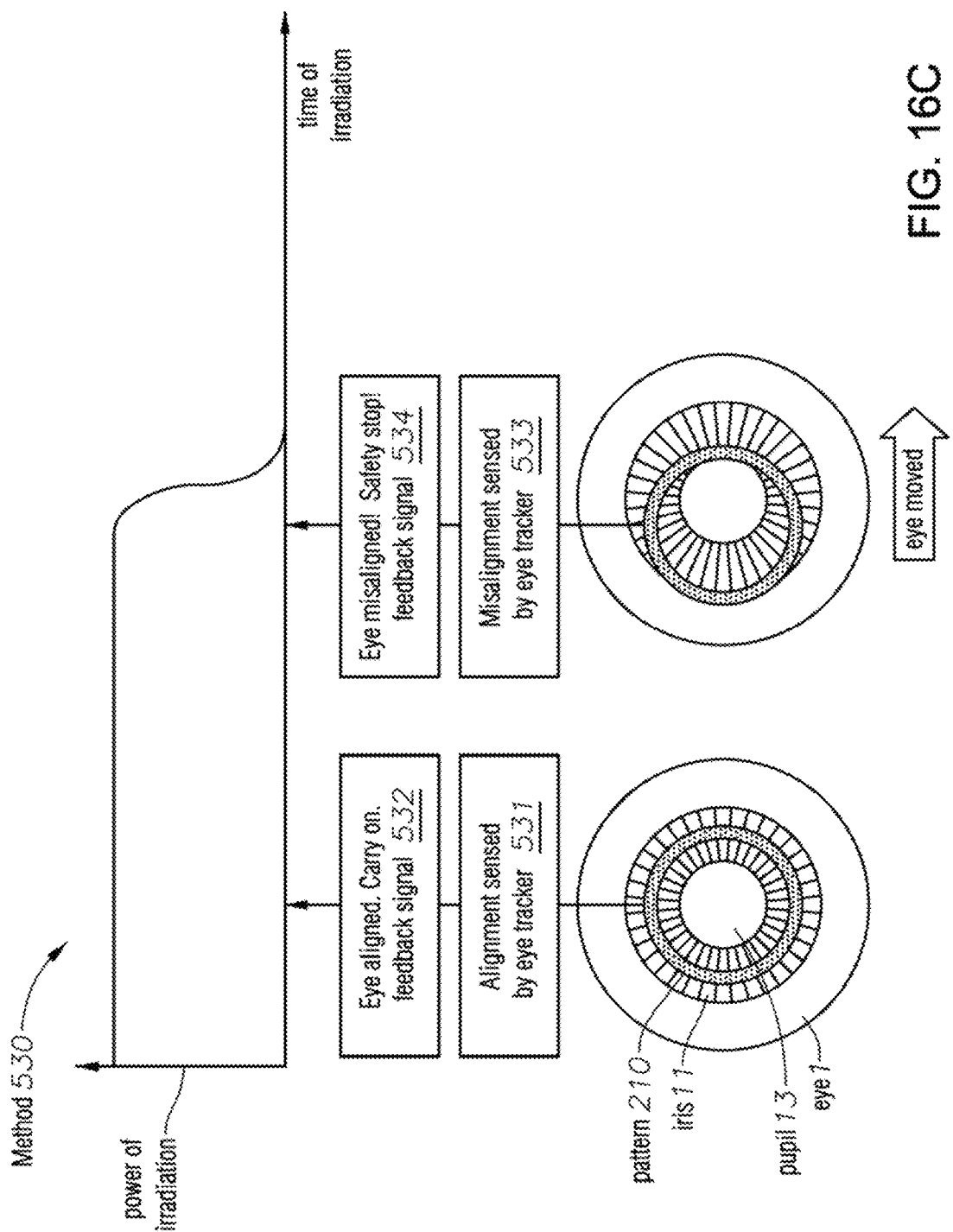

FIG. 16C illustrates a mode of operation, or method 530 for such alignment-related feedback implementations. While FIG. 16C specifically refers to the eye tracker feedback 116d, an analogous process can be practiced with the analogous feedback alignment system 116c, iris scanner 116f, or imaging system 114. In a step 531, the eye tracker 116d can "sense alignment" between the iris 11, the pupil 13 and the irradiation delivery system 130. Sensing alignment in step 531 can lead to generating, in step 532, the feedback "Eye aligned. Carry on irradiation", which results in the irradiation source 120 maintaining the power of the irradiation, as shown by the top graph of FIG. 16C.

A central concern for the efficacy and safety of the irradiation treatment is that the eye 1, iris 11, and pupil 13 remain aligned with the irradiation delivery system throughout the irradiation. However, there is a possibility that the eye, iris, and pupil become misaligned. This can be caused by an involuntary eye movement by the patient, a reaction to a sensation of discomfort or pain by the patient, or a problem developing with the patient interface 137, such as the breaking of a vacuum suction, among others. Also, misalignment can be the natural consequence of the ophthalmologist not using a firm eye-fixation method, such as physically restraining the eyeball only by hand, or by pressure with a forceps. In these cases, the gaze of the eye can naturally drift away to a degree that it becomes misaligned with the pattern 210 and the irradiation delivery system 130.

FIG. 16C illustrates that the eye can get misaligned to a degree that the patterned irradiation 200p may reach the edge of the pupil 13. In such cases, the irradiation may start hitting the retina, a much more light-sensitive tissue. This raises a higher level of safety concerns. Embodiments of the feedback system 116 can handle such developments by the eye tracker 116d "sensing a misalignment", or "misalignment sensed" in step 533. This can lead to a generation of a feedback signal "Eye misaligned! Safety Stop!" in step 534. The irradiation control system 110 can generate a corresponding feedback-based irradiation control signal for the irradiation source 120, which in response can execute a hard stop of the irradiation, as shown by the top graph. The step 534 can be accompanied with a signal to an operator, or user: "Realign at least one of the irradiation delivery system, the iris, and the pupil."

Figure 16D:
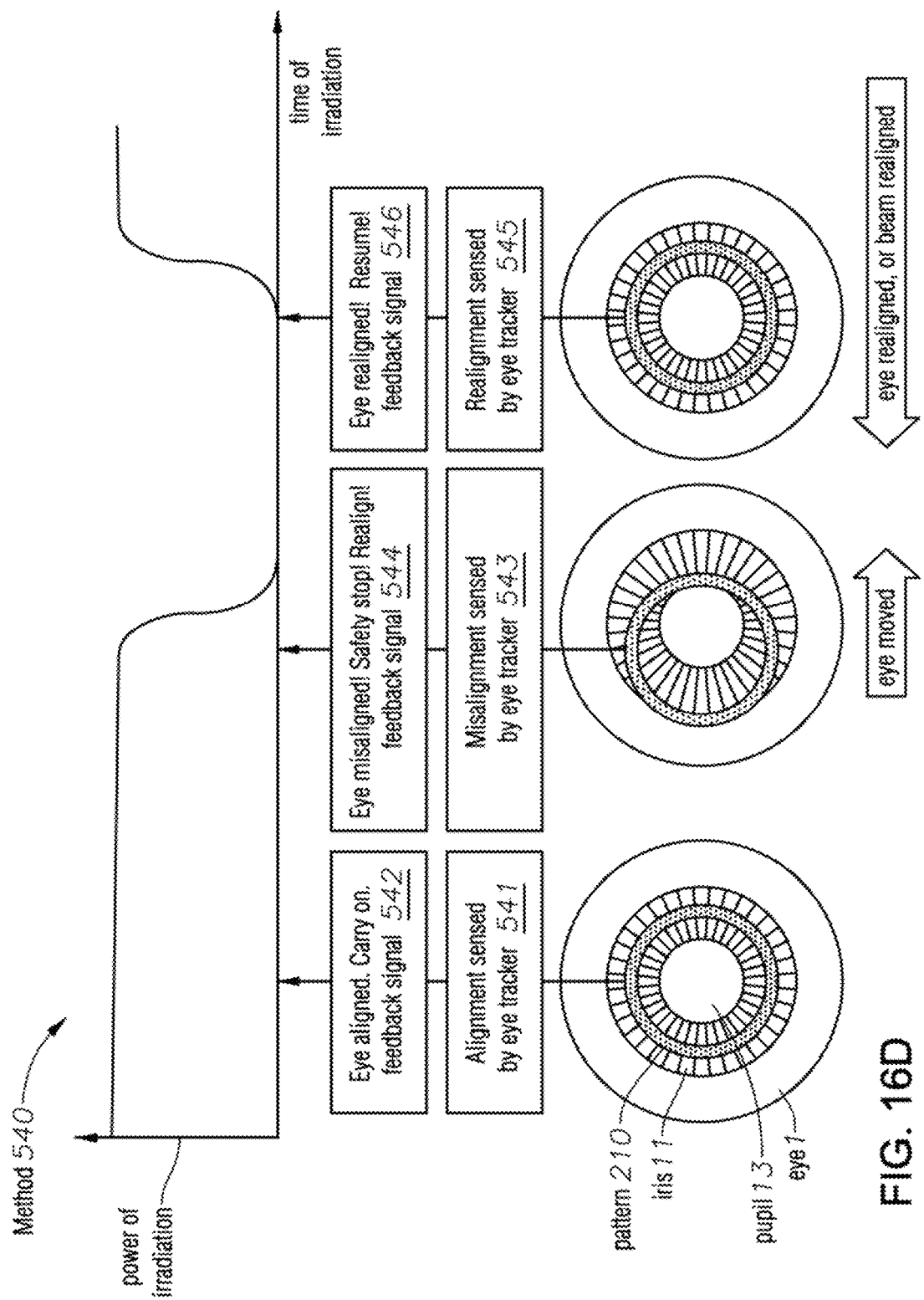

FIG. 16D illustrates a process, or method 540 that flexibly manages naturally occurring misalignments. Steps 541-544 are analogous to steps 531-534, in relation to the eye losing alignment with the irradiation delivery system 120. However, the process 540 can dynamically manage if the misalignment developed not as a safety-threatening problem that required an irreversible hard stop, but as a consequence of a naturally shifting eye, which can be followed by the eye realigning with the irradiation delivery system 130. A typical situation can be when the eye is not docked to the ophthalmic stimulator 100 in a fixed manner with a patient interface 137, but is left free. In such embodiments, the patient may be fixating on a fixation light, but her gaze can be distracted for a short period by natural processes such as a mild discomfort or blinking, after which the patient re-fixates on the fixation light, thus realigning the eye with the irradiation delivery system 130. Such scenarios can be managed by the process 540 via step 545, where the eye tracker 116d can "sense a realignment", followed by step 546, where a feedback signal is generated confirming "Eye realigned. Resume irradiation". The irradiation control system 110 can then generate a feedback-based irradiation control signal that makes the irradiation source 120 to resume the irradiation.

In some cases, the "stop irradiation 544—resume irradiation 546" sequence can be repeated several times. A notable embodiment can be a hand-held, mobile ophthalmic stimulator 100m, described below in relation to FIGS. 13A-C, where the eye can fall out from alignment relative to the irradiation delivery system 130m repeatedly, followed by the eye getting realigned with the irradiation delivery system 130m of the mobile ophthalmic stimulator 100m repeatedly, since the eyes of the patient are not held firmly in place by an immobilizing system.

Figure 16E:
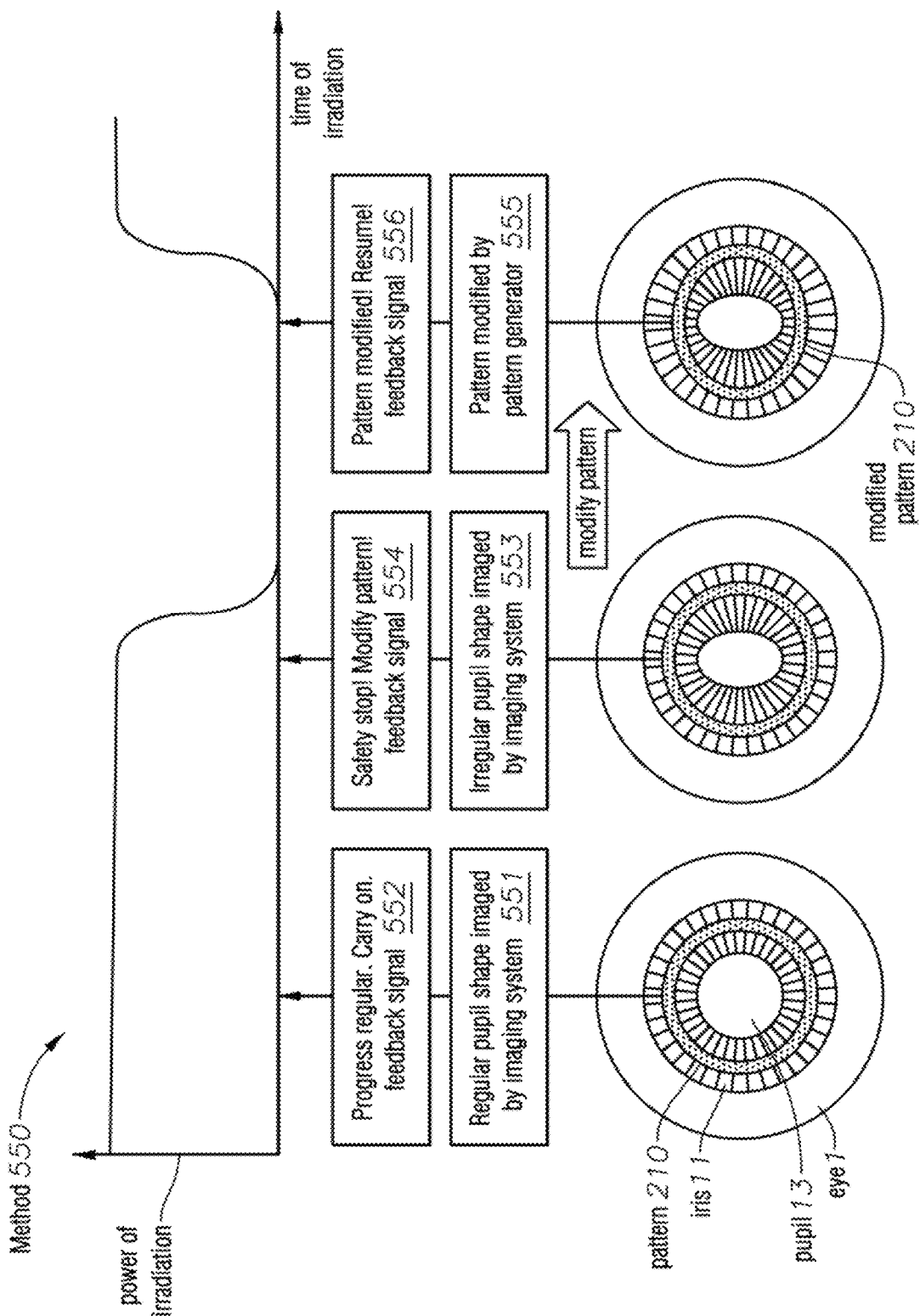

Finally, FIG. 16E illustrates yet another feedback method or process 550. In this method, or process, 550, the feedback system 116 can include at least one of the pupillometer 116a and the imaging system 114, to sense at least one of a pupil characteristic or an iris characteristic, and to generate a feedback according to the sensed characteristic.

In step 551, the imaging system 114 may sense that the pupil 13 has a regular shape. In response, it may generate the feedback signal: "Progress regular. Carry on," in step 552. However, in some cases, in step 553 the imaging system 114 may sense, or image, that an "irregular pupil shape" is emerging as a consequence of the irradiation. In other embodiments, the imaging system 114 may sense, or image, that at least one of a pupil characteristic and an iris characteristic is becoming unacceptable relative to a reference as a consequence of the irradiation. These situations can arise, when the pupil does not react according to medical expectations to the irradiation. A simple example can be that the pupil starts to lose its circular shape, and evolve toward an elongated, or irregular shape. A non-circular pupil can be perceived as an undesirable treatment outcome and therefore necessitates safety protocols within the feedback system 116 to manage or to counter-act it.

A corresponding step 554 can include the generation of a "modify irradiation pattern" feedback signal, possibly preceded by a "safety stop" feedback signal 554. The process 550 can be continued by the pattern generator 112e actually modifying the irradiation pattern 210 in step 555, followed by generating a "Pattern modified. Resume irradiation," feedback 556.

FIG. 16E illustrates a characteristic example, where the pupil 13 starts to evolve from circular towards an elongated oval shape because of the irradiation. This undesirable process can be detected by the imaging system 114 in step 553. In response to the corresponding, feedback-based irradiation control signal, the irradiation delivery system 130 may change the irradiation pattern 210 from a circle into an oval that is oriented 90 degree opposite to the pupil's oval. Such a modified irradiation pattern 210p may be successful to counter-act the development of the undesirable oval pupil.

Irradiation delivery systems 130 and 134 that are digitally controlled and active systems, like the beam modulators and beam scanners 134 of FIGS. 8A-B, and the digitally controlled beam modulators 134 of FIGS. 9A-E, can modify the irradiation patterns 210 relatively easily. The beam-shaping optics 132 of the optical systems in FIGS. 7A-F with little or no digital, point-by-point control can also have some such functionalities. A simple embodiment can be the beam-shaping optics 132 including deformable mirrors. Actuators along the periphery, or along the perimeter of such deformable mirrors can elongate a circular pattern 210 into an oval pattern 210 by a simple cylindrical deformation of the mirror. Other low order wavefront deformations can be also introduced by deforming such a deformable mirror. Such deformable mirrors were also described earlier as systems that can enable the independent tuning of the Rp(inner) and the Rp(outer) radii of the pattern 210, and also in relation to FIGS. 9B-C.

Further embodiments can include further methods or processes, where the feedback system 116 includes the wavefront sensor 116e, or the iris scanner 116f, and the method includes generating a feedback based on a condition of at least one of the iris and the pupil, sensed by the wavefront sensor 116e, or the iris scanner 116f.

In yet other embodiments, the feedback system 116 can be configured to carry out a test and then generate a feedback signal based on the test. In a simple embodiment, during the treatment, a short light pulse can be sent to the eye, and the reaction time, or the reaction radius-change of the pupil can be measured and assessed by the feedback system 116. A feedback-based irradiation control signal can then be generated based on this assessment.

In some cases, the feedback by the feedback system 116 can serve only a diagnostic purpose, not necessarily leading to the generation of a feedback signal to impact the irradiation. This feedback can be a visual feedback for the operator, or user of the ophthalmic stimulator 100 via a user interface 118-1a to 118-1f or 118-2. The user may, in response to this visual feedback, then modify the treatment. The feedback can be a wide variety of information, from pupil size to sensed temperature, to a pupil shape or alignment.

In some embodiments, an ophthalmic stimulator 100 for constricting the pupil 13 of an eye 1 can include an irradiation control system 110, having a safety feedback system 116, to generate a feedback-based irradiation control signal using a feedback of the safety feedback system 116; an irradiation source 120, coupled to the irradiation control system 110, to generate an irradiation 200; and an irradiation delivery system 130, coupled to the irradiation control system 110, to receive the irradiation 200 from the irradiation source 120, and to direct a patterned irradiation 200p in a pattern 210 to a treatment region of an iris 11 of the eye 1, guided by the feedback-based irradiation control signal. In these embodiments, the irradiation control system 110 can control at least one of the irradiation source 120 and the irradiation delivery system 130 with the feedback-based irradiation control signal so that the patterned irradiation 200p causes a long-term constriction of the pupil 13.

Including the safety feedback system 116 can be critically important to guarantee the safety of the operation of the ophthalmic stimulators 100, especially those that are powerful enough to cause a long-term constriction of the pupil 13. In the here-described embodiments, the safety feedback systems 116 are safety-oriented feedback systems, whose role can be critically different from simple guiding or aligning feedback systems which may only help the targeting of the irradiation, but are not part of ensuring the safety of the irradiation. Various embodiments of the safety feedback system 116 can provide feedback when the desired result has been achieved, as determined from a pupil size measurement, for example. This feedback ensures the safety of the treatment by signaling that further irradiation is not necessary and in fact may be harmful. In other embodiments, a feedback can be generated by the safety feedback system 116 if a misalignment has been detected, and the irradiation by the laser source 120L may be inadvertently directed at the retina of the eye 1. Yet other examples include generating a feedback to indicate that a temperature of the target tissue rose to a reference level, or exceeded a critical level. In these embodiments, the feedback of the safety feedback system 116 can indicate that the treatment goal has been achieved, or the possibility of an undesirable medical outcome, such as retinal exposure, or overheating the iris tissue. Receiving such a feedback from the safety feedback system 116 can prompt the irradiation control system 110 to generate a feedback-based irradiation control signal to stop, or to power down the irradiation. Employing such a safety feedback system 116 can ensure that the irradiation is stopped when the treatment goal is achieved, or when there is a possibility of an undesirable medical outcome. As such, including the safety feedback system 116 into the ophthalmic stimulator 100 can be critical to ensure its safe operation.

FIG. 15 illustrates that in some embodiments of the ophthalmic stimulator 100 the safety feedback system 116 can include at least one of a pupillometer 116a and an imaging system 114, to sense a diameter of the pupil, and to generate a feedback according to the sensed pupil diameter. The generated feedback can include at least one of "pupil radius is large relative to a reference, carry on irradiation"; and "pupil radius is sufficiently close to the reference, power down irradiation".

In some embodiments of the ophthalmic stimulator 100, the safety feedback system 116 can include at least one of an infrared camera and a thermal sensor 116b, to sense a temperature of the treatment region, and to generate a feedback according to the sensed temperature. The feedback can include at least one of "sensed temperature is low relative to a reference, carry on irradiation"; "sensed temperature is medium relative to the reference, start power down of irradiation"; and "sensed temperature is high relative to the reference, stop irradiation".

In some embodiments of the ophthalmic stimulator 100, the safety feedback system 116 can include at least one of an alignment system 116c, an eye tracker 116d, an iris scanner 116f, and an imaging system 114, to sense an alignment of one of the iris 11 and the pupil 13 with the irradiation delivery system 130. The feedback can include at least one of: "the irradiation delivery system is aligned with one of the iris and the pupil, carry on irradiation"; and "the irradiation delivery system is misaligned with one of the iris and the pupil, stop irradiation, and realign at least one of the irradiation delivery system, the iris, and the pupil".

With reference to FIG. 8B, in some embodiments of the ophthalmic stimulator 100, the irradiation source 120 can include a laser source 120L that can be a continuous wave laser, a pulsed laser, or a scanned laser. A wide variety of laser sources are known in the art that are useful for ophthalmic applications and can be employed as the irradiation laser source 120L. In particular, femtosecond lasers, with pulse length of 1-1,000 femtosecond and frequencies of 1 kHz.1 MHz have been widely used in the art, and can be used for the laser source 120. Other lasers with longer pulse lengths, in the picosecond or even nanosecond range can be utilized as well.

In some embodiments of the ophthalmic stimulator 100, the irradiation source 120, the irradiation delivery system 130, and the irradiation control system 110 can be configured so that the patterned irradiation causing the long-term constriction of the pupil includes cauterizing iris tissue. Such embodiments can cause permanent alteration of the iris tissue, and therefore can cause permanent shrinking of the pupil.

Figure 13A:
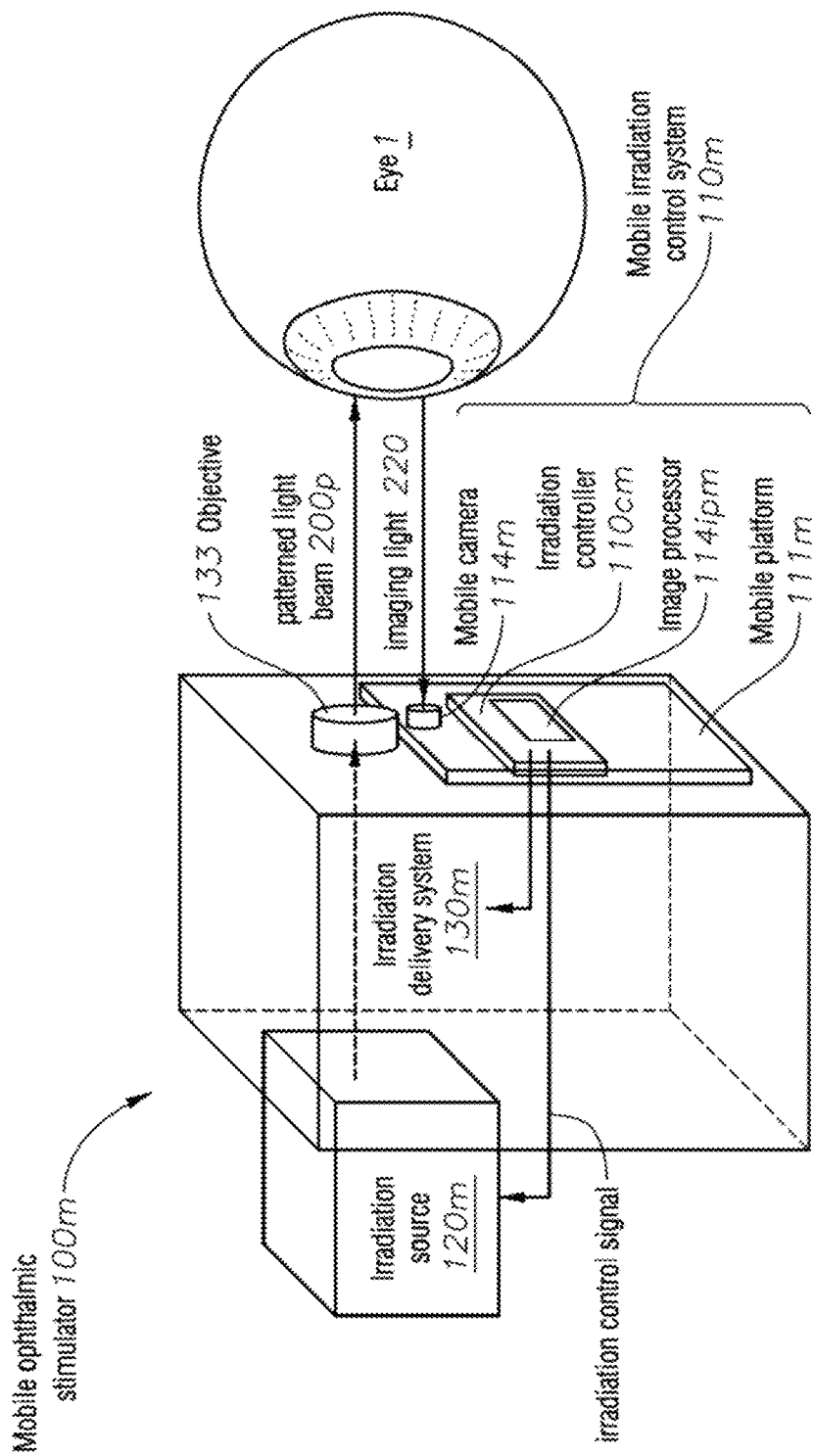
FIGS. 13A-C illustrate mobile embodiment of the ophthalmic stimulator 100.
Figures 13B, 13C:
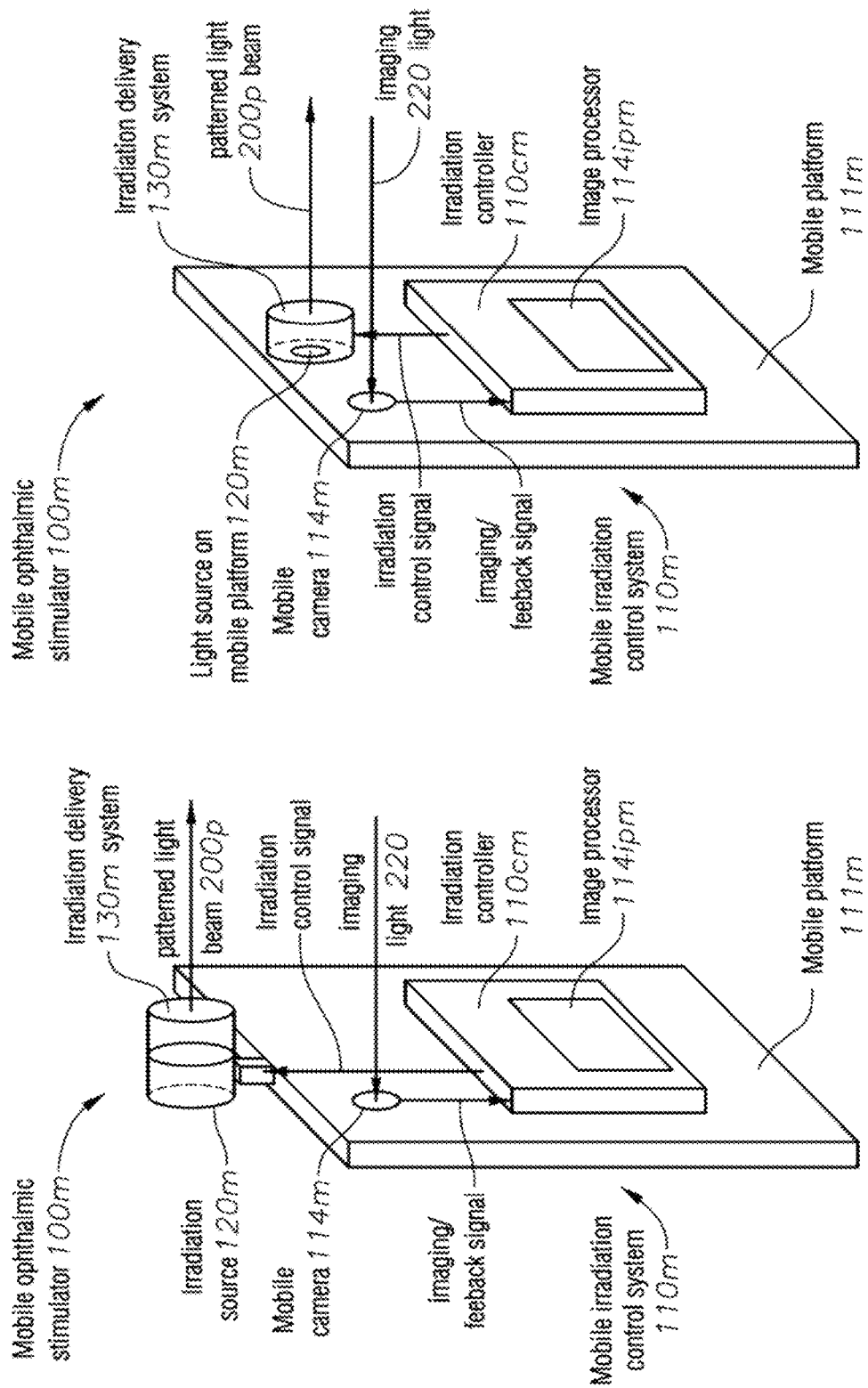

FIGS. 13A-C illustrate a class of mobile implementations of the ophthalmic stimulator 100m, indicated by the label "m". Some of these embodiments will be referred to as a mobile ophthalmic stimulator 100m. FIG. 13A illustrates that this class of embodiments can include a mobile irradiation control system 110m, to generate an irradiation control signal; an irradiation source 120m coupled to the mobile irradiation control system 110m, to generate an irradiation 200; and an irradiation delivery system 130m, coupled to the mobile irradiation control system 110m, to receive the irradiation from the mobile irradiation source 120m, and to deliver a patterned irradiation 200p to an iris of the eye. In embodiments, the mobile irradiation control system 110m can control at least one of the irradiation source 120m and the irradiation delivery system 130m with the irradiation control signal so that the patterned irradiation 200p causes a temporary constriction of the pupil of the eye, without causing a permanent constriction of the pupil.

In embodiments, the mobile irradiation control system 110m can include a mobile communication platform 111m, or simply mobile platform 111m that can be a mobile telephone 111m, a mobile communication device, and a mobile tablet; and a mobile irradiation controller 110cm, installed on the mobile communication platform 111m, to generate the irradiation control signal. In a characteristic embodiment, the mobile irradiation controller 110cm can be a software application, downloaded from a provider over the internet and installed or implemented on a mobile phone 111m. In other embodiments, the mobile irradiation controller 110cm can be a dedicated processor, for example, in a separate box that can be installed on the mobile communication platform 111m by plugging it into the mobile communication platform 111m through a USB port, headphone jack, or charging port. For brevity, the mobile irradiation controller 110cm is sometimes simply referred to as irradiation controller 110cm, where the "m" label indicates the mobile nature of this irradiation controller. The mobile phone 111m itself then can be attached to the remainder of the mobile ophthalmic stimulator 100m, which can be a table-top system that includes the mobile irradiation source 120m, and the mobile irradiation delivery system 130m, installed either in an office of an ophthalmologists, or in a user's residence. In some embodiments, the mobile phone 111m can be coupled to the rest of the ophthalmic stimulator 100m by an electric connector or docking station. In other embodiments, the coupling and communication between the mobile phone 111m and the rest of the ophthalmic stimulator 100m can be a wireless communication, for example through a Bluetooth, or a wi-fi system or channel.

The mobile communication platform 111m can include a memory, to store the above mentioned software implementation of the mobile irradiation controller 110cm; a processor, to execute the stored software implementation of the mobile irradiation controller 110cm; and a user interface, to receive input from a user in relation to an operation of the memory and the processor.

Once the mobile platform 111m or mobile phone 111m is coupled to the rest of the mobile ophthalmic stimulator 100m, a calibration process can be carried out, so that the mobile irradiation control system 110m acquires information about the type and characteristics of the rest of the mobile ophthalmic stimulator 100m. For example, information regarding the power and type of the light beam 200 generated by the irradiation source 120m, and information regarding the type of signaling, communication and control protocols needed for the communication between the mobile platform 111m and the rest of the mobile ophthalmic stimulator 100m.

The irradiation delivery system 130m can include at least one of a pattern generator, an optical beam shaper, a patterning optics, a beam profiler, and a digitally controlled irradiation optics. As in the other related embodiments, the mobile ophthalmic stimulator 100m can be configured to increase a temperature of a treatment region of the iris to a range of 45-60 degrees Celsius.

The mobile irradiation control system 110m can include a mobile imaging system 114m, such as a mobile camera 114m, to generate the irradiation control signal by generating an image of the iris of the eye by the mobile imaging system 114m, receiving an image-based input, and generating the irradiation control signal to control at least one of the irradiation source 120m and the irradiation delivery system 130m to deliver the patterned irradiation according to the received image-based input.

In a characteristic example, the mobile irradiation control system 110m can include a mobile phone 111m that can be attached to the rest of the ophthalmic stimulator 100m that is installed in a medical office as a desktop office device. As such, the irradiation source 120m and the irradiation delivery system 130m can themselves be a movable, light benchtop device that is mobile, but less mobile than the fully mobile platform 111m, or mobile phone 111m. Accordingly, in some embodiments they can be referred to as the mobile irradiation source 120m, and the mobile irradiation delivery system 130m.

The mobile camera 114m of the mobile phone 111m can image the iris 11 and pupil 13 of a patient who is looking into the camera 114m. The mobile irradiation controller 110cm, implemented on the mobile phone 111m, can display the image of the pupil on the screen of the mobile phone 111*m*, and also electronically overlay a proposed irradiation pattern 210. The irradiation control application can then invite the doctor, or user, to modify the pattern within some limits of safety as the image-based input, such as to move the inner and the outer radii Rp(inner) and Rp(outer), while making sure that the pattern 210 remains on the iris 11. Once the modification input is received, possibly together with some treatment parameters, the irradiation control application on the mobile phone 111*m* can send an irradiation control signal to the irradiation source 120*m* and the irradiation delivery system 130*m* wirelessly with a Bluetooth channel. In response, the irradiation source 120*m* and the irradiation delivery system 130*m* can generate and deliver the patterned irradiation 200*p* onto the imaged iris 11.

FIG. 13A illustrates that in some embodiments, the mobile irradiation control system 110*m* can include an image processor 114*ipm*, to receive the image of the iris from the imaging system 114*m*, and to generate the image-based input based on a processing of the image of the iris. In some designs, this image processor 114*ipm* can determine the inner and outer radii Rp(inner) and Rp(outer) of the ring pattern 210, as well as the treatment parameters. There can be hybrid systems, where the image processor 114*ipm* performs the above determinations, however, a user interface 118 of the mobile telephone 111*m* still prompts a surgeon or operator to approve the displayed choices of the imager processor 114*ipm*, as a safety measure.

In some implementations, the image processor 114*ipm* can generate the image-based input by correlating an alignment pattern 138 with the generated image of the iris, in analogy to the alignment system 135 in FIG. 12C. Subsequently, the mobile irradiation control system 110*m* can be configured to generate the irradiation control signal according to the received image-based input that includes a misalignment-warning signal, an alignment-guidance signal, or an irradiation-stop signal, if a misalignment is detected. In a characteristic case, the mobile phone 111*m* can alert the ophthalmologist that a misalignment was detected, possibly also generating an alignment-guidance signal, such as which way to move the eye 1, or the irradiation delivery system 130 to realign the eye and the irradiation delivery system 130.

The ability of the mobile platform 111*m* to communicate can play a very useful role in some implementations. In these designs, the mobile irradiation control system 110*m* can include an on-board communication application, to receive the image of the iris from the imaging system 114*m*, to communicate the received image to a central station 410 having an image processor, and to receive the image-based input from image processor of the central station 410.

FIGS. 13B-C illustrate advanced embodiments, where not the mobile phone 111*m* is attached to the rest of the ophthalmic stimulator 100*m*, but the rest of the ophthalmic stimulator 100*m* is attached to the mobile phone 111*m*, to create a fully mobile ophthalmic stimulator 100*m*.

FIG. 13B illustrates a design of the mobile ophthalmic stimulator 100*m*, wherein the irradiation source 120*m* and the irradiation delivery system 130*m* are part of a small, compact irradiation device 120*m*/130*m*; and the mobile irradiation control system 110*m* is coupled to the irradiation device 120*m*/130*m* to send the irradiation control signal by at least one of an electronic coupling, an electric coupling, a wireless coupling, and an optical coupling.

In the shown example, the irradiation source 120*m* and the irradiation delivery system 130*m* are configured to be electrically coupled to, and mechanically attached to the mobile irradiation control system 110*m*. For example, the irradiation device 120*m*/130*m* can be plugged into one of the ports of the mobile phone 111*m*, such as into the USB port, or into the headphone jack, or the power charging port. In another example, the irradiation device 120*m*/130*m* can be attached to the mobile phone 111*m* by a clip, mini-pliers, or pincer.

FIG. 13C illustrates an example, in which the irradiation source 120*m* is a light source of the mobile irradiation control system 110*m*, and the irradiation delivery system 130*m* is mechanically attached to the mobile irradiation control system 110*m*, to receive a light, generated by the irradiation source 120*m*. In a characteristic example, the flashlight of the mobile phone 111*m* itself can be used as the irradiation source 120*m*. The flashlight of the mobile phone 111*m*, of course, needs to be calibrated to gain control over the power irradiated by its irradiation 200, and possibly filtered or dampened. Nevertheless, using the imaging capabilities of the mobile phones 111*m* and their flashlight can make the mobile ophthalmic stimulator 100*m* much cheaper and compact, and therefore suitable for being carried by a patient as a personal accessory. This aspect can be very useful if irradiation treatments are utilized that cause a temporary constriction of the pupil that lasts less than a day, and thus a once-a-day application in the morning does not secure the pupil constriction for the entire day. Such treatments may need to be refreshed as the day goes on. A portable, personalized, mobile phone-based ophthalmic stimulator 100*m* can be the answer for the need for refreshing treatments during the day.

Obviously, safety is a high priority consideration for the mobile embodiments of the stimulator 100*m* that are not operated by trained ophthalmologists. Moreover, achieving and preserving alignment for the duration of the treatment also becomes an elevated challenge for mobile stimulator 100*m*. Mobile stimulators 100*m* can address these concerns, by practicing the method, or process 540, illustrated in FIG. 16D. It is recalled here, that in step 543, if the imaging system 114, the alignment system 116*c*, or the eye tracker 116*d* sense a misalignment, then they can induce the generation of a feedback-based irradiation control signal that makes the irradiation source 120*m* stop the irradiation 200. Implementing this imaging-triggered "safety stop" process makes mobile stimulators 100*m* safe, and minimizes undesirable retinal exposure.

Moreover, if the eye gets realigned, for example, because the user moves either the hand-held mobile phone 111*m*, or moves her/his gaze, then the imaging system 114, or its equivalents, can sense the realignment in step 545, and the irradiation controller 110*m* can cause the restart the irradiation. These stop 543—restart 545 steps can be performed repeatedly, as, for example, the handheld mobile phone 111*m* is moving in the patient's hand.

An interrupted, or multiply interrupted irradiation treatment may take longer to achieve the temperature rise required for the desired pupil constriction, and to administer the treatment for the time necessary for efficacy. Therefore, mobile stimulators 100*m* can include at least one of a thermal camera, an infrared camera and a thermal sensor 116*b*, to track an amount of time a treatment region of the iris had a temperature in a predetermined range. In an example, the irradiation controller 110*m* may add up the multiply interrupted time-segments, when the treatment region of the iris was at the prescribed temperature, and ensure that the treatment region has been held at the prescribed temperature range for the time interval necessary to achieve the targeted pupil constriction. For example, the IR sensor 116*b* can track that the treated ring 210*r* of the iris 11 remains at 55 Celsius for a prescribed time, such as for 20 seconds, or for 40 seconds, in order to achieve a pupil constriction that will last all day.

In some embodiments, the safety stop 543—restart 545 steps can be also performed under the control of the central station 410. In such embodiments, it can be the image processor of the central station 410 that senses the misalignment of the patterned irradiation relative to the iris or the pupil, as well as that senses the realignment, prompting the generation of the restart command.

Finally, the central station 410 can perform monitoring functions over a series of treatments performed by the mobile ophthalmic stimulator 100m. In some embodiments, the mobile stimulator 100m can be configured to take and send the image of the iris to the central station 410 for monitoring, to receive a monitoring-based control signal from the central station, and to generate the irradiation control signal in accordance with the received monitoring-based control signal. For example, the images, sent by the stimulator 100m, can be analyzed by the central station 410. This analysis can recognize that the treatment is inducing an undesirable effect in the retina over the term of several treatments. In such case, the central station may send out a monitoring-based control signal to the mobile stimulator 100m to either prevent the user from administering further treatments, or to change a treatment parameter, such as to reduce a power or intensity of the patterned irradiation 200p. Such central station-related systems are described next.

Figure 14:
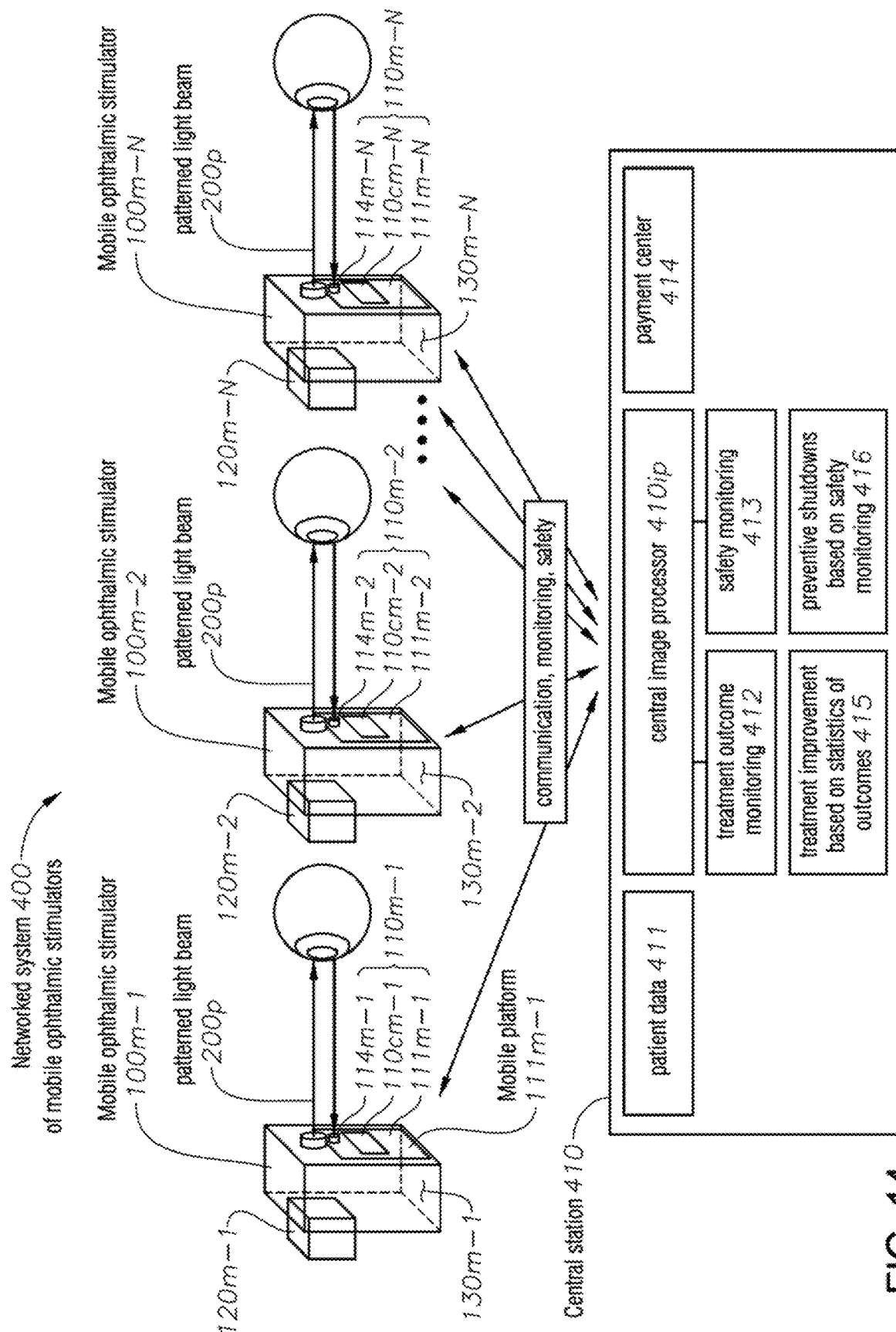
FIG. 14 illustrates a mobile network of self-treatment stimulators 400.

FIG. 14 illustrates a networked system 400 of ophthalmic stimulators for temporarily constricting eye-pupils. The networked system 400, or mobile network 400, can include a set of mobile ophthalmic stimulators 100m-1, 100m-2, . . . 100m-N, collectively referred to as mobile ophthalmic stimulators 100m-i, each mobile ophthalmic stimulator 100m-i including a mobile irradiation control system 110m-i, to generate an irradiation control signal; an irradiation source 120m-i, coupled to the irradiation control system 110m-i, to generate an irradiation; and an irradiation delivery system 130m-i, coupled to the mobile irradiation control system 110m-i, to receive the irradiation from the irradiation source 120m-i, and to deliver a patterned irradiation 200p to an iris of the eye; wherein the mobile irradiation control system 110m-i controls at least one of the irradiation source 120m-i and the irradiation delivery system 130m-i with the irradiation control signal so that the patterned irradiation 200p causes a temporary constriction of the pupil of the eye, without causing a permanent constriction of the pupil.

The networked system 400 further includes a central station 410, including a central image processor, wherein the mobile irradiation control systems 110m-i of the mobile ophthalmic stimulators 100m-i and the central station 410 are configured to communicate through a communication network. In this section, the term mobile ophthalmic stimulator 100m-i encompasses all embodiments described in relation to FIGS. 13A-C.

In embodiments of the networked system 400, each mobile irradiation control system 110m-i can include a mobile communication platform 111m-i, including at least one of a mobile telephone, a mobile communication device, and a mobile tablet; and a mobile irradiation controller 110cm-i, implemented on the mobile communication platform 111m-i, to generate the irradiation control signal. In embodiments, the mobile communication platforms 111m-i can include a memory, to store a software implementation of the mobile irradiation controller 110cm-i; a processor, to execute the stored software implementation of the mobile irradiation controller 110cm-i; and a user interface, to receive input from a user in relation to an operation of the memory and the processor. In embodiments, the mobile ophthalmic stimulators can be configured to increase a temperature of a treatment region of the iris to a range of 45-60 degrees Celsius.

Each mobile irradiation control system 110m-i can include an imaging system 114m-i, to generate the irradiation control signal by generating an image of the iris of the eye by the imaging system 114m-i, receiving an image-based input, and generating the irradiation control signal to control at least one of the irradiation 120m-i source and the irradiation delivery system 130m-i to deliver the patterned irradiation 200p according to the received image-based input.

In some characteristic embodiments, the mobile irradiation control systems 11m-i can include an image processor 114ipm-i, to receive the image of the iris from the imaging system, and to generate the image-based input based on a processing of the image of the iris. In FIG. 14, the image processors 114ipm-i are not shown for scarcity of space. Embodiments of the image processors 114ipm-i have been shown and described earlier, such as in FIG. 6A. As described earlier, the on-board image processors 114ipm-i, can generate an image-based input for the irradiation control systems 110m-i, which then can control the rest of the mobile ophthalmic stimulators 100m-i accordingly. In such embodiments, the communications of the mobile ophthalmic stimulators 100m-i with the central station 410 can be a recording of the results of the image processing, and the record of the treatments performed by the mobile ophthalmic stimulators 100m-i.

In other embodiments, each ophthalmic stimulator 100m-i can be configured to send the image of the iris to the central station 410; and the central station 410 can be configured to analyze the received image by a central image processor 410ip, and to respond to the sending mobile ophthalmic stimulator 100m-i with the image-based input based on the analysis. This communication and analysis can be real-time, actionable. In other cases, it can be a post-treatment, recording the actions type communication.

In real-time embodiments, each ophthalmic stimulator 100m-i can be configured to generate and to send the image of the iris to the central station 410 before the irradiation delivery system delivers 130m-i the patterned irradiation to the iris; and the central station 410 can be configured to respond to the sending ophthalmic stimulator 100m-i with the image-based input that indicates whether the central station 410 authorizes the irradiation delivery system 130-i of the ophthalmic stimulator 100m-i to deliver the patterned irradiation to the iris.

Clearly, such preauthorization-based networked systems 400 have safety benefits, as when the patient intends to use the mobile ophthalmic stimulator 100m-i, the stimulator 100m-i first needs to send an image of the iris to be treated to the central station 410. This gives a chance for the central image processor 410ip to analyze the image of the iris, and if it finds anything that raises a medical concern, such as a shape change, or an unexpected discoloration, the central station 410 can communicate a "Treatment not authorized" imaging-based input to the mobile stimulator 100m-i, which then prevents the mobile stimulator 100m-i from irradiating the iris when medical concerns have been raised by the image analysis.

In a related embodiment of the networked system 400, each ophthalmic stimulator 100m-i can be configured to generate, and to send, the image of the iris to the central station 410 before the irradiation delivery system 130m-i delivers the patterned irradiation 200p to the iris; and the central station 410 can be configured to respond to the sending mobile ophthalmic stimulator 100*m-i* with the image-based input that indicates irradiation parameters to be used by the irradiation delivery system 130*m-i* of the mobile ophthalmic stimulator 100*m-i* when delivering the patterned irradiation to the iris.

The safety aspects of this embodiment are quite similar to the previous one. One of the differences is that the imaging-based input from the central station is not a binary "authorized-not authorized" input, but a quantitative input, nuanced input. In a characteristic example, the central image processor 410*ip* can notice a small discoloration of the iris in the image, sent in by the mobile stimulator 100*m-i*. However, the discoloration may be small enough so that a hard-stop "Treatment not authorized" input may be excessive. In such cases, the central image processor 410*ip* can respond instead by a message of "Reduce power of irradiation in next treatment" input. In some embodiments, the central image processor 410*ip* can even schedule a follow-up imaging, to check how the iris reacted to the reduced power irradiation: was the reduction sufficient to eliminate the discoloration, or further analysis is needed.

In some embodiments, the central imaging processor 410*ip* of the central station 410 can be configured to perform a medical analysis of the image of the iris, and to respond to the sending ophthalmic stimulator 100*m-i* with the image-based input that indicates if a negative medical condition was found by the analysis. The medical analysis can take place in a number of ways. The central station 410 can engage in an automated medical analysis, where for example past images of the iris, recalled from a memory, are compared to the present image. Or, the image of the iris can be compared to a database, compiled from tracking a large number of irises. Some embodiments can use artificial intelligence systems to recognize, and to evaluate the negative medical condition, such as an inflammation of the iris. Or, the image processor can flag the image, and request an opinion or analysis by a human specialist.

The negative medical condition can also be a wide range of conditions, including a change of color of the iris, a change of an optical characteristic, and a change of shape of the iris.

In some advanced embodiments, the mobile ophthalmic stimulators 100*m-i* can be configured to test the iris 11 and to send a test result to the central station 410; and the central station 410 can be configured to perform a medical analysis of the test result, and to respond to the sending mobile ophthalmic stimulators 100*m-i* with the image-based input that indicates if a negative medical condition was found by the analysis. The mentioned test of the iris can include irradiating the iris with a test irradiation, and measuring a constriction of the pupil in response to the test irradiation. The performing a medical analysis can include recalling a previous test result, as mentioned. Finally, the detection of a negative medical condition can include comparing the test result with the previous test result, and finding the test result less acceptable than the previous test result. In other embodiments, the comparison can be made not with past measurements or tests on the same iris, but to a database of a large number of irises. This database can be organized into groups according to many shared traits, so that patients with comparable medical situations and characteristics are compared by the database.

As mentioned in relation to the mobile stimulators 100*m* of FIGS. 13A-C earlier, in another class of embodiments, the mobile ophthalmic stimulators 100*m-i* can be configured to send alignment data to the central station 410 regarding an alignment of the patterned irradiation 200*p* with at least one of the iris and the pupil; and the central station 410 can be configured to evaluate the alignment data; and to send a control signal to stop the patterned irradiation 200*p* when the patterned irradiation 200*p* is evaluated to be misaligned with at least one of the iris and the pupil. In some embodiments, the alignment data can be generated by the imaging system 114*m*. In others, by various embodiments of the alignment system 135, possibly using the patient interface 137 and the alignment pattern 138. In imaging-based embodiments, the control signal can be analogous to the image-based input, described earlier.

Generally speaking, in some embodiments of the networked system 400 the mobile irradiation control systems 110*m-i* of the mobile ophthalmic stimulators 100*m-i* and the central station 410 can be configured to communicate regarding safety monitoring of the irradiations and treatments by an interface, or dedicated block or code 413. This is a generic concept that encompasses communication regarding all major safety monitoring channels, including expected and unexpected medical outcomes, treatment parameters, proper alignment, and test results, from the viewpoint of safety. As described, the safety monitoring can result prompting a dedicated block, processor, or code 416 to signal or order preventive shutdowns of the mobile stimulators.

Analogous communications can be performed by a treatment outcome monitoring block, dedicated processor, or code 412. Communications about treatment outcomes can then be used by a block, dedicated processor, or piece of code 415, to develop and assemble a statistics of the treatment outcomes with the purpose of improving the understanding and the operations of the networked system 400 for the benefit of the patients. This communication channel can, of course, also be useful for pushing out new versions of treatment software from the central station 410 to the individual mobile stimulators 100*m-i*.

These communications may not be real time, or actionable. In some embodiments, for example, the mobile irradiation control systems 110*m-i* of the mobile ophthalmic stimulators 100*m-i* and the central station 410 can be configured to communicate treatment outcomes after an irradiation has been performed. In other embodiments, they can be configured to communicate regarding patient data, which then can be stored in a dedicated processor and memory 411.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. A networked system of mobile ophthalmic stimulators for temporarily constricting eye-pupils, comprising:
   a set of mobile ophthalmic stimulators, each mobile ophthalmic stimulator including a mobile irradiation control system, to generate an irradiation control signal; an irradiation source, coupled to the irradiation control system, to generate an irradiation; and an irradiation delivery system, coupled to the mobile irradiation control system, to receive the irradiation from the irradiation source, and adapted to deliver a patterned irradiation with a power density in a range of 0.1-1000 mW/cm·sup.2 to an iris of an eye; wherein the mobile irradiation control system controls at least one of the irradiation source and the irradiation delivery system with the irradiation control signal so that the patterned irradiation with the power density causes a temporary constriction of the pupil of the eye including an at least 5% reduction of a radius of the pupil that lasts between one hour and one day in response to delivering the patterned irradiation for a time period in a range of 1-100 seconds to minimize retinal exposure; and a central station, wherein the mobile irradiation control systems of the of the ophthalmic stimulators and the central station are configured to communicate through a communication network.

2. The networked system of claim 1, each mobile irradiation control system comprising:

a mobile communication platform, including at least one of a mobile telephone, a mobile communication device, and a mobile tablet; and a mobile irradiation controller, installed on the mobile communication platform, to generate the irradiation control signal.

3. The networked system of claim 2, the mobile communication platforms comprising:

a memory, to store a software implementation of the mobile irradiation controller;

a processor, to execute the software implementation of the mobile irradiation controller; and a user interface, to receive input from a user in relation to an operation of the memory and the processor.

4. The networked system of claim 1, wherein:

the mobile ophthalmic stimulator is configured to increase a temperature of a treatment region of the iris to a range of 45-60 degrees Celsius.

5. The networked system of claim 1, the mobile irradiation control systems comprising:

an imaging system, to generate the irradiation control signal by generating an image of the iris of the eye by the imaging system, receiving an image-based input, and generating the irradiation control signal to control at least one of the irradiation source and the irradiation delivery system to deliver the patterned irradiation according to the received image-based input.

6. The networked system of claim 5, the mobile irradiation control systems comprising:

an image processor, to receive the image of the iris from the imaging system, and to generate the image-based input based on a processing of the image of the iris.

7. The networked system of claim 5, wherein:

each mobile ophthalmic stimulator is configured to send the image of the iris to the central station; and the central station is configured to analyze the received image by a central image processor, and to respond to the sending ophthalmic stimulator with the image-based input based on the analysis.

8. The networked system of claim 7, wherein:

each mobile ophthalmic stimulator is configured to generate and to send the image of the iris to the central station before the irradiation delivery system delivers the patterned irradiation to the iris; and the central station is configured to respond to the sending mobile ophthalmic stimulator with the image-based input that indicates authorization of the irradiation delivery system of the ophthalmic stimulator by the central station to deliver the patterned irradiation to the iris.

9. The networked system of claim 7, wherein:

each mobile ophthalmic stimulator is configured to generate and to send the image of the iris to the central station before the irradiation delivery system delivers the patterned irradiation to the iris; and the central station is configured to respond to the sending mobile ophthalmic stimulator with the image-based input that indicates irradiation parameters to be used by the irradiation delivery system of the ophthalmic stimulator when delivering the patterned irradiation to the iris.

10. The networked system of claim 7, wherein:

the central imaging processor of the central station is configured to perform a medical analysis of the image of the iris, and to respond to the sending mobile ophthalmic stimulator with the image-based input that indicates a finding of a negative medical condition by the analysis.

11. The networked system of claim 10, wherein:

the medical analysis includes recalling a previous image of the imaged iris from a memory and the negative medical condition is one of a change of color of the iris, a change of an optical characteristic, and a change of shape of the iris.

12. The networked system of claim 5, wherein:

the mobile ophthalmic stimulators are configured to test the iris and to send a test result to the central station; and the central station is configured to perform a medical analysis of the test result, and to respond to the sending mobile ophthalmic stimulators with the image-based input that indicates a finding of a negative medical condition by the analysis.

13. The networked system of claim 12, wherein: the test of the iris includes irradiating the iris with a test irradiation, and measuring a constriction of the pupil in response to the test irradiation;

the performing the medical analysis includes recalling a previous test result;

and the finding of the negative medical condition includes comparing the test result with the previous test result, and finding the test result less acceptable than the previous test result.

14. The networked system of claim 1, wherein:

the mobile ophthalmic stimulators are configured to send alignment data to the central station regarding the alignment of the patterned irradiation with at least one of the iris and the pupil; and the central station is configured to evaluate the alignment data; and to send a control signal to stop the patterned irradiation when the patterned irradiation is evaluated to be misaligned with at least one of the iris and the pupil.

15. The networked system of claim 1, wherein:

the mobile irradiation control systems of the mobile ophthalmic stimulators and the central station are configured to communicate treatment outcomes.

16. The networked system of claim 1, wherein:

the mobile irradiation control systems of the mobile ophthalmic stimulators and the central station are configured to communicate regarding safety monitoring of treatments.

17. The networked system of claim 1, wherein:

the mobile irradiation control systems of the mobile ophthalmic stimulators and the central station are configured to communicate regarding patient data.

* * * * *